US007153968B2

(12) United States Patent
Dube et al.

(10) Patent No.: US 7,153,968 B2
(45) Date of Patent: Dec. 26, 2006

(54) 8-(BIARYL)QUINOLINE PDE4 INHIBITORS

(75) Inventors: Daniel Dube, St. Lazare (CA); Michel Gallant, Montreal (CA); Patrick Lacombe, Montreal (CA); Denis Deschenes, Dorval (CA); Laurence Dube, Pierrefonds (CA); Yves Girard, Ile-Bizard (CA); Dwight Macdonald, L'lle Bizard (CA)

(73) Assignee: Merck Frosst Canada, Ltd., Kirkland (CA)

( * ) Notice: Subject to any disclaimer, the term of this patent is extended or adjusted under 35 U.S.C. 154(b) by 20 days.

(21) Appl. No.: 10/517,416

(22) PCT Filed: Jun. 23, 2003

(86) PCT No.: PCT/CA03/00957

§ 371 (c)(1),
(2), (4) Date: Dec. 8, 2004

(87) PCT Pub. No.: WO04/000814

PCT Pub. Date: Dec. 31, 2003

(65) Prior Publication Data

US 2005/0234238 A1    Oct. 20, 2005

Related U.S. Application Data

(60) Provisional application No. 60/428,313, filed on Nov. 22, 2002, provisional application No. 60/391,364, filed on Jun. 25, 2002.

(51) Int. Cl.
*C07D 219/08*  (2006.01)
*C07D 215/12*  (2006.01)
*A61K 31/47*   (2006.01)

(52) U.S. Cl. .................. 546/107; 546/173; 514/311; 514/314

(58) Field of Classification Search ................ 514/311, 514/314; 546/107, 173
See application file for complete search history.

(56) References Cited

U.S. PATENT DOCUMENTS 5,455,252 A * 10/1995 Wilhelm et al. ............ 514/311
5,530,005 A    6/1996 Wilhelm et al.
6,069,151 A    5/2000 Dyke et al.

FOREIGN PATENT DOCUMENTS

WO    WO 02/094823    11/2002

OTHER PUBLICATIONS

MacDonald, D. et al., Journal of Medicinal Chemistry, vol. 43, No. 21, pp. 3820-3823, (2000).
Houslay, et al—Drug Discovery Today, 10 (22) pp. 1503-1519, 2005.
Meijsing, et al—Cancer Letters, 188, pp. 53-58, 2002.
Ochi, et al—Life Sciences, 77, pp. 2040-2050, 2005.
Compton, et al—The Lancet, vol. 358, pp. 265 270, 2001.
Rabe, et al—The Lancet, vol. 366, pp. 563-571, 2005.
Rose, et al—Current Pharmaceutical Design, vol. 11, pp. 3329-3334, 2005.

* cited by examiner

*Primary Examiner*—D. Margaret Seaman
(74) *Attorney, Agent, or Firm*—Curtis C. Panzer; David L. Rose

(57) ABSTRACT

8-(biaryl) quinolines wherein the bi-aryl group at the 8-position is in a meta relationship to the quinoline group, are PDE4 inhibitors useful in the treatment of asthma, chronic bronchitis, chronic obstructive pulmonary disease, eosinophilic granuloma, psoriasis and other benign or malignant proliferative skin diseases, endotoxic shock, laminitis in horses, colic in horses, septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection, graft versus host disease, hypersecretion of gastric acid, bacterial, fungal induced sepsis, viral induced sepsis, fungal induced septic shock, viral induced septic shock, inflammation-mediated chronic tissue degeneration, cytokine-mediated chronic tissue degeneration, osteoarthritis, cancer, cachexia, muscle wasting, depression, memory impairment, tumour growth, or cancerous invasion of normal tissues. In another aspect, the present invention is directed to a method of enhancing cognition in a healthy subject comprising administering a safe cognition enhancing amount of phosphodiesterase-4 inhibitor. In particular, this invention is directed to a method of enhancing memory, learning, retention, recall, awareness and judgement in health subjects comprising administering a safe and cognition enhancing amount of a phosphodiesterase-4 inhibitor.

23 Claims, No Drawings

«8-(BIARYL)QUINOLINE PDE4 INHIBITORS»

CROSS-REFERENCE TO RELATED APPLICATIONS

This is a National Stage application of International application PCT/CA2003/000957, filed Jun. 23, 2003. This applcation also claims priority from U.S. Provisional application 60/391,364, filed Jun. 25, 2002 and 60/428,313, filed Nov. 22, 2002.

BACKGROUND OF THE INVENTION

1. Field of the Invention

The present invention is directed to compounds that are substituted 8-(biaryl)quinolines. In particular, this invention is directed to substituted 8-(biaryl)quinolines which are phosphodiesterase-4 inhibitors wherein the biaryl group at the 8-position is in a meta relationship to the quinoline group.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), *Ann. Rep. In Med. Chem.*, 33:91–109 (1998). B. Hughes et al., *Br. J. Pharmacol.*, 118:1183–1191 (1996); M. J. Perry et al., *Cell Biochem. Biophys.*, 29:113–132 (1998); S. B. Christensen et al., *J. Med. Chem.*, 41:821–835 (1998); and Burnouf describe the wide variation of the severity of the undesirable side effects exhibited by various compounds. As described in M. D. Houslay et al., *Adv. In Pharmacol.*, 44:225–342 (1998) and D. Spina et al., *Adv. In Pharmacol.*, 44:33–89 (1998), there is great interest and research of therapeutic PDE4 inhibitors.

International Patent Publication WO9422852 describes quinolines as PDE4 inhibitors. International Patent Publication WO9907704 describes 1-aryl-1,8-naphthylidin-4-one derivatives as PDE4 inhibitors.

A. H. Cook, et al., *J. Chem. Soc.*, 413–417 (1943) describes gamma-pyridylquinolines. Other quinoline compounds are described in Kei Manabe et al., *J. Org. Chem.*, 58(24):6692–6700 (1993); Kei Manabe et al., *J. Am. Chem. Soc.*, 115(12):5324–5325 (1993); and Kei Manabe et al., *J. Am. Chem. Soc.*, 114(17):6940–6941 (1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to novel substituted 8-(biaryl)quinolines that are PDE4 inhibitors, wherein the biaryl group at the 8-position is in a meta relationship to the quinoline group. This invention also provides a pharmaceutical composition which includes an effective amount of the novel substituted 8-arylquinoline and a pharmaceutically acceptable carrier.

This invention further provides a method of treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, and xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by by the administration of an effective amount of the novel substituted 8-(biaryl)quinoline or a precursor compound which forms in vivo the novel substituted 8-(biaryl)quinoline.

In another aspect, the present invention is directed to a method of enhancing cognition in a healthy subject comprising administering a safe cognition enhancing amount of a phosphodiesterase-4 inhibitor. In particular, this invention is directed to a method of enhancing memory, learning, retention, recall, awareness and judgement in health subjects comprising administering a safe and cognition enhancing amount of a phosphodiesterase-4 inhibitor.

DETAILED DESCRIPTION OF THE INVENTION

A compound of this invention is represented by Formula (I):

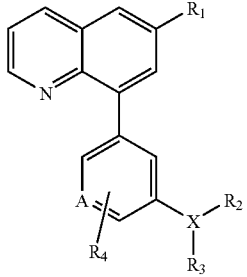

or a pharmaceutically acceptable salt thereof, wherein

A is C or N;

X is phenyl, pyridyl, pyrazinyl, thiaphenyl, quinolinyl, benzofuranyl, oxadiazolyl, diazolylpyridinyl, imidazolylpyridinyl, oxadiazolylphenyl, or benzodioxolyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)C$_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$ alkyl, —$C_{0-4}$alkyl-$C_{3-6}$cycloalkyl-$C_{0-6}$alkyl-C(O)—$C_{0-6}$ alkyl, —$C_{0-4}$alkyl-$C_{3-6}$cycloalkyl-$C_{0-6}$alkyl-C(O)—$C_{0-6}$ alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)—$C_{3-6}$cycloalkyl, —$C_{2-6}$alkenyl-C(O)—$C_{0-4}$alkyl-N($C_{0-4}$ alkyl)—$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$ alkyl-O—$C_{0-4}$alkyl, —S(O)—$C_{0-6}$alkyl, —P(O)(O—$C_{0-4}$ alkyl)(O—$C_{0-4}$alkyl), —$C_{2-6}$alkenyl-C(O)—$C_{0-4}$alkyl-N($C_{0-4}$alkyl)-pyridyl, —S—$C_{1-6}$alkyl, —$C_{0-6}$alkyl-N($C_{0-6}$ alkyl)—C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl ($C_{0-4}$alkyl), —$C_{0-4}$alkyl-C(O)—$C_{0-4}$alkyl-phenyl, —$C_{0-4}$ alkyl-O—$C_{0-4}$alkyl-phenyl, —$C_{0-4}$alkyl-$C_{3-6}$cycloalkyl-$C_{0-4}$ alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$ alkyl-diazolyl($C_{0-4}$alkyl), —$C_{0-4}$alkyl-S—$C_{1-4}$alkyl-Si($C_{0-4}$ alkyl)$_3$, —$C_{0-4}$alkyl-S—$C_{0-4}$alkyl-phenyl($C_{0-4}$alkyl), —$C_{0-4}$ alkyl-S—$C_{0-4}$alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In one aspect, the compound of this invention is represented by Formula (I), or a pharmaceutically acceptable salt thereof, wherein.

A is C;

X is phenyl, pyridyl, pyrazinyl, thiaphenyl, quinolinyl, benzofuranyl, oxadiazolyl, diazolylpyridinyl, imidazolylpyridinyl, oxadiazolylphenyl, or benzodioxolyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$ alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, —$C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$alkyl-C(O)—$C_{0-6}$alkyl-N ($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N ($C_{0-6}$alkyl)-pyridyl, —$C_{0-6}$alkyl-C(O)—$C_{0-4}$alkyl-N($C_{0-4}$ alkyl)$_2$, —$C_{0-6}$alkyl-C(O)—$C_{0-4}$alkyl-N($C_{0-4}$alkyl)—$C_{3-6}$ cycloalkyl, —$C_{2-6}$alkenyl-C(O)—$C_{0-4}$alkyl-N($C_{0-4}$ alkyl)—$C_{3-6}$cycloalkyl, —$SO_2$—$C_{0-6}$alkyl-phenyl, —$SO_2$—$C_{0-6}$ alkyl-(—$C_{0-6}$alkyl-phenyl)(—$C_{0-6}$alkyl-phenyl), —$C_{0-4}$ alkyl-$SO_2$—$C_{0-4}$alkyl-$C_{3-6}$cycloalkyl-$C_{0-4}$ alkyl-C(O)—$C_{0-4}$ alkyl-O—$C_{0-4}$alkyl, —S(O)—$C_{0-6}$alkyl, —P(O)(O—C$_{0-4}$alkyl)(O—C$_{0-4}$alkyl), —C$_{2-6}$alkenyl-C(O)—C$_{0-4}$alkyl-N(C$_{0-4}$alkyl)-pyridyl, S—C$_{1-6}$alkyl, —C$_{0-6}$alkyl-N(C$_{0-6}$alkyl)-C(O)—C$_{0-6}$alkyl, —C$_{0-6}$alkyl-N(C$_{0-6}$alkyl)-C(O)—N(C$_{0-6}$alkyl)$_2$, —C$_{0-4}$alkyl-S—C$_{1-4}$alkyl-oxadiazolyl(C$_{0-4}$alkyl), —C$_{0-4}$alkyl-C(O)—C$_{0-4}$alkyl-phenyl, —C$_{0-4}$alkyl-O—C$_{0-4}$alkyl-phenyl, —C$_{0-4}$alkyl-C$_{3-6}$cycloalkyl-C$_{0-4}$alkyl-tetrazolyl, —SO$_2$—N(C$_{0-4}$alkyl)$_2$, —C$_{0-4}$ alkyl-S—C$_{0-4}$alkyl-thiadiazolyl(C$_{0-4}$alkyl), —C$_{0-4}$alkyl-S—C$_{0-4}$alkyl-diazolyl(C$_{0-4}$alkyl), —C$_{0-4}$alkyl-S—C$_{1-4}$ alkyl-Si(C$_{0-4}$alkyl)$_3$, —C$_{0-4}$alkyl-S—C$_{0-4}$alkyl-phenyl(C$_{0-4}$ alkyl), —C$_{0-4}$alkyl-S—C$_{0-4}$alkyl-C(O)—C$_{0-4}$alkyl-O—C$_{0-4}$ alkyl, or —C$_{0-4}$alkyl-S—C$_{0-4}$alkyl-C$_{3-6}$cycloalkyl-C$_{0-4}$ alkyl-C(O)—C$_{0-4}$alkyl-O—C$_{0-4}$alkyl, wherein any alkyl, cycloalkyl, alkenyl, phenyl, or pyridyl are each optionally substituted with 1–9 independently halogen, hydroxyl, —C$_{0-4}$alkyl-O—C$_{1-6}$alkyl, or —C$_{0-4}$alkyl-S—C$_{1-6}$alkyl;

optionally, R$_2$ forms =O with an adjoining bond;

R$_4$ is hydrogen, or halogen; and any ring nitrogen optionally forms N-oxide or N-chloride.

In an embodiment of this one aspect, the compound of this invention is, represented by Formula (I), or a pharmaceutically acceptable salt thereof, wherein A is C;

X is phenyl;

R$_1$ is hydrogen, halogen; or —C$_{1-6}$alkyl, -cycloC$_{3-6}$alkyl, or —C$_{1-6}$alkenyl group, wherein any of the groups is optionally substituted with 1–6 substituents; wherein each substituent is independently halogen, —OH, —CN, or —SO$_2$—C$_{1-6}$alkyl;

R$_2$, and R$_3$ are each independently hydrogen, halogen, hydroxyl, —CN, —NO$_2$; or —C$_{1-6}$alkyl, —C$_{2-6}$alkenyl, —C$_{1-6}$alkyl(C$_{2-6}$alkenyl)$_2$, —C$_{0-4}$alkyl(C$_{3-6}$cycloalkyl)$_2$, —C$_{0-6}$alkyl-N(C$_{0-6}$alkyl)$_2$, —C$_{0-4}$alkyl-O—C$_{1-6}$alkyl, —C$_{1-6}$alkyl-phenyl, —C$_{0-6}$alkyl-SO$_2$—C$_{1-6}$alkyl, C$_{0-6}$alkyl-C(O)—C$_{0-4}$alkyl, —C$_{0-6}$alkyl-C(O)—C$_{0-6}$alkyl-phenyl, —C$_{0-6}$alkyl-C(O)—C$_{0-4}$alkyl-O—C$_{0-6}$alkyl, —C$_{0-6}$alkyl-C(O)—C$_{0-6}$alkyl-O—C$_{0-6}$alkyl-O—C$_{0-6}$alkyl-C(O)—C$_{0-6}$alkyl, —C$_{2-6}$alkenyl-C(O)—C$_{0-4}$alkyl-O—C$_{0-6}$ alkyl, —C$_{0-4}$alkyl-C$_{3-6}$cycloalkyl-C$_{0-6}$alkyl-C(O)—C$_{0-6}$alkyl, —C$_{0-4}$alkyl-C$_{3-6}$cycloalkyl-C$_{0-6}$alkyl-C(O)—C$_{0-6}$alkyl-N(C$_{0-6}$alkyl)$_2$, —C$_{0-4}$alkyl-C$_{3-6}$cycloalkyl-C$_{0-6}$alkyl-C(O)—C$_{0-4}$alkyl-O—C$_{0-6}$alkyl, —C$_{2-6}$alkenyl-C(O)—C$_{0-4}$alkyl-N(C$_{0-6}$alkyl)-pyridyl, —C$_{0-6}$alkyl-C(O)—C$_{0-4}$alkyl-N(C$_{0-4}$alkyl)$_2$, —C$_{0-6}$alkyl-C(O)—C$_{0-4}$alkyl-N(C$_{0-4}$alkyl)—C$_{3-6}$cycloalkyl, —C$_{2-6}$alkenyl-C(O)—C$_{0-4}$alkyl-N(C$_{0-4}$ alkyl)-C$_{3-6}$cycloalkyl, —SO$_2$—C$_{0-6}$alkyl-phenyl, —SO$_2$—C$_{0-6}$alkyl-(—C$_{0-6}$alkyl-phenyl)(—C$_{0-6}$alkyl-phenyl), —C$_{0-4}$alkyl-SO$_2$—C$_{0-4}$alkyl-C$_{3-6}$cycloalkyl-C$_{0-4}$ alkyl-C(O)—C$_{0-4}$ alkyl-O—C$_{0-4}$alkyl, —S(O)—C$_{0-6}$alkyl, —P(O)(O—C$_{0-4}$ alkyl)(O—C$_{0-4}$alkyl), —C$_{2-6}$alkenyl-C(O)—C$_{0-4}$alkyl-N(C$_{0-4}$alkyl)-pyridyl, —S—C$_{1-6}$alkyl, —C$_{0-6}$alkyl-N(C$_{0-6}$alkyl)—C(O)—C$_{0-6}$alkyl, —C$_{0-6}$alkyl-N(C$_{0-6}$alkyl)-C(O)—N(C$_{0-6}$alkyl)$_2$, —C$_{0-4}$alkyl-S—$_{1-4}$alkyl-oxadiazolyl(C$_{0-4}$alkyl), —C$_{0-4}$alkyl-C(O)—C$_{0-4}$alkyl-phenyl, —C$_{0-4}$alkyl-O—C$_{0-4}$alkyl-phenyl, —C$_{0-4}$alkyl-C$_{3-6}$cycloalkyl-C$_{0-4}$ alkyl-tetrazolyl, —SO$_2$—N(C$_{0-4}$alkyl)$_2$, —C$_{0-4}$alkyl-S—C$_{0-4}$alkyl-thiadiazolyl(C$_{0-4}$alkyl), —C$_{0-4}$alkyl-S—C$_{0-4}$alkyl-diazolyl(C$_{0-4}$alkyl), C$_{0-4}$alkyl-S—C$_{1-4}$alkyl-Si(C$_{0-4}$alkyl)$_3$, —C$_{0-4}$alkyl-S—C$_{0-4}$alkyl-phenyl(C$_{0-4}$alkyl), —C$_{0-4}$ alkyl-S—C$_{0-4}$alkyl-C(O)—C$_{0-4}$alkyl-O—C$_{0-4}$alkyl, or —C$_{0-4}$alkyl-S—C$_{0-4}$alkyl-C$_{3-6}$cycloalkyl-C$_{0-4}$alkyl-C(O)—C$_{0-4}$alkyl-O—C$_{0-4}$alkyl, wherein any alkyl, cycloalkyl, alkenyl, phenyl, or pyridyl are each optionally substituted with 1–9 independently halogen, hydroxyl, —C$_{0-4}$alkyl-O—C$_{1-6}$alkyl, or C$_{0-4}$alkyl-S—C$_{1-6}$alkyl;

optionally, R$_2$ forms =O with an adjoining bond;

R$_4$ is hydrogen, or halogen; and any ring nitrogen optionally forms N-oxide or N-chloride.

In another embodiment of this one aspect, the compound of this invention is represented by Formula (I), or a pharmaceutically acceptable salt thereof, wherein A is C;

X is thiaphenyl;

R$_1$ is hydrogen, halogen; or —C$_{1-6}$alkyl, -cycloC$_{3-6}$alkyl, or —C$_{1-6}$alkenyl group, wherein any of the groups is optionally substituted with 1–6 substituents; wherein each substituent is independently halogen, —OH, —CN, or —SO$_2$—C$_{1-6}$alkyl;

R$_2$, and R$_3$ are each independently hydrogen, halogen, hydroxyl, —CN, —NO$_2$; or —C$_{1-6}$alkyl, —C$_{2-6}$alkenyl, —C$_{1-6}$alkyl(C$_{2-6}$alkenyl)$_2$, —C$_{0-4}$alkyl(C$_{3-6}$cycloalkyl)$_2$, —C$_{0-6}$alkyl-N(C$_{0-6}$alkyl)$_2$, —C$_{0-4}$alkyl-O—C$_{1-6}$alkyl, —C$_{1-6}$alkyl-phenyl, —C$_{0-6}$alkyl-SO$_2$—C$_{1-6}$alkyl, —C$_{0-6}$alkyl-C(O)—C$_{0-4}$alkyl, —C$_{0-6}$alkyl-C(O)—C$_{0-6}$alkyl-phenyl, C$_{0-6}$alkyl-C(O)—C$_{0-4}$alkyl-O—C$_{0-6}$alkyl, —C$_{0-6}$alkyl-C(O)—C$_{0-6}$alkyl-O—C$_{0-6}$alkyl-O—C$_{0-6}$alkyl-C(O)—C$_{0-6}$alkyl, —C$_{2-6}$alkenyl-C(O)—C$_{0-4}$alkyl-O—C$_{0-6}$alkyl, -C$_{0-4}$alkyl-C$_{3-6}$cycloalkyl-C$_{0-6}$alkyl-C(O)—C$_{0-6}$alkyl, —C$_{0-4}$alkyl-C$_{3-6}$cycloalkyl-C$_{0-6}$alkyl-C(O)—C$_{0-6}$alkyl-N(C$_{0-6}$alkyl)$_2$, —C$_{0-4}$alkyl-C$_{3-6}$cycloalkyl-C$_{0-6}$alkyl-C(O)—C$_{0-4}$ alkyl-O—C$_{0-4}$alkyl, —C$_{2-6}$alkenyl-C(O)—C$_{0-4}$alkyl-N(C$_{0-6}$ alkyl)-pyridyl, —C$_{0-6}$alkyl-C(O)—C$_{0-4}$alkyl-N(C$_{0-4}$alkyl)$_2$, —C$_{0-6}$alkyl-C(O)—C$_{0-4}$alkyl-N(C$_{0-4}$alkyl)—C$_{3-6}$cycloalkyl, —C$_{2-6}$alkenyl-C(O)—C$_{0-4}$alkyl-N(C$_{0-4}$alkyl)-C$_{3-6}$cycloalkyl, —SO$_2$—C$_{0-6}$alkyl-phenyl, —SO$_2$—C$_{0-6}$alkyl-(—C$_{0-6}$alkyl-phenyl)(—C$_{0-6}$alkyl-phenyl), —C$_{0-4}$alkyl-SO$_2$—C$_{0-4}$alkyl-C$_{3-6}$cycloalkyl-C$_{0-4}$alkyl-C(O)—C$_{0-4}$ alkyl-O—C$_{0-4}$alkyl, —S(O)—C$_{0-6}$alkyl, —P(O)(O—C$_{0-4}$ alkyl)(O—C$_{0-4}$alkyl), —C$_{2-6}$alkenyl-C(O)—C$_{0-4}$alkyl-N(C$_{0-4}$alkyl)-pyridyl, —S—$_{1-6}$alkyl, —C$_{0-6}$alkyl-N(C$_{0-6}$alkyl)-C(O)—C$_{0-6}$alkyl, —C$_{0-6}$alkyl-N(C$_{0-6}$alkyl)-C(O)—N(C$_{0-6}$alkyl)$_2$, —C$_{0-4}$alkyl-S—C$_{1-4}$alkyl-oxadiazolyl(C$_{0-4}$alkyl), —C$_{0-4}$alkyl-C(O)—C$_{0-4}$alkyl-phenyl, —C$_{0-4}$alkyl-O—C$_{0-4}$alkyl-phenyl, —C$_{0-4}$alkyl-C$_{3-6}$cycloalkyl-C$_{0-4}$alkyl-tetrazolyl, —SO$_2$—N(C$_{0-4}$alkyl)$_2$, —C$_{0-4}$alkyl-S—C$_{0-4}$alkyl-thiadiazolyl(C$_{0-4}$alkyl), —C$_{0-4}$alkyl-S—C$_{0-4}$alkyl-diazolyl(C$_{0-4}$alkyl), —C$_{0-4}$alkyl-S—C$_{1-4}$alkyl-Si(C$_{0-4}$alkyl)$_3$, —C$_{0-4}$alkyl-S—C$_{0-4}$alkyl-phenyl(C$_{0-4}$alkyl), —C$_{0-4}$ alkyl-S—C$_{0-4}$alkyl-C(O)—C$_{0-4}$alkyl-O—C$_{0-4}$alkyl, or —C$_{0-4}$alkyl-S—C$_{0-4}$alkyl-C$_{3-6}$cycloalkyl-C$_{0-4}$alkyl-C(O)—C$_{0-4}$alkyl-O—C$_{0-4}$alkyl, wherein any alkyl, cycloalkyl, alkenyl, phenyl, or pyridyl are each optionally substituted with 1–9 independently halogen, hydroxyl, —C$_{0-4}$alkyl-O—C$_{1-6}$alkyl, or —C$_{0-4}$alkyl-S—C$_{1-6}$alkyl;

optionally, R$_2$ forms =O with an adjoining bond;

R$_4$ is hydrogen, or halogen; and any ring nitrogen optionally forms N-oxide or N-chloride.

In still another embodiment of this one aspect, the compound of this invention is represented by Formula (I), or a pharmaceutically acceptable salt thereof, wherein A is C;

X is benzofuranyl;

R$_1$ is hydrogen, halogen; or —C$_{1-6}$alkyl, -cycloC$_{3-6}$alkyl, or —C$_{1-6}$alkenyl group, wherein any of the groups is optionally substituted with 1–6 substituents; wherein each substituent is independently halogen, —OH, —CN, or —SO$_2$—C$_{1-6}$alkyl;

R$_2$, and R$_3$ are each independently hydrogen, halogen, hydroxyl, —CN, —NO$_2$; or —C$_{1-6}$alkyl, —C$_{2-6}$alkenyl, —C$_{1-6}$alkyl(C$_{2-6}$alkenyl)$_2$, —C$_{0-4}$alkyl(C$_{3-6}$cycloalkyl)$_2$, —C$_{0-6}$alkyl-N(C$_{0-6}$alkyl)$_2$, —C$_{0-4}$alkyl-O—C$_{1-6}$alkyl, —C$_{1-6}$alkyl-phenyl, —C$_{0-6}$alkyl-SO$_2$—C$_{1-6}$alkyl, —C$_{0-6}$alkyl-C(O)—C$_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, —$C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$alkyl-C(O)—$C_{0-6}$alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl,
—$C_{2-6}$ alkenyl-C(O)—$C_{0-4}$alkyl-N($C_{0-6}$alkyl)-pyridyl, —$C_{0-6}$ alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)—$C_{3-6}$cycloalkyl, —$C_{2-6}$alkenyl-C(O)—$C_{0-4}$alkyl-N($C_{0-4}$alkyl)—$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$alkyl-O—$C_{0-4}$alkyl,
—S(O)—$C_{0-6}$alkyl, —P(O)(O—$C_{0-4}$alkyl)(O—$C_{0-4}$alkyl), —$C_{2-6}$alkenyl-C(O)—$C_{0-4}$alkyl-N($C_{0-4}$alkyl)-pyridyl, —S—$C_{1-6}$alkyl, $C_{0-6}$alkyl-N($C_{0-6}$alkyl)—C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, $C_{0-4}$alkyl-O—$C_{0-4}$alkyl-phenyl, —$C_{0-4}$alkyl-$C_{3-6}$cycloalkyl-$C_{0-4}$alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$alkyl-diazolyl($C_{0-4}$alkyl), —$C_{0-4}$ alkyl-S—$C_{1-4}$alkyl-Si($C_{0-4}$alkyl)$_3$, —$C_{0-4}$alkyl-S—$C_{0-4}$ alkyl-phenyl($C_{0-4}$alkyl), —$C_{0-4}$alkyl-S—$C_{0-4}$alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In yet another embodiment of this one aspect, the compound of this invention is represented by Formula (I), or a pharmaceutically acceptable salt thereof, wherein A is C;

X is pyridyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, $C_{0-4}$alkyl-$C_{3-6}$cycloalkyl-$C_{0-6}$alkyl-C(O)—$C_{0-6}$alkyl,
—$C_{0-4}$ alkyl-$C_{3-6}$cycloalkyl-$C_{0-6}$alkyl-C(O)—$C_{0-6}$alkyl-N ($C_{0-6}$ alkyl)$_2$, $C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)-pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)-$C_{3-6}$cycloalkyl, —$C_{2-6}$alkenyl-C(O)—$C_{0-4}$alkyl-N($C_{0-4}$alkyl)-$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$alkyl-O—$C_{0-4}$alkyl, —$C_{0-4}$ alkyl-O—$C_{0-4}$alkyl, —S(O)—$C_{0-6}$alkyl, —P(O)(O—$C_{0-4}$ alkyl)(O—$C_{0-4}$alkyl), —$C_{2-6}$alkenyl-C(O)—$C_{0-4}$alkyl-N($C_{0-4}$alkyl)-pyridyl, —S—$_{1-6}$alkyl, —$C_{0-6}$alkyl-N($C_{0-6}$alkyl)-C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$_{1-4}$alkyl-oxadiazolyl($C_{0-4}$alkyl), —$C_{0-4}$alkyl-C(O) $C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$ alkyl-tetrazolyl, —$SO_2$—N($C_{0-4}$alkyl)$_2$, —$C_{0-6}$alkyl-S—$C_{0-4}$alkyl-thiadiazolyl($C_{0-4}$alkyl), —$C_{0-4}$alkyl-S—$C_{0-4}$ alkyl-diazolyl($C_{0-4}$alkyl), —$C_{0-4}$alkyl-S—$C_{1-4}$alkyl-Si($C_{0-4}$alkyl)$_3$, —$C_{0-4}$alkyl-S—$C_{0-4}$alkyl-phenyl($C_{0-4}$alkyl), —$C_{0-4}$ alkyl-S—$C_{0-4}$alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-6}$alkyl-O—$C_{1-6}$alkyl, or —$C_{0-4}$alkyl-S—$C_{1-6}$alkyl;

$R_4$ is hydrogen, or halogen; and any ring nitrogen optionally forms N-oxide or N-chloride.

In yet still another embodiment of this one aspect, the compound of this invention is represented by Formula (I), or a pharmaceutically acceptable salt thereof, wherein A is C;

X is pyridyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_3$ is hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$ alkyl-C(O)—$C_{0-6}$alkyl-phenyl, —$C_{0-6}$alkyl-C(O)—$C_{0-4}$ alkyl-O—$C_{0-6}$alkyl, —$C_{0-6}$alkyl-C(O)—$C_{0-6}$alkyl-O—$C_{0-6}$ alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, —$C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$ alkyl-C(O)—$C_{0-6}$alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl,
—$C_{2-6}$ alkenyl-C(O)—$C_{0-4}$alkyl-N($C_{0-6}$alkyl)-pyridyl, —$C_{0-6}$ alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)-$C_{3-6}$cycloalkyl, —$C_{2-6}$alkenyl-C(O)—$C_{0-4}$alkyl-N($C_{0-4}$alkyl)-$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$alkyl-O—$C_{0-4}$alkyl, —S(O)—$C_{0-6}$alkyl, —P(O)(O—$C_{0-4}$alkyl)(O—$C_{0-4}$alkyl), —$C_{2-6}$alkenyl-C(O)—$C_{0-4}$alkyl-N($C_{0-4}$alkyl)-pyridyl, —S—$C_{1-6}$alkyl, —$C_{0-6}$alkyl-N($C_{0-6}$alkyl)-C(O)—$C_{0-6}$ alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$ alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$alkyl-diazolyl($C_{0-4}$ alkyl), —$C_{0-4}$alkyl-S—$C_{1-4}$alkyl-Si($C_{0-4}$alky)$_3$, —$C_{0-4}$ alkyl-S—$C_{0-4}$alkyl-phenyl($C_{0-4}$alkyl), —$C_{0-4}$alkyl-S—$C_{0-4}$ alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

$R_2$ forms =O with an adjoining bond;

$R_4$ is hydrogen, or halogen; and any ring nitrogen optionally forms N-oxide or N-chloride.

In still another embodiment of this one aspect, the compound of this invention is represented by Formula (I), or a pharmaceutically acceptable salt thereof, wherein A is C;

X is quinolinyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, —$C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$alkyl-C(O)—$C_{0-6}$alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)-$C_{3-6}$cycloalkyl, —$C_{2-6}$alkenyl-C(O)—$C_{0-4}$alkyl-N($C_{0-4}$alkyl)-$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$ alkyl-O—$C_{0-4}$alkyl, —S(O)—$C_{0-6}$alkyl, —P(O)(O—$C_{0-4}$ alkyl)(O—$C_{0-4}$alkyl), —$C_{2-6}$alkenyl-C(O)—$C_{0-4}$alkyl-N($C_{0-4}$alkyl)pyridyl, —S—$C_{1-6}$alkyl, —$C_{0-6}$alkyl-N($C_{0-6}$alkyl)-C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$alkyl-diazolyl($C_{0-4}$alkyl), —$C_{0-4}$alkyl-S—$C_{1-4}$alkyl-Si($C_{0-4}$alkyl)$_3$, —$C_{0-4}$alkyl-S—$C_{0-4}$alkyl-phenyl($C_{0-4}$alkyl), —$C_{0-4}$ alkyl-S—$C_{0-4}$alkyl-C(O)—$C_{0-4}$alkyl-O-$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In still another embodiment of this one aspect, the compound of this invention is represented by Formula (I), or a pharmaceutically acceptable salt thereof, wherein A is C;

X is oxadiazolyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, —$C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$alkyl-C(O)—$C_{0-6}$ alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)-pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)—$C_{3-6}$cycloalkyl, —$C_{2-6}$alkenyl-C(O)—$C_{0-4}$alkyl-N($C_{0-4}$alkyl)—$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$ alkyl-O—$C_{0-4}$alkyl, —S(O)—$C_{0-6}$alkyl, —P(O)(O—$C_{0-4}$ alkyl)(O—$C_{0-4}$alkyl), —$C_{2-6}$alkenyl-C(O)—$C_{0-4}$alkyl-N($C_{0-4}$alkyl)-pyridyl, —S—$C_{1-6}$alkyl, —$C_{0-6}$alkyl-N($C_{0-6}$alkyl)-C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$ alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$ alkyl-diazolyl($C_{0-4}$alkyl), —$C_{0-4}$alkyl-S—$C_{1-4}$alkyl-Si($C_{0-4}$alkyl)$_3$, —$C_{0-4}$alkyl-S—$C_{0-4}$alkyl-phenyl($C_{0-4}$alkyl), —$C_{0-4}$ alkyl-S—$C_{0-4}$alkyl-C(O)—$C_{0-4}$alkyl-O-$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$ alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In yet another embodiment of this one aspect, the compound of this invention is represented by Formula (I), or a pharmaceutically acceptable salt thereof, wherein A is C;

X is diazolylpyridinyl or imidazolylpyridinyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, N, or —$SO_2$—$C_{1-6}$ alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, $C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$ alkyl, —$C_{2-6}$alkenyl-C(O)—$C_{0-4}$alkyl-O—$C_{0-6}$alkyl, —$C_{0-4}$ alkyl-$C_{3-6}$cycloalkyl-$C_{0-6}$alkyl-C(O)—$C_{0-6}$alkyl-$C_{0-4}$ alkyl-$C_{3-6}$cycloalkyl-$C_{0-6}$alkyl-C(O)—$C_{0-6}$alkyl-N($C_{0-6}$ alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)—$C_{3-6}$cycloalkyl, —$C_{2-6}$alkenyl-C(O)—$C_{0-4}$alkyl-N($C_{0-4}$alkyl)—$C_{3-6}$cycloalkyl, —$SO_2$—$C_{0-6}$alkyl-phenyl, —$SO_2$$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$ alkyl-O—$C_{0-4}$alkyl, —S(O)—$C_{0-6}$alkyl, —P(O)(O—$C_{0-4}$ alkyl)(O—$C_{0-4}$alkyl), —$C_{2-6}$alkenyl-C(O)—$C_{0-4}$alkyl-N ($C_{0-4}$alkyl)-pyridyl, —S—$C_{1-6}$alkyl, —$C_{0-6}$alkyl-N($C_{0-6}$ alkyl)-C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$ alkyl), —$C_{0-4}$alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$ alkyl-tetrazolyl, —$SO_2$—N($C_{0-4}$alkyl)$_2$, —$C_{0-4}$alkyl-S—$C_{0-4}$alkyl-thiadiazolyl ($C_{0-4}$alkyl), $C_{0-4}$alkyl-S —$C_{0-4}$alkyl-diazolyl($C_{0-4}$alkyl), $C_{0-4}$alkyl-S—$C_{1-4}$alkyl-Si $(C_{0-4}alkyl)_3$, —$C_{0-4}alkyl$-S—$C$-$_{0-4}alkyl$-phenyl$(C_{0-4}alkyl)$, —$C_{0-4}alkyl$-S—$C_{0-4}alkyl$-C(O)—$C_{0-4}alkyl$-O—$C_{0-4}alkyl$, or —$C_{0-4}alkyl$-S—$C_{0-4}alkyl$-$C_{3-6}cycloalkyl$-$C_{0-4}alkyl$-C(O)—$C_{0-4}alkyl$-O—$C_{0-4}alkyl$, wherein any alkyl, cycloalkyl, alkenyl, phenyl, or pyridyl are each optionally substituted with 1–9 independently halogen, hydroxyl, —$C_{0-4}alkyl$-O—$C_{1-6}alkyl$, or $C_{0-4}alkyl$-S—$C_{1-6}alkyl$;

optionally, $R_2$ forms =O with an adjoining bond;

$R_4$ is hydrogen, or halogen; and any ring nitrogen optionally forms N-oxide or N-chloride.

In still another embodiment of this one aspect, the compound of this invention is represented by Formula (1), or a pharmaceutically acceptable salt thereof, wherein A is C;

X is pyrazinyl;

$R_1$ is hydrogen, halogen; or —$C_{1-6}alkyl$, -cyclo$C_{3-6}alkyl$; or —$C_{1-6}alkenyl$ group, wherein any of the groups is optionally substituted with 1–6 substituents; wherein each substituent is independently halogen, —OH, —CN, or —$SO_2$—$C_{1-6}alkyl$;

$R_2$, and $R_3$ are each independently hydrogen, halogen, hydroxyl, —CN, —$NO_2$; or —$C_{1-6}alkyl$, —$C_{2-6}alkenyl$, —$C_{1-6}alkyl(C_{2-6}alkenyl)_2$, —$C_{0-4}alkyl(C_{3-6}cycloalkyl)_2$, —$C_{0-6}alkyl$-N$(C_{0-6}alkyl)_2$, —$C_{0-4}alkyl$-O—$C_{1-6}alkyl$, —$C_{1-6}alkyl$-phenyl, —$C_{0-6}alkyl$-$SO_2$—$C_{1-6}alkyl$, —$C_{0-6}alkyl$-C(O)—$C_{0-4}alkyl$, —$C_{0-6}alkyl$-C(O)—$C_{0-6}alkyl$-phenyl, —$C_{0-6}alkyl$-C(O)—$C_{0-4}alkyl$-O—$C_{0-6}alkyl$, —$C_{0-6}alkyl$-C(O)—$C_{0-6}alkyl$-O—$C_{0-6}alkyl$-O—$C_{0-6}alkyl$-C(O)—$C_{0-6}alkyl$, —$C_{2-6}alkenyl$-C(O)—$C_{0-4}alkyl$-O—$C_{0-6}$ alkyl, —$C_{0-4}alkyl$-$C_{3-6}cycloalkyl$-$C_{0-6}alkyl$-C(O)—$C_{0-6}$ alkyl, —$C_{0-4}alkyl$-$C_{3-6}cycloalkyl$-$C_{0-6}alkyl$-C(O)—$C_{0-6}$ alkyl-N$(C_{0-6}alkyl)_2$, —$C_{0-4}alkyl$-$C_{3-6}cycloalkyl$-$C_{0-6}alkyl$-C(O)—$C_{0-4}alkyl$-O—$C_{0-6}alkyl$, —$C_{2-6}alkenyl$-C(O)—$C_{0-4}$ alkyl-N$(C_{0-6}alkyl)$pyridyl, —$C_{0-6}alkyl$-C(O)—$C_{0-4}alkyl$-N$(C_{0-4}alkyl)_2$, —$C_{0-6}alkyl$-C(O)$C_{0-4}alkyl$-N$(C_{0-4}alkyl)$—$C_{3-6}cycloalkyl$, —$C_{2-6}alkenyl$-C(O)—$C_{0-4}alkyl$-N$(C_{0-4}alkyl)$—$C_{3-6}cycloalkyl$, —$SO_2$—$C_{0-6}alkyl$-phenyl, —$SO_2$—$C_{0-6}alkyl$-(—$C_{0-6}alkyl$-phenyl)(—$C_{0-6}alkyl$-phenyl), —$C_{0-4}alkyl$-$SO_2$—$C_{0-4}alkyl$-$C_{3-6}cycloalkyl$-$C_{0-4}alkyl$-C(O)—$C_{0-4}$ alkyl-O—$C_{0-4}alkyl$, —S(O)—$C_{0-6}alkyl$, —P(O)(O—$C_{0-4}$ alkyl)(O—$C_{0-4}alkyl$), —$C_{2-6}alkenyl$-C(O)—$C_{0-4}alkyl$-N$(C_{0-4}alkyl)$pyridyl, —S—$_{1-6}alkyl$, —$C_{0-6}alkyl$-N$(C_{0-6}alkyl)$—C(O)—$C_{0-6}alkyl$-$C_{0-6}alkyl$-N$(C_{0-6}alkyl)$—C(O)—N$(C_{0-6}alkyl)_2$, —$C_{0-4}alkyl$-S—$C_{1-4}alkyl$-oxadiazolyl$(C_{0-4}alkyl)$, —$C_{0-4}alkyl$-C(O)—$C_{0-4}alkyl$-phenyl, —$C_{0-4}alkyl$-O—$C_{0-4}alkyl$-phenyl, —$C_{0-4}alkyl$-$C_{3-6}cycloalkyl$-$C_{0-4}alkyl$-tetrazolyl, $SO_2$—N$(C_{0-4}alkyl)_2$, —$C_{0-4}alkyl$-S—$C_{0-4}$ alkyl-thiadiazolyl$(C_{0-4}$ alkyl),—$C_{0-4}alkyl$-S—$C_{0-4}alkyl$-diazolyl$(C_{0-4}alkyl)$,—$C_{0-4}alkyl$-S—S—$C_{1-4}alkyl$-Si$(X_{0-4}$ alkyl)$_3$, —$C_{0-4}alkyl$-S—$C_{0-4}alkyl$-phenyl$(C_{0-4}alkyl)$, —$C_{0-4}$ alkyl-S—$C_{0-4}alkyl$-C(O)—$C_{0-4}alkyl$-O—$C_{0-4}alkyl$, or —$C_{0-4}alkyl$-S—$C_{0-4}alkyl$-$C_{3-6}cycloalkyl$-$C_{0-4}alkyl$-C(O)—$C_{0-4}alkyl$-O—$C_{0-4}alkyl$,wherein any alkyl, cycloalkyl, alkenyl, phenyl, or pyridyl are each optionally substituted with 1–9 independently halogen, hydroxyl, —$C_{0-4}alkyl$-O—$C_{1-6}alkyl$, or —$C_{0-4}alkyl$-S—$C_{1-6}alkyl$;

optionally, $R_2$ forms =O with an adjoining bond;

$R_4$ is hydrogen, or halogen; and any ring nitrogen optionally forms N-oxide or N-chloride.

In yet still another embodiment of this one aspect, the compound of this invention is represented by Formula (I), or a pharmaceutically acceptable salt thereof, wherein A is C;

X is oxadiazolylphenyl;

$R_1$ is hydrogen, halogen; or $C_{1-6}alkyl$, -cyclo$C_{3-6}alkyl$, or —$C_{1-6}alkenyl$ group, wherein any of the groups is optionally substituted with 1–6 substituents; wherein each substituent is independently halogen, —OH, —CN, or —$SO_2$—$C_{1-6}$ alkyl;

$R_2$, and $R_3$ are each independently hydrogen, halogen, hydroxyl, —CN, —$NO_2$; or —$C_{1-6}alkyl$, —$C_{2-6}alkenyl$, —$C_{1-6}alkyl(C_{2-6}alkenyl)_2$, —$C_{0-4}alkyl(C_{3-6}cycloalkyl)_2$, —$C_{0-6}alkyl$-N$(C_{0-6}alkyl)_2$, —$C_{0-4}alkyl$-O—$C_{1-6}alkyl$, —$C_{1-6}alkyl$-phenyl, —$C_{0-6}alkyl$-$SO_2$—$C_{1-6}alkyl$, —$C_{0-6}alkyl$-C(O)—$C_{0-4}alkyl$, —$C_{0-6}alkyl$-C(O)—$C_{0-6}alkyl$-phenyl, —$C_{0-6}alkyl$-C(O)—$C_{0-4}alkyl$-O—$C_{0-6}alkyl$, —$C_{0-6}alkyl$-C(O)—$C_{0-6}alkyl$-O—$C_{0-6}alkyl$-O—$C_{0-6}alkyl$-C(O)$C_{0-6}$ alkyl, —$C_{2-6}alkenyl$-C(O)—$C_{0-4}alkyl$-O—$C_{0-6}alkyl$, —$C_{0-4}$ alkyl-$C_{3-6}cycloalkyl$-$C_{0-6}alkyl$-C(O)—$C_{0-6}alkyl$, —$C_{0-4}$ alkyl-$C_{3-6}cycloalkyl$-$C_{0-6}alkyl$-C(O)—$C_{0-6}alkyl$-N$(C_{0-6}$ alkyl)$_2$, —$C_{0-4}alkyl$-$C_{3-6}cycloalkyl$-$C_{0-6}alkyl$-C(O)—$C_{0-4}$ alkyl-O—$C_{0-6}alkyl$, —$C_{2-6}alkenyl$-C(O)—$C_{0-4}$ alkyl-N$(C_{0-6}alkyl)$-pyridyl, —$C_{0-6}alkyl$-C(O)—$C_{0-4}alkyl$-N$(C_{0-4}alkyl)_2$, —$C_{0-6}alkyl$-C(O)—$C_{0-4}alkyl$-N$(C_{0-4}alkyl)$—$C_{3-6}cycloalkyl$, —$C_{2-6}alkenyl$-C(O)$C_{0-4}alkyl$-N$(C_{0-4}$ alkyl)—$C_{3-6}cycloalkyl$, —$SO_2$—$C_{0-6}alkyl$-phenyl, —$SO_2$—$C_{0-6}alkyl$-(—$C_{0-6}alkyl$-phenyl)(—$C_{0-6}alkyl$-phenyl), —$C_{0-4}alkyl$-$SO_2$—$C_{0-4}alkyl$-$C_{3-6}cycloalkyl$ $C_{0-4}alkyl$-C(O)—$C_{0-4}alkyl$-O—$C_{0-4}alkyl$ —S(O)—$C_{0-6}alkyl$, —P(O)(O—$C_{0-4}$ alkyl)(O—$C_{0-4}alkyl$), —$C_{2-6}alkenyl$-C(O)—$C_{0-4}$ alkyl-N$(C_{0-4}alkyl)$-pyridyl, —S—$C_{1-6}alkyl$, —$C_{0-6}alkyl$-N$(C_{0-6}$ alkyl)-C(O)—$C_{0-6}alkyl$, —$C_{0-6}alkyl$-N$(C_{0-6}alkyl)$-C(O)—N$(C_{0-6}alkyl)_2$, —$C_{0-4}alkyl$-S—$C_{1-4}alkyl$-oxadiazolyl$(C_{0-4}$ alkyl), —$C_{0-4}alkyl$-C(O)—$C_{0-4}alkyl$-phenyl, —$C_{0-4}$ alkyl-O—$C_{0-4}alkyl$-phenyl, —$C_{0-4}alkyl$-$C_{3-6}cycloalkyl$-$C_{0-4}$ alkyl-tetrazolyl, —$SO_2$—N$(C_{0-4}alkyl)_2$, —$C_{0-4}alkyl$-S—$C_{0-4}alkyl$-thiadiazolyl$(C_{0-4}alkyl)$, —$C_{0-4}alkyl$-S—$C_{0-4}$ alkyl-diazolyl$(C_{0-4}alkyl)$, —$C_{0-4}alkyl$-S—$C_{0-4}alkyl$-Si$(C_{0-4}$ alkyl)$_3$, —$C_{0-4}alkyl$-S—$C_{0-4}alkyl$-phenyl$(C_{0-4}alkyl)$, —$C_{0-4}$ alkyl-S—$C_{0-4}alkyl$-C(O)$C_{0-4}alkyl$-O—$C_{0-4}alkyl$, or —$C_{0-4}$ alkyl-S—$C_{0-4}alkyl$-$C_{3-6}cycloalkyl$-$C_{0-4}alkyl$-C(O)—$C_{0-4}$ alkyl-O—$C_{0-4}alkyl$, wherein any alkyl, cycloalkyl, alkenyl, phenyl, or pyridyl are each optionally substituted with 1–9 independently halogen, hydroxyl, $C_{0-4}alkyl$-O—$C_{1-6}alkyl$ or —$C_{0-4}alkyl$-S—$_{1-6}alkyl$;

optionally, $R_2$ forms =O with an adjoining bond;

$R_4$ is hydrogen, or halogen; and any ring nitrogen optionally forms N-oxide or N-chloride, In even another embodiment of this one aspect, the compound of this invention is represented by Formula (I), or a pharmaceutically acceptable salt thereof, wherein.

A is C;

X is benzodioxolyl;

$R_1$ is hydrogen, halogen; or —$C_{1-6}alkyl$, -cyclo$C_{3-6}alkyl$, or —$C_{1-6}alkenyl$ group, wherein any of the groups is optionally substituted with 1–6 substituents; wherein each substituent is independently halogen, —OH, —CN, or —$SO_2$—$C_{1-6}alkyl$;

$R_2$, and $R_3$ are each independently hydrogen, halogen, hydroxyl, —CN, —$NO_2$; or —$C_{1-6}alkyl$, —$C_{2-6}alkenyl$, —$C_{1-6}alkyl(C_{2-6}alkenyl)_2$, —$C_{0-4}alkyl(C_{3-6}cycloalkyl)_2$, —$C_{0-6}alkyl$-N$(C_{0-6}alkyl)_2$, —$C_{0-4}alkyl$-O—$C_{1-6}alkyl$, —$C_{1-6}alkyl$-phenyl, —$C_{0-6}alkyl$-$SO_2$—$C_{1-6}alkyl$, —$C_{0-6}alkyl$-C(O)—$C_{0-4}alkyl$, —$C_{0-6}alkyl$-C(O)—$C_{0-6}alkyl$-phenyl, —$C_{0-6}alkyl$-C(O)—$C_{0-4}alkyl$-O—$C_{0-6}alkyl$-$C_{0-6}alkyl$-C(O)—$C_{0-6}alkyl$-O—$C_{0-6}alkyl$-O—$C_{0-6}alkyl$-C(O)$C_{0-6}$ alkyl, —$C_{2-6}alkenyl$-C(O)—$C_{0-4}alkyl$-O—$C_{0-6}alkyl$, —$C_{0-4}$ alkyl-$C_{3-6}cycloalkyl$-$C_{0-6}alkyl$-C(O)—$C_{0-6}alkyl$, —$C_{0-4}$ alkyl-$C_{3-6}cycloalkyl$-$C_{0-6}alkyl$-C(O)—$C_{0-6}alkyl$-N$(C_{0-6}$ alkyl)$_2$, —$C_{0-4}alkyl$-$C_{3-6}cycloalkyl$-$C_{0-6}alkyl$-C(O)—$C_{0-4}$ alkyl-O—$C_{0-6}alkyl$, —$C_{2-6}alkenyl$-C(O)—$C_{0-4}alkyl$-N$(C_{0-6}alkyl)$-pyridyl, —$C_{0-6}alkyl$-C(O)—$C_{0-4}alkyl$-N$(C_{0-4}alkyl)_2$, —$C_{0-6}alkyl$-C(O)—$C_{0-4}alkyl$-N$(C_{0-4}alkyl)$ —$C_{3-6}$cycloalkyl, $C_{2-6}$alkenyl-C(O)$C_{0-4}$alkyl-N($C_{0-4}$alkyl)—$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$ alkyl-O—$C_{0-4}$alkyl), —S(O)—$C_{0-6}$alkyl, —P(O)(O—$C_{0-4}$ alkyl)(O—$C_{0-4}$alkyl), $C_{2-6}$alkenyl-C(O)—$C_{0-4}$alkyl-N($C_{0-4}$ alkyl)-pyridyl, —S—$C_{1-6}$alkyl, —$C_{0-6}$ alkyl-N($C_{0-6}$ alkyl)—C(O)—$C_{0-6}$alkyl, —$C_{0-6}$alkyl-N($C_{0-6}$ alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$ alkyl-O—$C_{0-4}$alkyl-phenyl, —$C_{0-4}$alkyl-$C_{3-6}$ cycloalkyl-$C_{0-4}$ alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$ alkyl-S—$C_{0-4}$ alkyl-diazolyl($C_{0-4}$alkyl), —$C_{0-4}$alkyl-S—$C_{1-4}$alkyl-Si ($C_{0-4}$ alkyl)$_3$, —$C_{0-4}$alkyl-S—$C_{0-4}$alkyl-phenyl ($C_{0-4}$alkyl), $C_{0-4}$alkyl-S—$C_{0-4}$alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$ alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In a second aspect, the compound of this invention is represented by Formula (I, or a pharmaceutically acceptable salt thereof, wherein A is N;

X is phenyl, pyridyl, pyrazinyl, thiaphenyl, quinolinyl, benzofuranyl, oxadiazolyl, diazolylpyridinyl, imidazolylpyridinyl, oxadiazolylphenyl, or benzodioxolyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$ alkyl, —$C_{0-4}$alkyl-$C_{3-6}$cycloalkyl-$C_{0-6}$alkyl-C(O)-$C_{0-6}$ alkyl, —$C_{0-4}$ alkyl-$C_{3-6}$cycloalkyl-$C_{0-6}$alkyl-C(O)—$C_{0-6}$ alkyl-N($C_{0-6}$ alkyl)$_2$, —$C_{0-4}$alkyl-$C_{3-6}$cycloalkyl-$C_{0-6}$alkyl-C(O)—$C_{0-4}$ alkyl-O—$C_{0-6}$alkyl, —$C_{2-6}$alkenyl-C(O)—$C_{0-4}$alkyl-N($C_{0-6}$alkyl)-pyridyl, —$C_{0-6}$alkyl-C(O)$C_{0-4}$alkyl-N($C_{0-4}$ alkyl)$_2$, —$C_{0-6}$alkyl-C(O)—$C_{0-4}$alkyl-N($C_{0-4}$alkyl)—$C_{3-6}$ cycloalkyl, —$C_{2-6}$alkenyl(O)—$C_{0-4}$alkyl-N($C_{0-4}$alkyl)—$C_{3-6}$cycloalkyl, $SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$$C_{0-4}$alkyl-$C_{3-6}$cycloalkyl-$C_{0-4}$alkyl-C(O)$C_{0-4}$alkyl-O—$C_{0-4}$alkyl, —S(O)—$C_{0-6}$alkyl, —P(O)(O—$C_{0-4}$alkyl)(O—$C_{0-4}$alkyl), —$C_{2-6}$alkenyl-C(O)—$C_{0-4}$alkyl-N($C_{0-4}$alkyl) pyridyl, —S—$C_{1-6}$alkyl, —$C_{0-6}$alkyl-N($C_{0-6}$alkyl-C(O)—$C_{0-6}$alkyl, —$C_{0-6}$alkyl-N($C_{0-6}$alkyl)—C(O)—N($C_{0-6}$alkyl)$_2$, $C_{0-4}$alkyl-S—$C_{1-4}$alkyl-oxadiazolyl($C_{0-4}$ alkyl), —$C_{0-4}$alkyl-C(O)$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$ alkyl-tetrazolyl, $O_2$—N($C_{0-4}$alkyl)$_2$, —$C_{0-4}$alkyl-S—$C_{0-4}$ alkyl-thiadiazolyl($C_{0-4}$alkyl), —$C_{0-4}$alkyl-S—$C_{0-4}$alkyl-diazolyl ($C_{0-4}$alkyl), —$C_{0-4}$alkyl-S—$C_{1-4}$alkyl-Si($C_{0-4}$alkyl)$_3$, —$C_{0-4}$ alkyl-S—$C_{0-4}$alkyl-phenyl($C_{0-4}$alkyl), —$C_{0-4}$alkyl-S—$C_{0-4}$ alkyl-C(O)$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In an embodiment of the second aspect, the compound of this invention is represented by Formula (I), or a pharmaceutically acceptable salt thereof, wherein A is N;

X is phenyl;

$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;

$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_6$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$ alkyl, —$C_{2-6}$alkenyl-C(O)—$C_{0-4}$alkyl-O—$C_{0-6}$alkyl, —$C_{0-4}$ alkyl-$C_{3-6}$cycloalkyl-$C_{0-6}$alkyl-C(O)—$C_{0-6}$alkyl, —$C_{0-4}$ alkyl-$C_{3-6}$cycloalkyl-$C_{0-6}$alkyl-C(O)$C_{0-6}$alkyl-N ($C_{0-6}$ alkyl)$_2$, —$C_{0-4}$alkyl-$C_{3-6}$cycloalkyl-$C_{0-6}$alkyl-C(O) $C_{0-4}$ alkyl-O—$C_{0-6}$alkyl, —$C_{2-6}$alkenyl-C(O)—$C_{0-4}$alkyl-N ($C_{0-6}$alkyl)-pyridyl, —$C_{0-6}$alkyl-C(O)—$C_{0-4}$alkyl-N($C_{0-4}$ alkyl)$_2$, —$C_{0-6}$alkyl-C(O)$C_{0-4}$alkyl-N($C_{0-4}$alkyl)—$C_{3-6}$ cycloalkyl, $C_{2-6}$alkenyl-C(O)—$C_{0-4}$alkyl-N($C_{0-4}$alkyl)-$C_{3-6}$ cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$alkyl-O—$C_{0-4}$alkyl, —S(O)—$C_{0-6}$alkyl, —P(O)(O—$C_{0-4}$alkyl)(0—$C_{0-4}$alkyl), —$C_{2-6}$alkenyl-C(O)—$C_{0-4}$alkyl-N ($C_{0-4}$alkyl)-pyridyl, —S—$C_{1-6}$alkyl, —$C_{0-6}$alkyl-N($C_{0-6}$alkyl)—C(O)—$C_{0-6}$alkyl, —$C_{0-6}$alkyl-N($C_{0-6}$alkyl), -C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$ alkyl-O—$C_{0-4}$alkyl-phenyl, —$C_{0-4}$alkyl-$C_{0-4}$alkyl-$C_{3-6}$cycloalkyl-$C_{0-4}$alkyl-tetrazolyl, —$SO_2$—N($C_{0-4}$alkyl)$_2$, —$C_{0-4}$ alkyl-S—$C_{0-4}$alkyl-thiadiazolyl($C_{0-4}$alkyl), —$C_{0-4}$ alkyl-S—$C_{0-4}$alkyl-diazolyl($C_{0-4}$alkyl), —$C_{0-4}$alkyl-S—$C_{1-4}$ alkyl-Si($C_{0-4}$alkyl)$_3$, —$C_{0-4}$alkyl-S—$C_{0-4}$alkyl-phenyl ($C_{0-4}$ alkyl), —$C_{0-4}$alkyl-S—$C_{0-4}$alkyl-C(O)$C_{0-4}$alkyl-O—$C_{0-4}$ alkyl, or —$C_{0-4}$alkyl-S—$C_{0-4}$alkyl-$C_{3-6}$cycloalkyl-$C_{0-4}$ alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl;

optionally, $R_2$ forms =O with an adjoining bond;

$R_4$ is hydrogen, or halogen; and any ring nitrogen optionally forms N-oxide or N-chloride.

In one aspect, $R_2$, and $R_3$ are each independently hydrogen, halogen, hydroxyl, —CN, or —$NO_2$.

In another aspect, $R_2$, and $R_3$ are each independently —$C_{1-6}$alkyl, —$C_{2-6}$alkenyl, —$C_{1-6}$alkyl($C_{2-6}$alkenyl)$_2$, or —$C_{0-4}$alkyl($C_{3-6}$cycloalkyl)$_2$, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl.

In another aspect, $R_2$, and $R_3$ are each independently —$C_{0-6}$alkyl-N($C_{0-6}$alkyl)$_2$, —$C_{0-4}$alkyl-$C_{3-6}$cycloalkyl- $C_{0-6}$alkyl-C(O)—$C_{0-6}$alkyl-N($C_{0-6}$alkyl)$_2$, —$C_{2-6}$alkenyl-C(O)—$C_{0-4}$alkyl-N($C_{0-6}$alkyl)-pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)—$C_{3-6}$cycloalkyl, —$C_{2-6}$alkenyl-C(O)—$C_{0-4}$alkyl-N($C_{0-4}$alkyl)—$C_{3-6}$cycloalkyl—$C_{2-6}$alkenyl-C(O)—$C_{0-4}$alkyl-N($C_{0-4}$alkyl)pyridyl, —$C_{0-4}$alkyl-N($C_{0-6}$alkyl)—C(O)—$C_{0-6}$alkyl, —$C_{0-6}$alkyl-N($C_{0-6}$alkyl) C(O)—N($C_{0-6}$ alkyl)$_2$, or —SO$_2$—N($C_{0-4}$alkyl)$_2$, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$_{1-6}$alkyl.

In another aspect, $R_2$, and $R_3$ are each independently —$C_{0-6}$alkyl-SO$_2$—$C_{1-6}$alkyl, —SO$_2$—$C_{0-6}$alkyl-phenyl, —SO$_2$—$C_{0-6}$alkyl-(—$C_{0-6}$alkyl-phenyl)(—$C_{0-6}$alkyl-phenyl), —$C_{0-4}$alkyl-SO$_2$—$C_{0-4}$alkyl-$C_{3-6}$cycloalkyl-$C_{0-4}$alkyl-C(O)—$C_{0-4}$alkyl-O—$C_{0-4}$alkyl, —S(O)—$C_{0-6}$alkyl, —S—$C_{1-6}$alkyl, —$C_{0-4}$alkyl-S—$C_{1-4}$alkyl-oxadiazolyl ($C_{0-4}$ alkyl), —SO$_2$—N($C_{0-4}$alkyl)$_2$, —$C_{0-4}$alkyl-S—$C_{0-4}$alkyl-thiadiazolyl($C_{0-4}$alkyl), —$C_{0-4}$ alkyl-S—$C_{0-4}$alkyl-diazolyl($C_{0-4}$alkyl), —$C_{0-4}$alkyl-S—$_{1-4}$alkyl-Si($C_{0-4}$alkyl)$_3$, —$C_{0-4}$ alkyl-S—$C_{0-4}$alkyl-phenyl($C_{0-4}$alkyl), —$C_{0-4}$alkyl-S—$C_{0-4}$ alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$C_{1-6}$alkyl.

In an aspect, $R_2$ forms =O with an adjoining bond;

In another aspect, $R_2$ and $R_3$ are each independently —$C_{1-6}$alkyl-phenyl, —$C_{0-6}$alkyl-C(O)—$C_{0-6}$alkyl-phenyl, —$C_{2-6}$alkenyl-C(O)—$C_{0-4}$alkyl-N($C_{0-6}$alkyl)-pyridyl, —SO$_2$—$C_{0-6}$alkyl-phenyl, —SO$_2$—$C_{0-6}$alkyl-(—$C_{0-6}$alkyl-phenyl)(—$C_{0-6}$alkyl-phenyl), —$C_{2-6}$alkenyl-C(O)—$C_{0-4}$alkyl-N($C_{0-4}$alkyl)-pyridyl, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$alkyl-tetrazolyl, —$C_{0-4}$alkyl-S—$C_{0-4}$alkyl-thiadiazolyl($C_{0-4}$alkyl), —$C_{0-4}$alkyl-S—$C_{0-4}$alkyl-diazolyl ($C_{0-4}$alkyl), or —$C_{0-4}$alkyl-S—$C_{0-4}$alkyl-phenyl($C_{0-4}$alkyl), wherein any alkyl, cycloalkyl, alkenyl, phenyl, or pyridyl are each optionally substituted with 1–9 independently halogen, hydroxyl, —$C_{0-4}$alkyl-O—$C_{1-6}$alkyl, or —$C_{0-4}$alkyl-S—$_{1-6}$alkyl.

In another aspect, the present invention is directed to a method of enhancing cognition in a healthy subject comprising administering a safe cognition enhancing amount of a phosphodiesterase-4 inhibitor. In particular, this invention is directed to a method of enhancing memory, learning, retention, recall, awareness and judgement in health subjects comprising administering a safe and cognition enhancing amount of a phosphodiesterase-4 inhibitor. Within this aspect there is a method of enhancing cognition in a healthy subject comprising administering a safe, non-emetic, cognition enhancing amount of a phosphodiesterase-4 inhibitor For purposes of this application is defined as a subject with cognition in the normal range for the subjects age or other classification. Cognition of a healthy subject as well as cognition enhancement of the healthy subject is illustrated shown by testing the compounds in the Morris water maze as reported by McNamara and Skelton, *Psychobiology*, 1993, 21, 101–108. Further details of relevant methodology are described in WO 96/25948. Other assessments for measuring cognition enhancement include, but are not limited to the "T" Maze Test; Radial Arm Maze Test; Delayed Non-Match or Delayed Match Test; Passive Avoidance Procedure; 5 Choice Test, disclosed in WO 01/87281 A2, published Nov. 22, 2001.

For purposes of this specification, classes of healthy subjects includes juveniles, adults and seniors of average cognition; juveniles, adults and seniors of above average cognition; and juveniles, adults and seniors of below average cognition.

For purposes of this specification, juvenile human subjects is defined as a human subject less than 18 years of age. For purposes of this specification, adult human subject is defined as a human subject 18 years of age or older. Within this classification is a human adult 18 to 40 years of age. For purposes of this specification, senior human subjects is defined as a human subject 40 years of age or older. Within this classification is a human subject 55 years of age or older; 65 years of age or older; and 70 years of age or older.

As appreciated by those of skill in the art, beginning at about age 25, the cognition of the healthy human declines at a measurable and reproducible rates, as for example, measured by CAmbridge Neuropsychological Test Automated Battery (CANTAB, de Jager C A, Milwain E, Budge M. Early detection of isolated memory deficits in the elderly: the need for more sensitive neuropsychological tests. Psychol Med 2002 April; 32(3):483–91) or the Cognitive Drug Reseach Battery (CDR, Barker A, Jones R, Simpson P, Wesnes K. (1995). Scopolamine induced cognitive impairment as a predictor of cognitive decline in healthy elderly volunteers. International Journal of Geriatric Psychiatry 10: 1059–1062). Thus, by the time a human subject becomes a senior 40 years of age the decline in cognitive function has declined significant and would benefit from a method of memory enhancement.

As used herein, "alkyl" as well as other groups having the prefix "alkyl" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl. The term "aryloxy" unless specifically stated otherwise includes multiple ring systems as well as single ring systems such as, for example, phenyl or naphthyl, connected through the oxy connecting atom to the connecting site.

The term "$C_0$–$C_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The heteroatoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocyclo$C_{4-7}$alkyl" describes nonaryl heterocyclic compounds having 3–6 carbon atoms and one nitrogen atom forming the ring. Examples include azetidinyl, pyrrolidinyl, piperidinyl, and perhydroazepinyl.

Examples of aryl($C_{1-6}$)alkyl include, for example, phenyl ($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_1$–$C_4$alkyl, and —OC(O) NH$C_1$–$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.001 mg/kg to about 140 mg/kg of body weight per day are useful in the treatment of conditions such as i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient, amount of carrier material which may vary from about 5 to about 95 percent of the total composition. Unit dosage forms will generally contain between from about 0.01 mg to about 1000 mg of the active ingredient, typically 0.00 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, i) Pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome, ii) Gastrointestinal disorders such as ulcerative colitis, Crohn's disease, and hypersecretion of gastric acid, iii) Infectious diseases such as bacterial, fungal or viral induced sepsis or septic shock, endotoxic shock (and associated conditions such as laminitis and colic in horses), and septic shock, iv) Neurological disorders such as spinal cord trauma, head injury, neurogenic inflammation, pain, and reperfusion injury of the brain, v) Inflammatory disorders such as psoriatic arthritis, rheumatoid arthritis, ankylosing spondylitis, osteoarthritis, inflammation and cytokine-mediated chronic tissue degeneration, vi) Allergic disorders such as allergic rhinitis, allergic conjunctivitis, and eosinophilic granuloma, vii) Psychiatric disorders such as depression, memory impairment, and monopolar depression, viii) Neurodegenerative disorders such as Parkinson disease, Alzheimer's disease, acute and chronic multiple sclerosis, ix) Dermatological disorders such as psoriasis and other benign or malignant proliferative skin diseases, atopic dermatitis, and urticaria, x) Oncological diseases such as cancer, tumor growth and cancerous invasion of normal tissues, xi) Metabolic disorders such as diabetes insipidus, xii) Bone disorders such as osteoporosis, xiii) Cardiovascular disorders such as arterial restenosis, atherosclerosis, reperfusion injury of the myocardium, and xiv) Other disorders such as chronic glomerulonephritis, vernal conjunctivitis, transplant rejection and graft versus host disease, and cachexia—maladies that are amenable to amelioration through inhibition of the PDE4 isoenzyme and the resulting elevated cAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

Thus, for example, pulmonary disorders such as asthma, chronic bronchitis, chronic obstructive pulmonary disease (COPD), adult respiratory distress syndrome, infant respiratory distress syndrome, cough, chronic obstructive pulmonary disease in animals, adult respiratory distress syndrome, and infant respiratory distress syndrome can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Gastrointestinal disorders such as ulcerative colitis, Crohn's disease, and hypersecretion of gastric acid can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Infectious diseases such as bacterial, fungal or viral induced sepsis or septic shock, endotoxic shock (and associated conditions such as laminitis and colic in horses), and septic shock can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurological disorders such as spinal cord trauma, head injury, neurogenic inflammation, pain, and reperfusion injury of the brain can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Inflammatory disorders such as psoriatic arthritis, rheumatoid arthritis, ankylosing spondylitis, osteoarthritis, inflammation and cytokine-mediated chronic tissue degeneration can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Allergic disorders such as allergic rhinitis, allergic conjunctivitis, and eosinophilic granuloma can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Psychiatric disorders such as depression, memory impairment, and monopolar depression can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Neurodegenerative disorders such as Parkinson disease, Alzheimer's disease, acute and chronic multiple sclerosis can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Dermatological disorders such as psoriasis and other benign or malignant proliferative skin diseases, atopic dermatitis, and urticaria can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Oncological diseases such as cancer, tumor growth and cancerous invasion of normal tissues can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Metabolic disorders such as diabetes insipidus can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

Bone disorders such as osteoporosis, cardiovascular disorders such as arterial restenosis, atherosclerosis, reperfusion injury of the myocardium, and other disorders such as chronic glomerulonephritis, vernal conjunctivitis, transplant rejection and graft versus host disease, and cachexia can be conveniently treated with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered once, twice, or three times daily.

For enhancement of cognition (such as for of enhancied memory, learning, retention, recall, awareness and judgement), dosage levels from about 0.0001 mg/kg to about 50 mg/kg of body weight per day are useful or about 0.005 mg to about 2.5 g per patient per day. Alternatively, dosage levels from about 0.001 mg to 10 mg of the compound per kilogram of body weight per day, or alternatively about 0.05 mg to about 500 mg per patient per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier materia. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| cAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| dppf | 1,1'-bis(diphenylphosphino)-ferrocene |
| EDCI | 1-(3-dimethylaminopropyl)-3-ethylcarbodiimide hydrochloride |
| $Et_3N$ | triethylamine |
| GST | glutathione transferase |

-continued

| | |
|---|---|
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt 6H$_2$O |
| Ms | methanesulfonyl = mesyl = SO$_2$Me |
| MsO | methanesulfonate = mesylate |
| NBS | N-bromo succinimide |
| NSAID | non-steroidal anti-inflammatory drug |
| o-Tol | ortho-tolyl |
| OXONE ® | 2KHSO$_5$.KHSO$_4$.K$_2$SO$_4$ |
| PCC | pyridinium chlorochromate |
| Pd$_2$(dba)$_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

ALKYL GROUP ABBREVIATIONS

| | |
|---|---|
| Me= | Methyl |
| Et= | ethyl |
| n-Pr= | normal propyl |
| i-Pr= | isopropyl |
| n-Bu= | normal butyl |
| i-Bu= | isobutyl |
| s-Bu= | secondary butyl |
| t-Bu= | tertiary butyl |
| c-Pr= | cyclopropyl |
| c-Bu= | cyclobutyl |
| c-Pen= | cyclopentyl |
| c-Hex= | cyclohexyl |

Assays Demonstrating Biological Activity

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from E. coli, serotype 0111:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10 μL of fMLP (1 μM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for LTB$_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. IC$_{50}$ values should be less than about 5 μM, advantageously less than about 2.5 μM. The IC$_{50}$ values of Examples 1 to 155 ranged from 0.005 μM to 36 μM.

Anti-Allergic Activity in Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes.

Spa Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. the test compound was added (dissolved in 2 μL DMSO), 188 μL of substrate buffer containing [2,8-$^3$H]adenosine 3',5'-cyclic phosphate (cAMP, 100 nM to 50 μM), 10 μM MgCl$_2$, 1 mM EDTA, 50 mM Tris, pH 7.5. The reaction was initiated by the addition of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. IC$_{50}$ value was approximated with a non-linear regression fit using the standard 4-parameter/multiple binding sites equation from a ten point titration.

The IC$_{50}$ values of Examples 1 to 155 were determined with 100 nM cAMP using the purified GST fusion protein of the human recombinant phosphodiesterase IVa (met-248) produced from a baculovirus/Sf-9 expression system. IC$_{50}$ values should be less than about 1000 nM, advantageously less than about 250 nM, and even more advantageously less than about 100 nM. The IC$_{50}$ values of Examples 1 to 155 ranged from 0.086 nM to 160 nM.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass-spectrometry, nuclear magnetic resonance (NMR) spectrometry or microanalytical data. Yields are given for illustration only. When given, No data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles),mmol (millimoles), eq (equivalent(s)).

Methods of Synthesis

Compounds of the present invention can be prepared according to the following general methods. Reactions are typically run under nitrogen atmosphere at ambient temperature if not otherwise mention. Anhydrous solvent such as TB, DMF, Et$_2$O, DME and Tol are commercial grade.

Reagents are commercial grade and were used without any purification. Flash chromatography is run on silica gel (230–400 mesh).

All 8-aryl-quinoline of the type I were prepared (SCHEME 1 and SCHEME2) using a Suzuki coupling to build the biaryl moiety. In a typical Suzuki coupling reaction, all reagents except for the palladium catalyst are mixed in the appropriate solvent. The mixture is then degassed (—O$_2$) by refluxing for 15 min under nitrogen atmosphere, then cooling to rt, or by applying two to three vacuum/nitrogen sequences. The palladium catalyst is then added and the reaction mixture is stirred at the appropriate temperature until completion as monitored by TLC.

The substituents are the same as in Formula I except where defined otherwise. Compounds of the type I (SCHEME 1) can be prepared in a two step one-pot manner by generating in-situ the boronate analog of 8-bromo quinoline II followed by a palladium catalyzed coupling with the appropriate biaryl III

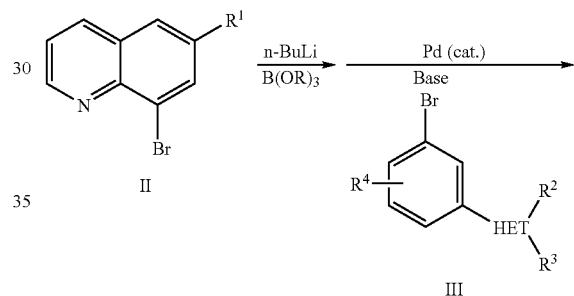

SCHEME 1

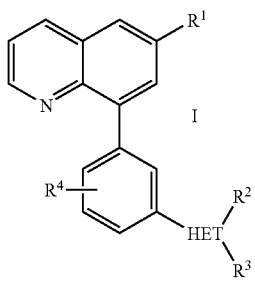

In most cases, compounds were prepared by the two procedures described in SCHEME 2. A Suzuki coupling between the 8-bromo-quinoline II and the bromo-phenyl-boronic acid IV produced to the common intermediate V. The latter can be coupled with either an aryl-stannane of type VI or a boronic acid of type VII to generate the desired compound I. Alternatively, the arylbromide V can be converted to the corresponding pinacole boronate VIII by a PdCl$_2$(dppf)$_2$ catalyzed coupling reaction with pinacole diborane. Subsequently, a Suzuki coupling of the boronate VIII with the appropriate heteroaryl bromide IX will generate the desired compound I

SCHEME 2

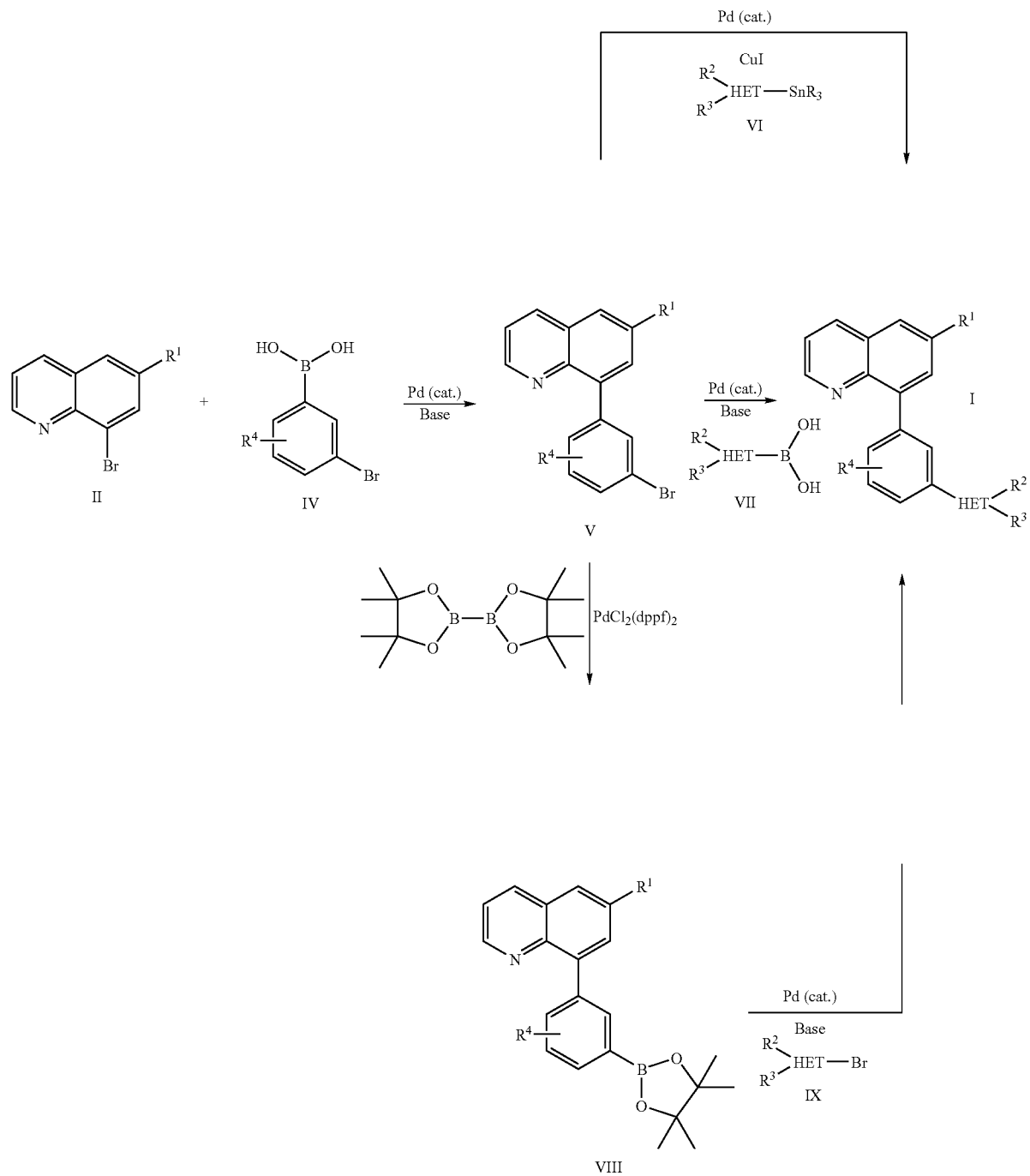

Boronic acid of the type VII can be prepared (SCHEME 3) by lithium-halogen exchange at low temperature in THF or Et$_2$O on the corresponding heteroaryl bromide IX followed by the addition of a trialkyl-boronate (B(OR)$_3$). Hydrolysis, under acidic condition, of the resulting heteroaryl-boronate will generate the desired boronic acid VII. Likewise, lithium-halogen exchange or deprotonation at low temperature in THF or Et$_2$O followed by the addition of a trialkylstannyl-chloride (R$_3$SnCl) generates the stannane of type VI.

SCHEME 3

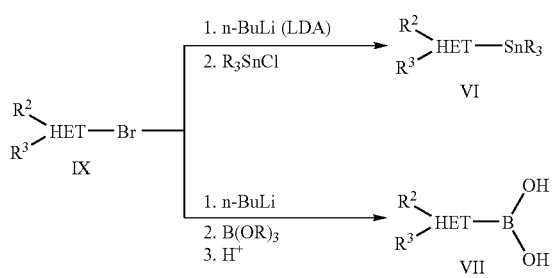

Intermediate of the type X can be generated by a mono lithium-halogen exchange at low temperature in ether followed by addition of various electrophils as exemplified in SCHEME 3a. Intermediate of the type XI can be generated by a selective mono lithium-halogen exchange at the 2 position in toluene at low temperature followed by addition of various electrophils as exemplified in SCHEME 3a. Intermediate of the type XII can be prepared by a selective nucleophilic displacement by using the sodium salt generated in DMF of various alcohols and mercaptans as exemplified in SCHEME 3a.

SCHEME 3a

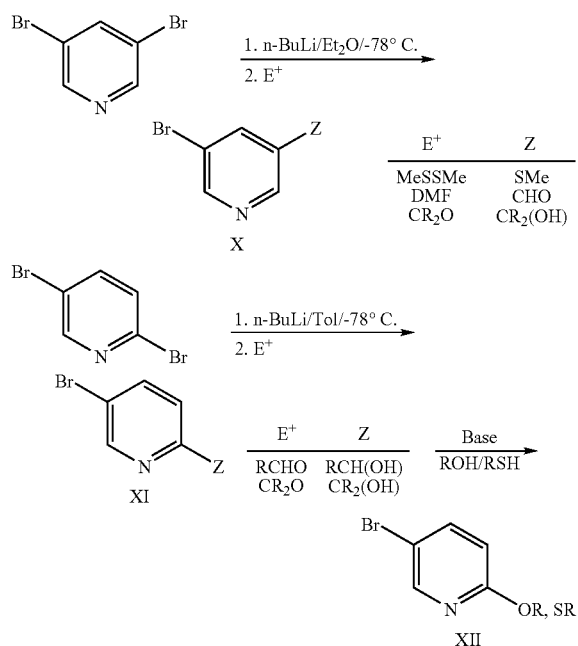

Intermediate of the type XIV can be generated in two steps by first, lithium-halogen exchange at low temperature in ether followed by addition of 1-trimethylsilanyl-2-(2-trimethylsilanyl-ethyldisulfanyl)-ethane to yield the thio-ether XIII. Secondly, upon addition of TBAF to XIII the thio-phenolate is formed and addition of the electrophile RX will generate the desired intermediate XIV. A similar reaction can be achieve on the sulfone XV, which will generate a nucleophilic sulfinate upon addition of TBAF.

SCHEME 4

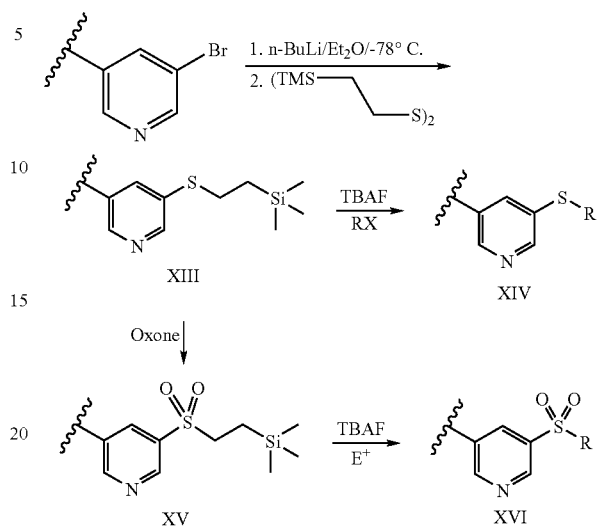

Intermediates such as XVIII are prepared from the steric hindered ester XVII. Deprotonation using lithium iso-propyl-cyclohexyl amine (1 eq.) followed by addition of MeI affords the mono alkylated analog. Repeating several time the same procedure will finally give the desired ester XVIII. The cyclopropyl ester XX can be prepare by a palladium catalyzed cyclopropanation using diazomethane.

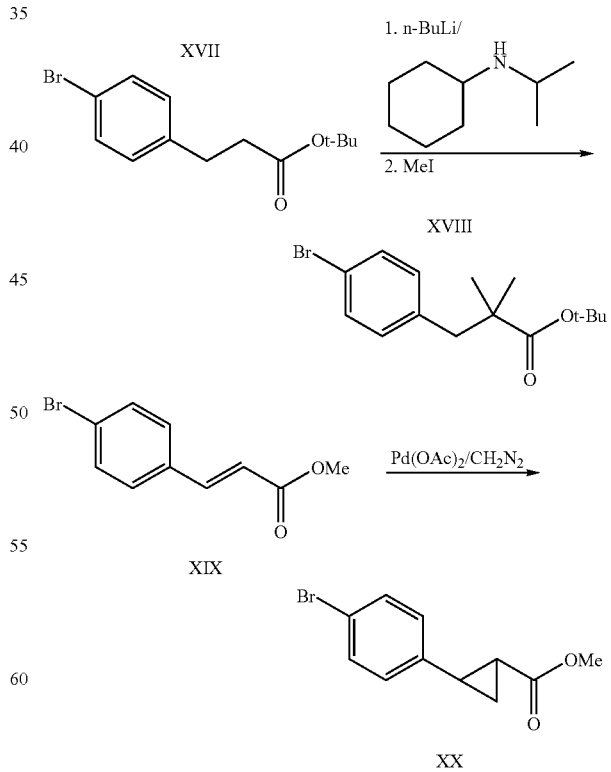

All the intermediates used for the preparation of the following compounds are commercially available or are prepared according to the litterature. The quinoline intermediates in Table 1 were prepared using the following procedures.

TABLE 1

| Compound | Structure |
|---|---|
| Quinoline 1 | (isopropyl quinoline with Br at 8-position) |
| Quinoline 2 | (quinoline with C(CH$_3$)$_2$SO$_2$CH$_3$ at 6-position, Br at 8-position) |
| Quinoline 3 | (quinoline with C(CH$_3$)$_2$SO$_2$CH$_3$ at 6-position, 3-bromophenyl at 8-position) |
| Quinoline 4 | (quinoline with C(CH$_3$)$_2$SO$_2$CH$_3$ at 6-position, 3-(pinacol boronate)-phenyl at 8-position) |

Quinoline 1

8-Bromo-6-isopropyl-quinoline

The preparation of Quinoline 1 is described in International Patent Publication WO 94/22852.

Quinoline 2

8-Bromo-6-(1-methanesulfonyl-1-methyl-ethyl)-quinoline

Step 1:
8-Bromo-6-methanesulfonylmethyl-quinoline

To a solution of 6-bromomethyl-8-bromoquinoline (1.0 eq.) described in International Patent Publication WO 94/22852 in DMF, was added sodium methanesulfinate (1.4 eq.). After stirring overnight at rt, the mixture was quenched with H$_2$O, stirred for 1 h. The resulting precipitate was isolated by filtration and washed with Et$_2$O to afford the title compound.

Step 2: Quinoline 2

To a solution of 8-bromo-6-methanesulfonylmethyl-quinoline from Step 1 (1 eq.) in THF (0.2M) at 0° C., was added potassium t-butoxide (1.3 eq.) over 30 min. After 0.5 h at 0° C., MeI (1.6 eq.) was added and the reaction mixture was stirred at 0° C. for 2 h. A second portion of potassium t-butoxide (1.3 eq.) was added over 30 min, followed by MeI (1.6 eq.). The final mixture was stirred at rt for 2 h. The mixture was poured in saturated aqueous NH4Cl and extracted with EtOAc (2×). The combined organic extracts were washed with brine, dried over MgSO$_4$, filtered and concentrated. The residue was vigorously stirred in Et$_2$O and the title compound was isolated by filtration as a pale yellow solid.

Quinoline 3

8-(3-Bromo-phenyl)-6-(1-methanesulfonyl-1-methyl-ethyl)-quinoline

A mixture of Quinoline 2 (1.0 eq.), 3-bromo phenylboronic acid (1.05 eq), Na$_2$CO$_3$ (2M in H$_2$O; 3.6 eq.) and Pd(PPh$_3$)$_4$ (0.03 eq.) in DME (0.2M) was stirred at 80° C. for 8 h. The resulting mixture was cooled to rt and diluted with water under vigourous stirring. The resulting precipitate-was filtered and dried. Flash chromatography (Hex:EtOAc; 2:3) and stirring in a mixture of Et$_2$O and CH$_2$Cl$_2$ (10:1) yielded the title compound as a light yellow solid after filtration.

Quinoline 4

6-(1-Methanesulfonyl-1-methyl-ethyl)-8-[3-(4,4,5,5-tetramethyl-[1,3,2]dioxaborolan-2-yl)-phenyl]-quinoline A mixture of Quinoline 3 (1.0 eq.), pinacole diborane ester (1.4 eq) and KOAc (3.5 eq.) and PdCl$_2$(dppf)$_2$ (0.03 eq.) in DMF (0.14M) was stirred at 60° C. for 24 h. An extra amount of pinacole diborane (0.3 eq), KOAc (1.05 eq.) and PdCl$_2$(dppf)$_2$ (0.01 eq.) were added and the mixture was stirred at 60° C. for 24 h. The resulting mixture was cooled to rt, diluted with EtOAc:Et$_2$O (1:1). The organic phase was washed with water (3×), brine, dried over MgSO$_4$, filtered and concentrated. Flash chromatography (CH$_2$Cl$_2$:EtOAc; 9:1) and stirring in Et$_2$O:EtOAc (10:1) afforded the title compound as a white solid.

EXAMPLE 1

8-Biphenyl-3-yl-6-isopropyl-quinoline

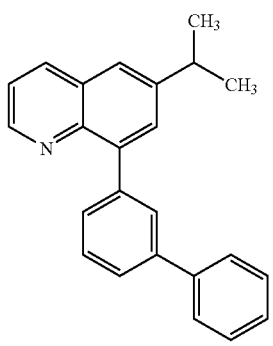

To a solution of Quinoline 1 (1.0 eq.) in Et$_2$O (0.1M) at −78° C. was added dropwise sec-BuLi (1.0 eq.). The mixture was stirred for 15 min then tri-isopropyl boronate (1.1 eq.) was added. The final mixture was warm to rt and concentrated. To the residue was added 3-bromo-1,1' biphenyl (1.5 eq.), Na$_2$CO$_3$ (2M in H$_2$O; 3.5 eq.) and Pd(PPh$_3$)$_4$ (0.0 Seq.) in Tol:EtOH (1:1, 0.2M). The mixture was stirred at 80° C. for 12 h, cooled to rt, poured in saturated aqueous NH$_4$Cl and extracted with EtOAc (2×). The combined organic extracts were washed with brine, dried over Na$_2$SO$_4$, filtered and concentrated. Flash chromatography (Hex:EtOAc; 9:1) afforded the title compound as an oil. $^1$H NMR (400 MHz, acetone-d$_6$): δ 8.82 (dd, 1H), 8.32 (dd, 1H), 7.99 (t, 1H), 7.81 (m, 2H), 7.75–7.66 (m, 4H), 7.55 (t, 1H), 7.5–7.45 (m, 3H), 7.36 (t, 1H), 3.21 (m, 1H), 1.39 (d, 6H).

EXAMPLE 2

1-{3'-[6-(1-Methanesulfonyl-1-methyl-ethyl)-quinolin-8-yl]-biphenyl-3-yl}-1-phenyl-ethanol

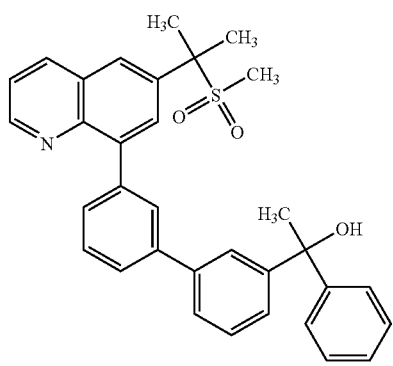

Step 1:1-{3'-[6-(1-Methanesulfonyl-1-methyl-ethyl)-quinolin-8-yl]-biphenyl-3-yl}-ethanone A mixture of Quinoline 3 (1.0 eq.), (3-acetyl-phenyl)-boronic acid (1.5 eq.), Na$_2$CO$_3$ (3.0 eq.; 2M in H$_2$O) and PdCl$_2$(dppf)$_2$ (0.05 eq.) in n-propanol (0.2M) was stirred at 80° C. for 2 h. The mixture was cooled to rt, poured in brine and extracted with EtOAc (2×). The combined organic extracts were dried over Na$_2$SO$_4$, filtered and concentrated. Flash chromatography (Hex:EtOAc; 9:1 to 1:9 over 20 min) afforded the title compound as a yellow solid.

Step 2: EXAMPLE 2

To a solution of 1-{3'-[6-(1-methanesulfonyl-1-methyl-ethyl)quinolin-8-yl]-biphenyl-3-yl}-ethanone from Step 1 (1.0 eq.) in THF (0.1M) was added CeCl$_3$ (1.1 eq.). The mixture was put in an ultrasonic bath for 15 min, cooled to −78° C. then phenyl magnesium bromide was added (5.0 eq.). The final mixture was stirred for 12 h at −20° C., poured in NaHCO$_3$ and extracted with EtOAc (2×). The combined organic extracts were washed with brine, dried over Na$_2$SO$_4$, filtered and concentrated. Flash chromatography (Hex:EtOAc; 9:1 to 1:9 over 20 min) afforded the title compound as a white solid. $^1$H NMR (400 MHz, acetone-d$_6$): δ 8.91 (dd, 1H), 8.46 (dd, 1H), 8.29 (d, 1H), 8.18 (d, 1H), 7.97 (d, 1H), 7.86 (d, 1H), 7.68 (dd, 1H), 7.64 (dd, 1H), 7.59–7.50 (m, 5H), 7.48 (d, 1H), 7.39 (t, 1H), 7.27 (t, 2H), 7.16 (t, 1H), 4.73 (s, 1H), 2.72 (s, 3H), 1.99 (s, 6H), 1.98 (s, 3H).

EXAMPLE 3

8-[3-(5—Chloro-thiophen-2-yl)-phenyl]-6-(1-methanesulfonyl-1-methyl-ethyl)-quinoline

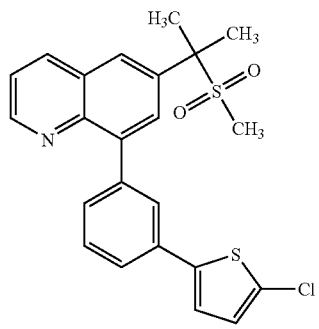

A mixture of Quinoline 4 (1.0 eq.), 2-bromo-3-chlorothiophene (2.0 eq.), Na$_2$CO$_3$ (3.0 eq.; 2M in H$_2$O) and PdCl$_2$(dppf)$_2$ (0.0 Seq.) in DME (0.2M) was stirred at 80° C. for 12 h. The mixture was cooled to rt and concentrated. Flash chromatography (Hex:EtOAc; 9:1 to 1:9 over 20 min) afforded the title compound as a yellow solid. $^1$H NMR (400 MHz, acetone-d$_6$): δ 8.93 (dd, 1H), 8.47 (dd, 1H), 8.3 (d, 1H), 8.19 (d, 1H), 7.97 (t, 1H), 7.69–7.64 (m, 2H), 7.60–7.52 (m, 2H), 7.35 (d,1H), 7.07 (d, 1H), 2.72 (s, 3H), 2.00 (s, 6H).

EXAMPLE 4

8-(3-Benzofuran-2-yl-phenyl)-6-(1-methanesulfonyl-1-methyl-ethyl)-quinoline

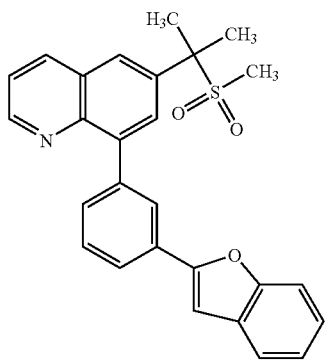

A mixture of Quinoline 3 (1.0 eq.), 2-benzofuran boronic acid (1.2 eq.), $Na_2CO_3$ (2.5 eq.; 2M in $H_2O$) and $Pd(PPh_3)_4$ (0.05 eq.) in DME (0.1M) was stirred at 80° C. for 12 h. The mixture was cooled to rt, poured in saturated aqueous $NH_4Cl$ and extracted with EtOAc (2×). The combined organic extracts were washed with brine, dried over $Na_2SO_4$, filtered and concentrated. Flash chromatography (Hex:EtOAc; 9:1 to 1:9 in 20 min) afforded the title compound as a yellow solid. $^1$H NMR (500 MHz, acetone-$d_6$): δ 8.93 (dd, 1H), 8.47 (dd, 1H), 8.30 (dd, 2H), 8.21 (s, 1H), 7.98 (dd, 1H), 7.75–7.55 (m, 5H), 7.30 (m, 2H), 7.25 (t, 1H), 2.73 (s, 3H), 2.01 (s, 6H).

EXAMPLE 5

{4-Fluoro-3'-[6-(1-methanesulfonyl-1-methyl-ethyl)-quinolin-8-yl]-biphenyl-3-yl}-methanol

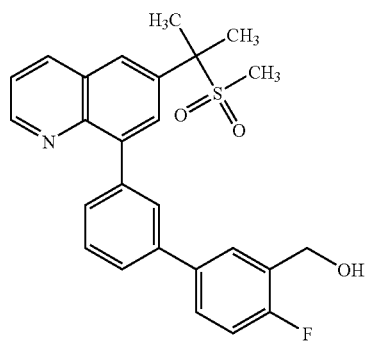

Step 1: 5-Bromo-2-fluoro-benzylalcohol

To a solution of 5-bromo-2-fluoro-benzaldehyde (1.0 eq.) in MeOH (0.2M) at 0° C. was added portionwise $NaBH_4$ (2.0 eq.). The mixture was stirred at rt for 1 h, poured in HCl (1M) and extracted with EtOAc (2×). The combined organic extracts were washed with brine, dried over $Na_2SO_4$, filtered and concentrated to afford the title compound as a white solid.

Step 2: 4-Fluoro-3-hydroxymethyl-phenylboronic acid

To a solution of 5-bromo-2-fluoro-benzylalcohol (1.0 eq.) from Step 1 in THF (0.1M) at −78° C. was added dropwise n-BuLi (2.2 eq.). The mixture was stirred at −78° C. for 15 min then tri-isopropylboronate (2.2 eq.) was added. The final mixture was warm slowly to rt, stirred for 1 h and quenched with HCl (1M). After stirring for 1 h, the mixture was extracted with EtOAc (2×). The combined organic extracts were washed with water, brine, dried over $Na_2SO_4$, filtered and concentrated. Stirring in Hex:EtOAc:$H_2O$ (90:9:1) for 12 h afforded the title compound which was isolated by filtration as a white solid.

Step 3: EXAMPLE 5

Prepared according to the procedure described in EXAMPLE 4 but using 4-fluoro-3-hydroxymethyl-phenyl-boronic acid from Step 2 as starting material. The title compound was obtained as a yellow solid. $^1$H NMR (500 MHz, acetone-$d_6$): δ8.91 (dd, 1H), 8.44 (dd, 1H), 8.28 (d, 1H), 8.20 (d, 1H), 7.99 (t, 1H), 7.87 (dd, 1H), 7.70–7.55 (m, 5H), 7.17 (t, 1H), 4.75 (d, 2H), 4.38 (t, OH), 2.72 (s, 3H), 1.99 (s, 6H).

EXAMPLE 6

2-(6-{3-[6-(1-Methanesulfonyl-1-methyl-ethyl)-quinolin-8-yl]-phenyl}-pyridin-2-yl)-propan-2-ol Step 1: 2-(6-Bromo-pyridin-2-yl)-propan-2-ol To a suspension of 2,6-dibromopyridine (1.0 eq.) in Et2O (0.2M) at −78° C. was added dropwise n-BuLi (1.05 eq.). The mixture was stirred at −78° C. for 45 min then acetone (1.5 eq.) was added. The final mixture was stirred for an extra 15 min at −78° C. and quenched with saturated aqueous $NaHCO_3$. The mixture was extracted with EtOAc (2×). The combined organic extracts were washed with, brine, dried over $MgSO_4$, filtered and concentrated to afford the title compound as a white solid which was used as such.

Step 2: EXAMPLE 6

A mixture of Quinoline 4 (1.0 eq.), 2-(6-bromo-pyridin-2-yl)-propan-2-ol (1.2 eq.), Na$_2$CO$_3$ (3.5 eq.; 2M in H$_2$O), Pd(OAc)$_2$ (0.05 eq.) and PPh$_3$ (0.15 eq.) in n-propanol (0.1M) was stirred at 80° C. for 15 min. The mixture was cooled to rt, poured in water and extracted with EtOAc (2×). The combined organic extracts were washed with brine, dried over Na$_2$SO$_4$, filtered and concentrated. Flash chromatography (Tol:Ace; 9:1) afforded the title compound as a white solid. $^1$H NMR (500 MHz, acetone-d$_6$): δ 8.95 (dd, 1H), 8.53 (t, 1H), 8.48 (dd, 1H), 8.32 (d, 1H), 8.26 (d, 1H), 8.20 (dt, 1H), 7.92–7.81 (m, 3H), 7.65–7.58 (m, 3H), 4.83 (s, OH), 2.76 (s, 3H), 2.03 (s, 6H:), 1.58 (s, 6H).

EXAMPLE 7

6-(1-Methanesulfonyl-1-methyl-ethyl)-8-[3-(6-methanesulfonyl-pyridin-2-yl)-phenyl]-quinoline

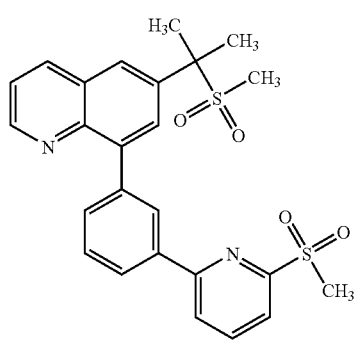

Step 1: 2-Bromo-6-methylsulfanyl-pyridine

To a solution of 2,6-dibromopyridine. (1.0 eq.) in DMSO (0.3M) was added sodium methylsulfide (1.1 eq.). The mixture was stirred for 2 d at rt then poured in water. The resulting precipitate was filtered off and the filtrate was extracted with Et$_2$O (2×). The combined organic extracts were washed with brine, dried over MgSO$_4$, filtered and concentrated to afford the title compound as a colorless oil.

Step 2: 6-(1-Methanesulfonyl-1-methyl-ethyl)-8-[3-(6-methylsulfanyl-pyridin-2-yl)-phenyl]-quinoline Prepared according to the procedure described in EXAMPLE 6, Step 2 but using 2-bromo-6-methylsulfanyl-pyridine as starting material. The title compound was obtained as a light yellow solid.

Step 3: EXAMPLE 7

To a solution of 6-(1-methanesulfonyl-1-methyl-ethyl)-8-[3-(6-methylsulfanyl-pyridin-2-yl)-phenyl]-quinoline from Step 2 (1.0 eq.) in THF:MeOH: saturated aqueous NaHCO$_3$ (2:1:1) was added Oxone (2.2 eq.). The mixture was stirred for 12 h at rt, poured in water and extracted with EtOAc (2×). The combined organic extracts were washed with brine, dried over Na$_2$SO$_4$, filtered and concentrated. Flash chromatography (Tol:Ace; 4:1) afforded the title compound as a white solid. $^1$H NMR (500 MHz, acetone-d$_6$): δ 8.93 (dd, 1H), 8.55 (t, 1H), 8.46 (dd, 1H), 8.30–8.20 (m, 5H), 7.99 (dd, 1H), 7.89 (dt, 1H), 7.65 (t, 1H), 7.57 (dd, 1H), 3.33 (s, 3H), 2.74 (s, 3H), 2.00 (s, 6H).

EXAMPLE 8

6-(1-Methanesulfonyl-1-methyl-ethyl)-8-[3-(6-methanesulfonyl-pyridin-3-yl)-phenyl]-quinoline

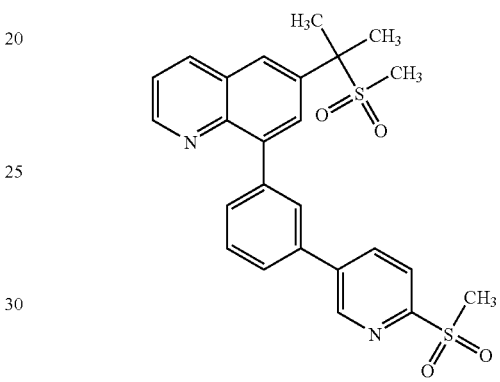

Step 1: 3-Bromo-6-methylsulfanyl-pyridine

To a solution of 3,6-dibromopyridine (1.0 eq.) in DMSO (0.3M) was added sodium methylsulfide (1.1 eq.). The mixture was stirred for 2 d at rt then poured in water. The resulting precipitate was filtered to afford the title compound as white solid.

Step 2: 6-(1-Methanesulfonyl-1-methyl-ethyl)-8-[3-(6-methylsulfanyl-pyridin-3-yl)-phenyl]-quinoline Prepared according to the procedure described in EXAMPLE 6, Step 2 but using 3-bromo-6-methylsulfanyl-pyridine as starting material. The title compound was obtained as a light yellow solid.

Step 3: EXAMPLE 8

Prepared according to the procedure described in EXAMPLE 7, Step 3 but using 6-(1-methanesulfonyl-1-methyl-ethyl)-8-[3-(6-methylsulfanyl-pyridin-3-yl)-phenyl]-quinoline as starting material. The title compound was obtained as a white solid. $^1$H NMR (500 MHz, acetone-d$_6$): δ 9.08 (d, 1H), 8.93 (dd, 1H), 8.45 (dd, 1H), 8.41 (dd, 1H), 8.31 (d, 1H), 8.24 (d, 1H), 8.16 (t, 1H), 8.11 (d, 1H), 7.86 (dd, 1H), 7.82 (d, 1H), 7.65 (t, 1H), 7.56 (dd, 1H), 3.26 (s, 3H), 2.73 (s, 3H), 2.00 (s, 6H).

EXAMPLE 9

6-(1-Methanesulfonyl-1-methyl-ethyl)-8-[3-(5-methanesulfonyl-1-oxy-pyridin-3-yl)-phenyl]-quinoline

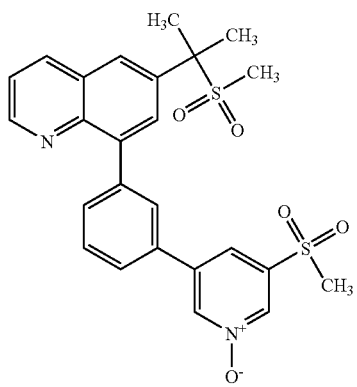

Step 1: (5-Methylsulfanyl-pyridin-3-yl)-boronic acid

To a suspension of 3,5-dibromopyridine (1.0 eq.) in Et$_2$O (0.1M) at −78° C. was added dropwise n-BuLi (1.05 eq.). The mixture was stirred at −78° C. for 15 min then dimethyldisulfide (1.0 eq.) was added. The mixture was stirred for 15 min and a second portion of n-BuLi (1.0 Seq.) was added. After stirring for 1 h at −78° C., tri-iso-propylboronate (1.5 eq.) was added. The final mixture was warmed slowly to rt and stirred for 12 h. An aqueous solution of HCl (1M) was added dropwise until pH=5. The resulting precipitate was filtered to afford the title compound as a white solid, which was used as such.

Step 2: 6-(1-Methanesulfonyl-1-methyl-ethyl)-8-[3-(5-methylsulfanyl-pyridin-3-yl)-phenyl]-quinoline Prepared according to the procedure described in EXAMPLE 4 but using (5-methylsulfanyl-pyridin-3-yl)-boronic acid as starting material. Upon completion of the reaction (4 h), the title compound was isolated by flash chromatography (EtOAc) as a light yellow solid.

Step 3: 6-(1-Methanesulfonyl-1-methyl-ethyl)-8-[3-(5-methanesulfonyl-pyridin-3-yl)-phenyl]-quinoline Prepared according to the procedure described in EXAMPLE 7, Step 3, but using 6-(1-methanesulfonyl-1-methyl-ethyl)-8-[3-(5-methylsulfanyl-pyridin-3-yl)-phenyl]-quinoline from step 2 as starting material. Flash chromatography was not required to get clean material.

Step 4: EXAMPLE 9

To a solution of 6-(1-methanesulfonyl-1-methyl-ethyl)-8-[3-(5-methanesulfonyl-pyridin-3-yl)-phenyl]-quinoline (1.0 eq.) in CH$_2$Cl$_2$ (0.1M) was added m-CPBA (1.3 eq.). The mixture was stirred at rt for 12 h, quenched with Ca(OH)$_2$ (0.7 eq) diluted with CH$_2$Cl$_2$ and filtered. The filtrate was concentrated and flash chromatography (EtOAc:MeOH; 9:1) afforded the title compound as a white solid. $^1$H NMR (500 MHz, acetone-d$_6$): δ 8.95 (dd, 1H), 8.74 (t, 1H), 8.54 (t, 1H), 8.48 (dd, 1H), 8.33 (d, 1H), 8.24 (d, 1H), 8.17 (t, 1H), 8.06 (t, 1H), 7.87 (t, 1H), 7.69 (t, 1H), 7.60 (dd, 1H), 3.40 (s, 3H), 2.75 (s, 3H), 2.02 (s, 6H).

EXAMPLE 10

8-(4'-Methanesulfonylmethyl-biphenyl-3-yl)$_6$-(1-methanesulfonyl-1-methyl-ethyl)-quinoline

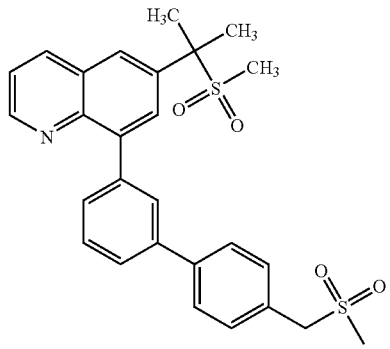

Step 1: {3'-[6-(1-Methanesulfonyl-1-methyl-ethyl)-quinolin-8-yl]-biphenyl-4-yl}-methanol Prepared according to the procedure described in EXAMPLE 4 but using (4-hydroxymethyl-phenyl)-boronic acid as starting material. Flash chromatography (Hex:EtOAc; 1:1) afforded the title compound as a white solid.

Step 2: 8-(4'-Bromomethyl-biphenyl-3-yl)-6-(1-methanesulfonyl-1-methyl-ethyl)-quinoline.

To a solution of {3'-[6-(1-methanesulfonyl-1-methyl-ethyl)-quinolin-8-yl]-biphenyl-4-yl}-methanol from Step 1 (1.0 eq.) in AcOH (0.3M) was added HBr (48%; 9.5 eq.). The mixture was stirred at 80° C. for 12 h, cooled to rt, poured in cold water containing 10 eq. of NaOH and extracted with EtOAc. The organic extract was washed with saturated aqueous NaHCO$_3$ (3×), brine, dried over Na$_2$SO$_4$, filtered and concentrated to afford the title compound as a yellow solid.

Step 3: EXAMPLE 10

To a solution of 8-(4'-Bromomethyl-biphenyl-3-yl)-6-(1-methanesulfonyl-1-methyl-ethyl)-quinoline (1.0 eq.) in DMF (0.1M) was added sodium methanesulfinate (1.3 eq.). The mixture was stirred at rt for 2 h, poured in water and extracted with EtOAc (2×). The combined organic extracts were washed with brine, dried over Na$_2$SO$_4$, filtered and concentrated. Flash chromatography (Hex:EA; 1:4) and stirring in EtOAc:Hex:Et$_2$O (1:7:2) afforded the title compound as a white solid after filtration. $^1$H NMR (400 MHz, acetone-d$_6$): δ 8.96 (dd, 1H), 8.49 (dd, 1H), 8.32 (d, 1H), 8.25 (d, 1H), 8.08 (t, 1H), 7.81–7.75 (m, 4H), 7.63–7.59 (m, 4H), 4.48 (s, 2H), 2.90 (s, 3H), 2.75 (s, 3H), 2.03 (s, 6H).

EXAMPLE 11

N-Cyclopropyl-3-{3'-[6-(1-methanesulfonyl-1-methyl-ethyl)-quinolin-8-yl]-biphenyl-3-yl}-acrylamide

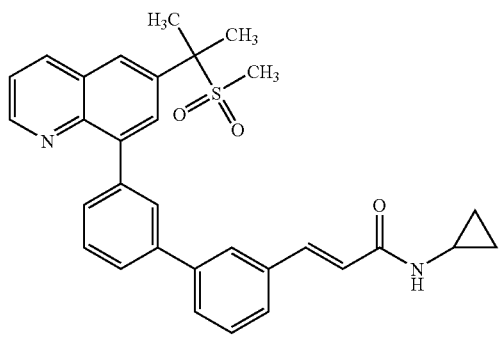

Step 1: 3'-[6-(1-Methanesulfonyl-1-methyl-ethyl)-quinolin-8-yl]-biphenyl-3-carbaldehyde Prepared according to the procedure described in EXAMPLE 4 but using (3-Formyl-phenyl)-boronic acid as starting material. Flash chromatography ($CH_2Cl_2$:EtOAc; 9:1) afforded the title compound as a white solid.

Step 2: 3-{3'-[6-(1-Methanesulfonyl-1-methyl-ethyl)-quinolin-8-yl]-biphenyl-3-yl}-acrylic acid To a solution of 3'-[6-(1-methanesulfonyl-1-methyl-ethyl)quinolin-8-yl]-biphenyl-3-carbaldehyde from Step 1 (1.0 eq.) and (dimethoxy-phosphoryl)-acetic acid methyl ester (1.1 eq.) in THF (0.1M) was added t-BuOK (1.1 eq.; 1.0M in THF). The final mixture was stirred 3 h at rt, poured in saturated aqueous NH4 Cl and extracted with EtOAc (2×). The combined organic extracts were washed with brine, dried over $Na_2SO_4$, filtered and concentrated. Flash chromatography ($CH_2Cl_2$:EtOAc; 9:1) afforded the corresponding methyl ester of the title compound as a yellow solid. To a solution of the methyl ester in THF:MeOH (4:1), aqueous NaOH (3.0 eq.) was added. The final mixture was stirred 4 h at rt, neutralized with AcOH, poured in saturated aqueous $NH_4Cl$ and extracted with EtOAc (2×). The combined organic extracts were washed with brine, dried over $Na_2SO_4$, filtered and concentrated to afford the title compound as a white solid.

Step 3: EXAMPLE 11

A mixture of 3-{3'-[6-(1-methanesulfonyl-1-methyl-ethyl)quinolin-8-yl]-biphenyl-3-yl}-acrylic acid from Step 2 (1.0 eq.), EDCI (1.3 eq.), DMAP (2.0 eq.) and cyclopropylamine (10.0 eq.) in $CH_2Cl_2$ was stirred for 12 h at rt. The mixture was poured in saturated aqueous $NH_4Cl$ and extracted with EtOAc (2×). The combined organic extracts were washed with saturated aqueous $NaHCO_3$, brine, dried over $Na_2SO_4$, filtered and concentrated. Flash chromatography (EtOAc) afforded the title compound as a white solid.

$^1$H NMR (500 MHz, acetone-$d_6$): δ 8.94 (dd, 1H), 8.46 (dd, 1H), 8.30 (d, 1H), 8.24 (d, 1H), 8.06 (s, 1H), 7.91 (s, 1H), 7.76–7.50 (m, 7H), 7.48 (t, 1H), 7.39 (d, NH), 6.7 (d, 1H), 2.87 (m, 1H), 2.75 (s, 3H), 2.02 (s, 6H), 0.71 (m, 2H), 0.52 (m, 2H).

EXAMPLE 12

6-(1-Methanesulfonyl-methyl-ethyl)-8-[3-(6-methyl-1-oxy-pyridin-3-yl)-phenyl]-quinoline

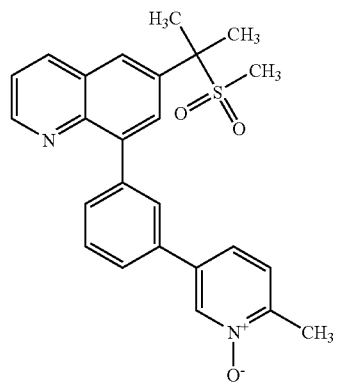

Step 1: 6-(1-Methanesulfonyl-1-methyl-ethyl)-8-[3-(6-methyl-pyridin-3-yl)-phenyl]-quinoline To a solution of 5-Bromo-2-methyl-pyridine (1.0 eq.) in $Et_2O$ (0.2M) at −78° C. was added dropwise n-BuLi (1.1 eq.). The resulting orange suspension was stirred 15 min at −78° C. then tri-iso-propylboronate (1.8 eq.) was added and the final mixture was warmed to 0° C. and stirred for 1 h. The reaction mixture was quenched with MeOH diluted with Tol and concentrated. To the residue in DME (0.2M) was added Quinoline 3 (0.35 eq.), $Na_2CO_3$ (3.7 eq.; aqueous 2M) and $PdCl_2(dppf)_2$ (0.1 eq.). The mixture was stirred at 80° C. for 4 h, cooled to rt, poured in water and extracted with EtOAc (2×). The combined organic extracts were washed with brine, dried over $Na_2SO_4$, filtered and concentrated. Flash chromatography (Tol:Ace; 4:1) afforded the title compound as a light yellow solid.

Step 2: EXAMPLE 12

Prepared according to the procedure described in EXAMPLE 9, Step 4, but using 6-(1-methanesulfonyl-1-methyl-ethyl)-8-[3-(6-methyl-pyridin-3-yl)-phenyl]-quinoline from Step I as starting material. Flash chromatography (EtOAc:MeOH; 9:1) afforded the title compound as a light yellow solid. $^1$H NMR (500 MHz, DMSO-$d_6$): δ 8.96 (dd, 1H), 8.59 (s, 1H), 8.52 (dd, 1H), 8.29 (d, 1H), 8.08 (d, 1H), 7.97 (d, 1H), 7.79 (dd, 1H), 7.74 (dd, 1H), 7.67–7.60 (m, 3H), 7.57 (d, 1H), 2.82 (s, 3H), 2.41 (s, 3H), 1.95 (s, 6H).

EXAMPLE 13

6-(1-Methanesulfonyl-1-methyl-ethyl)-8-[3-(1-oxy-pyridin-4-yl)-phenyl]-quinoline

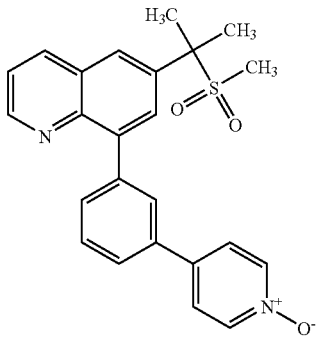

Step 1: 6-(1-Methanesulfonyl-1-methyl-ethyl)-8-(3-pyridin-4-yl-phenyl)-quinoline A mixture of Quinoline 3 (1.0 eq.), pyridin-4-yl-boronic acid (1.2 eq.), Na$_2$CO$_3$ (2.5 eq.; 2M in H$_2$O), Pd(PPh$_3$)$_4$ (0.05 eq.) in n-propanol (0.1M) was stirred at 80° C. for 4 h. The mixture was cooled to rt, poured in water and extracted with EtOAc (2×). The combined organic extracts were washed with brine, dried over Na$_2$SO$_4$, filtered and concentrated. Flash chromatography (CH$_2$Cl$_2$:EtOAc; 1:1) afforded the title compound as a white solid.

Step 2: EXAMPLE 13

Prepared according to the procedure described in EXAMPLE 9, Step 4, but using 6-(1-methanesulfonyl-1-methyl-ethyl)-8-(3-pyridin-4-yl-phenyl)-quinoline from Step 1 as starting material. Flash chromatography (EtOAc:MeOH; 4:1) afforded the title compound as a light yellow solid. $^1$H NMR (500 MHz, acetone-d$_6$): δ 8.93 (dd, 1H), 8.52 (dd, 1H), 8.32 (d, 1H), 8.25 (m, 3H), 8.12 (s, 1H), 7.80 (m, 4H), 7.60 (m, 2H), 2.75 (s, 3H), 2.05 (s, 6H).

EXAMPLE 14

6-(1-Methanesulfonyl-1-methyl-ethyl)-8-[3-(1-oxy-pyridin-3-yl)-phenyl]-quinoline

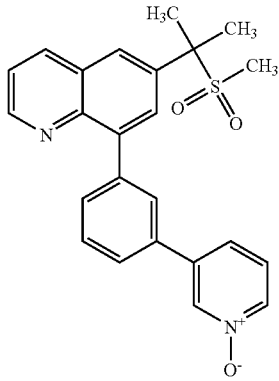

Step 1: 6-(1-Methanesulfonyl-1-methyl-ethyl)-8-(3-pyridin-3-yl-phenyl)-quinoline Prepared according to the procedure described in EXAMPLE 13, Step 1, but using pyridin-3-yl-boronic acid as starting material.

Step 2: EXAMPLE 14

Prepared according to the procedure described in EXAMPLE 9, Step 4, but using 6-(1-methanesulfonyl-1-methyl-ethyl)-8-(3-pyridin-3-yl-phenyl)-quinoline from Step 1 as starting material. $^1$H NMR (500 MHz, acetone-d$_6$): δ 8.93 (dd, 1H), 8.49 (s, 1H), 8.47 (dd, 1H), 8.32 (d, 1H), 8.23 (d, 1H), 8.15 (d, 1H), 8.07 (s, 1H), 7.83 (d, 1H), 7.77 (d, 1H), 7.65 (m, 2H), 7.6 (dd, 1H), 7.48 (t, 1H), 2.75 (s, 3H), 2.05 (s, 6H).

EXAMPLE 15

8-{3-[6-(4-Fluoro-phenylmethanesulfonyl)-pyridin-3-yl]-phenyl}-6-(1-methanesulfonyl-1-methyl-ethyl)-quinoline

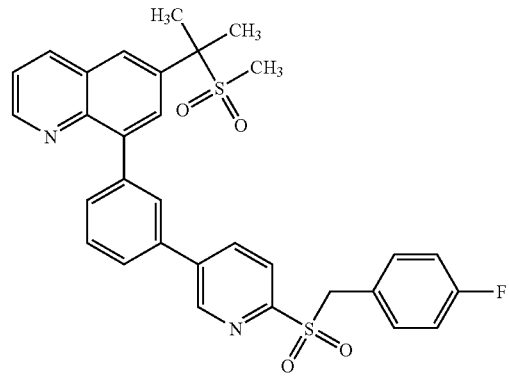

Step 1: 5-Bromo-2-(4-fluoro-benzylsulfanyl)-pyridine

To a solution of 2,5-dibromopyridine (1.0 eq.) and (4-fluoro-phenyl)-methanethiol (1.2 eq.) in DMF (0.2M) at 0° C. was added portionwise NaH (1.3 eq.). The mixture was stirred for 1 h at rt, poured in water and extracted with Et$_2$O. The organic extract was washed with water (2×), brine, dried over MgSO$_4$, filtered and concentrated. Flash chromatography (Hex:EtOAc; 9:1) afforded the title compound as a yellow solid.

Step 2: 5-Bromo-2-(4-fluoro-phenylmethanesulfonyl)-pyridine

Prepared according to the procedure described in EXAMPLE 7, Step 3, but using 5-bromo-2-(4-fluoro-benzylsulfanyl)-pyridine as starting material. Flash chromatography (Hex:EtOAc; 4:1) afforded the title compound as a white solid.

Step 3: EXAMPLE 15

Prepared according to the procedure described in EXAMPLE 6, Step 2, but using 5-bromo-2-(4-fluoro-phenylmethanesulfonyl)-pyridine as starting material. The reaction mixture was stirred 2 h at 80° C. Flash chromatography (Tol;Ace; 9:1) afforded the title compound as a white solid. $^1$H NMR (500 MHz, acetone-d$_6$): δ 9.20 (d, 1H), 8.97 (dd, 1H), 8.49 (dd, 1H), 8.37 (dd, 1H), 8.34 (d, 1H), 8.27 (d, 1H), 8.19 (d, 1H), 7.94 (d, 1H), 7.89–7.85 (m, 2H), 7.69 (t, 1H), 7.61 (dd, 1H), 7.37–7.35 (m, 2H), 7.08 (t, 2H), 4.78 (s, 2H), 2.76 (s, 3H), 2.03 (s, 6H).

EXAMPLE 16

2-(5-{3-[6-(1-Methanesulfonyl-1-methyl-ethyl)-quinolin-8-yl]-phenyl}-1-oxy-pyridin-2-yl)-propan-2-ol

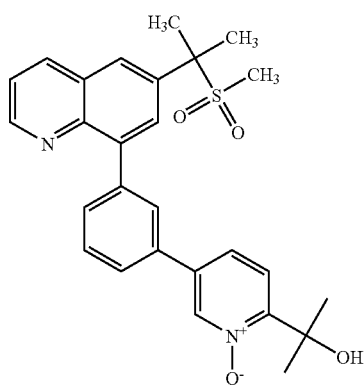

Step 1: 2-(5-Bromo-pyridin-2-yl)-propan-2-ol

To a suspension of 2,5-dibromopyridine (1.0 eq.) in Tol (0.1M) at −78° C. was added dropwise n-BuLi (1.07 eq.). The mixture was stirred at −78° C. for 3 h then acetone (1.2 eq.) was added. The final mixture was stirred for an extra 2 h at −78° C., poured in saturated aqueous $NH_4Cl$ and extracted with Tol (2×). The combined organic extracts were dried over $Na_2SO_4$, filtered and concentrated. Flash chromatography (Hex:EtOAc; 4:1) afforded the title compound as a white solid.

Step 2: 2-(5-Bromo-1-oxy-pyridin-2-yl)-propan-2-ol

Prepared according to the procedure described in EXAMPLE 9, Step 4, but using 2-(5-bromo-pyridin-2-yl)-propan-2-ol as starting material. Flash chromatography (Hex:EtOAc; 1:1) afforded the title compound as a white solid.

Step 3: EXAMPLE 16

Prepared according to the procedure described in EXAMPLE 6, Step 2, but using 2-(5-bromo-1-oxy-pyridin-2-yl)-propan-2-ol as starting material. Flash chromatography (EtOAc) and stirring in $Et_2O$:EtOAc (9:1) afforded the title compound as a white solid after filtration. $^1H$ NMR (500 MHz, acetone-$d_6$): δ 8.95 (dd, 1H), 8.71 (d, 1H), 8.54 (dd, 1H), 8.30 (d, 1H), 8.08 (d, 1H), 8.00 (d, 1H), 7.86–7.81 (m, 2H), 7.78 (d, 1H), 7.73 (d, 1H), 7.66–7.62 (m, 2H), 7.03 (s, OH), 2.82 (s, 3H), 1.95 (s, 6H), 1.63 (s, 6H).

EXAMPLE 17

N-Cyclopropyl-3-{3'-[6-(1-methanesulfonyl-1-methyl-ethyl)-quinolin-8-yl]-biphenyl-3-yl}-propionamide

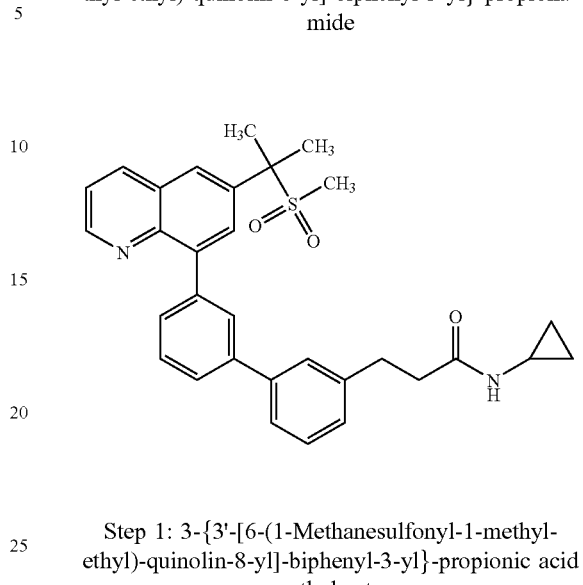

Step 1: 3-{3'-[6-(1-Methanesulfonyl-1-methyl-ethyl)-quinolin-8-yl]-biphenyl-3-yl}-propionic acid methyl ester To a solution of 3-{3'-[6-(1-methanesulfonyl-1-methyl-ethyl)-quinolin-8-yl]-biphenyl-3-yl}-acrylic acid methyl ester (1.0 eq.) from EXAMPLE 11, Step 2, in Tol (0.1M) at was added benzenesulfonyl hydrazide (3.8 eq.). The mixture was stirred at 100° C. for 12 h, cooled to rt, poured in saturated aqueous $NaHCO_3$ and extracted with EtOAc (2×). The combined organic extracts were washed with brine, dried over $MgSO_4$, filtered and concentrated. Flash chromatography ($CH_2Cl_2$:EtOAc; 8.5:1.5) afforded the title compound as a white solid.

Step 2: 3-{3'-[6-(1-Methanesulfonyl-1-methyl-ethyl)-quinolin-8-yl]-biphenyl-3-yl}-propionic acid To a solution of 3-{3'-[6-(1-methanesulfonyl-1-methyl-ethyl)-quinolin-8-yl]-biphenyl-3-yl}-propionic acid methyl ester (1.0 eq.) from step 1, in TBF:MeOH (2:1; 0.2M) was added aqueous LiOH (2M; 4.0 eq.). The mixture was stirred for 12 h at rt, quenched with AcOH (20 eq.), poured in saturated aqueous $NH_4OAc$ and extracted with EtOAc (2×). The combined organic extracts were washed with brine, dried over $Na_2SO_4$, filtered and concentrated. Crystallization in Hex:$CH_2Cl_2$ afforded the title compound as a white solid.

Step 3: EXAMPLE 17

Prepared according to the procedure described in EXAMPLE 11, Step 3, but using 3-{3'-[6-(1-methanesulfonyl-1-methyl-ethyl)-quinolin-8-yl]-biphenyl-3-yl}-propionic acid from step 2, as starting material. $^1H$ NMR (500 MHz, acetone-$d_6$): δ 8.95 (dd, 1H), 8.48 (dd, 1H), 8.32 (d, 1H), 8.23 (d, 1H), 8.02 (s, 1H), 7.71 (m, 2H), 7.60 (m, 41), 7.38 (t, 1H), 7.23 (d, 1H), 7.05 (s, NH), 2.98 (t, 2H), 2.75 (s, 3H), 2.64 (m, 1H), 2.46 (t, 2H), 2.03 (s, 6H), 0.56 (m, 2H), 0.35 (m, 2H).

EXAMPLE 18

{33'-[6-(1-Methanesulfonyl-1-methyl-ethyl)-quinolin-8-yl]-biphenyl-3-yl}-phosphonic acid diethyl ester

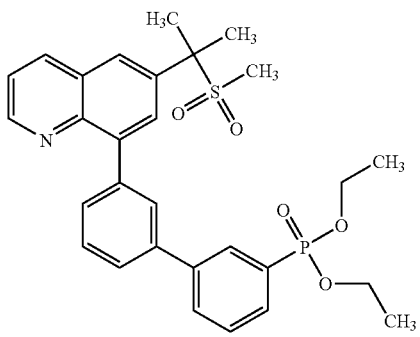

Prepared according to the procedure described in EXAMPLE 6, Step 2, but using (3-bromo-phenyl)-phosphonic acid diethyl ester as starting material. Upon completion of the reaction (1 h) the title compound was isolated by flash chromatography (EtOAc) as a light yellow solid. $^1$H NMR (500 MHz, acetone-$d_6$): δ 8.94 (dd, 1H), 8.49 (dd, 1H), 8.32 (d, 1H), 8.28 (d, 1H), 8.12 (d, 1H), 8.10 (s, 1H), 8.0 (d, 1H), 7.85–7.55 (m, 6H), 4.12 (m, 4H), 2.77 (s, 3H), 2.05 (s, 6H), 1.30 (t, 6H).

EXAMPLE 19

5-{3-[6-(1-Methanesulfonyl-1-methyl-ethyl)-quinolin-8-yl]-phenyl}-1H-pyridin-2-one

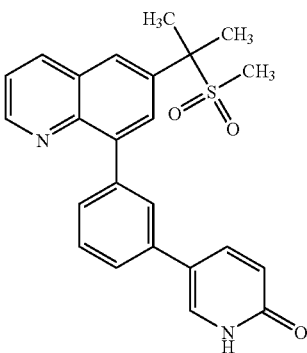

Step 1: 2-Benzyloxy-5-bromo-pyridine

A mixture of 2,5-dibromopyridine (1.0 eq.), benzyl alcohol (1.3 eq.), KOH (2.4 eq.) and DB-18—C-6 (0.0 Seq.) in toluene (0.3M) was refluxed for 3 h, then stirred overnight at rt. The mixture was concentrated, poured in water and extracted with Tol (2×). The combined organic extracts were dried over MgSO$_4$, filtered and concentrated. Recrystallization in Hex:Et$_2$O afforded the title compound as a white solid.

Step 2: 8-[3-(6-Benzyloxy-pyridin-3-yl)-phenyl]-6-(1-methanesulfonyl-1-methyl-ethyl)-quinolin Prepared according to the procedure described in EXAMPLE 6, Step 2, but using 2-benzyloxy-5-bromo-pyridine as starting material. Upon completion of the reaction (1 h) the title compound was isolated by flash chromatography (Tol:Ace; 9:1) as a light yellow solid.

Step 3: EXAMPLE 19

To a solution of 8-[3-(6-Benzyloxy-pyridin-3-yl)-phenyl]-6-(1-methanesulfonyl-1-methyl-ethyl)-quinoline from Step 2 (1.0 eq.) in CH$_2$Cl$_2$ (0.2M) was added an equi volume of TFA. The mixture was stirred for 72 h, concentrated, poured in saturated aqueous NaHCO$_3$ and extracted with EtOAc (2×). The combined organic extracts were washed with brine, dried over Na$_2$SO$_4$, filtered and concentrated. Flash chromatography (CH$_2$Cl$_2$:MeOH; 95:5) afforded the title compound as a light yellow solid. $^1$H NMR (500 MHz, DMSO-$d_6$): δ 8.95 (dd, 1H), 8.53 (d, 1H), 8.28 (d, 1H), 8.04 (d, 1H), 7.89 (dd, 1H), 7.79 (s, 1H), 7.75 (s, NH), 7.63–7.53 (m, 4H), 6.46 (d, 1H), 2.82 (s, 3H), 1.94 (s, 6H).

EXAMPLE 20

2-(5-{3-[6-(1-Methanesulfonyl-1-methyl-ethyl)-quinolin-8-yl]-phenyl}-1-oxy-pyridin-3-yl)-propan-2-ol

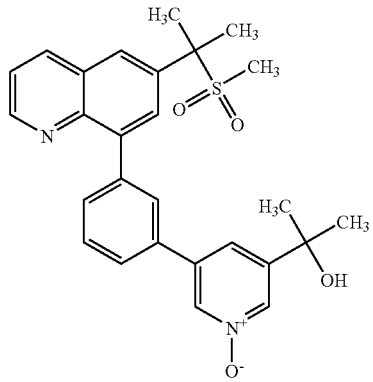

Step 1: 2-(5-Bromo-pyridin-3-yl)-propan-2-ol

To a solution of 5-bromo-nicotinic acid ethyl ester (1.0 eq.) in Et$_2$O (0.3M) at −30° C. was added MeMgBr (2.7 eq.; 3M in Et$_2$O). The mixture was refluxed for 2 h, poured in 0.5M aqueous NaH$_2$PO$_4$ and extracted with Et$_2$O (2×). The combined organic extracts were washed with brine, dried over Na$_2$SO$_4$, filtered and concentrated. Flash chromatography (Hex:Et$_2$O:CH$_2$Cl$_2$; 2:1:2) afforded the title compound as a yellow oil.

Step 2: 2-(5-Bromo-1-oxy-pyridin-3-yl)-propan-2-ol

Prepared according to the procedure described in EXAMPLE 9, Step 4, but using 2-(5-bromo-pyridin-3-yl)-propan-2-ol as starting material. Flash chromatography (CH$_2$Cl$_2$:EtOH; 9:1) afforded the title compound as a white solid.

Step 3: EXAMPLE 20

Prepared according to the procedure described in EXAMPLE 6, Step 2, but using 2-benzyloxy-5-bromo-pyridine as starting material. Upon completion of the reaction (1 h) the title compound was isolated by flash chromatography (EtOAc:MeOH; 8.5:1.5) as a light yellow solid. $^1$H NMR (500 MHz, acetone-$d_6$): δ 8.90 (dd, 1H), 8.42 (dd, 1H), 8.32 (s, 1H), 8.28 (s, 1), 8.26 (s, 1H), 8.20 (d, 1H), 8.03 (t, 1H), 7.74 (m, 2H), 7.67 (d, 1H), 7.54 (m, 2H), 5.05 (s, OH), 2.72 (s, 3H), 1.98 (s, 6H), 1.58 (s, 6H).

EXAMPLE 21

N-(3,5-Dichloro-pyridin-4-yl)-3-{3'-[6-(1-methanesulfonyl-1-methyl-ethyl)-quinolin-8-yl]-biphenyl-4-yl}-acrylamide

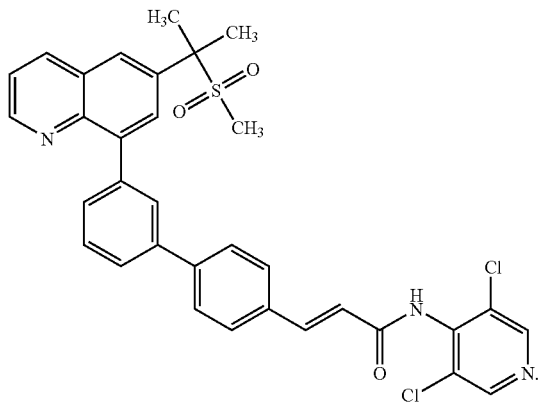

Step 1: 3'-[6-(1-Methanesulfonyl-1-methyl-ethyl)-quinolin-8-yl]-biphenyl-4-carbaldehyde Prepared according to the procedure described in EXAMPLE 4 but using (4-formyl-phenyl)-boronic acid as starting material. Flash chromatography (Hex:EtOAc; 1:1) afforded the title compound as a white solid.

Step 2: 3-{3'-[6-(1-Methanesulfonyl-1-methyl-ethyl)-quinolin-8-yl]-biphenyl-4-yl}-acryl acid Prepared according to the procedure described in EXAMPLE 11, Step 2, but using 3'-[6-(1-methanesulfonyl-1-methyl-ethyl)-quinolin-8-yl]-biphenyl-4-carbaldehyde from Step 1 as starting material. Stirring in Hex:Et$_2$O (8:2) afforded the title compound after filtration.

Step 3: 3-{3'-[6-(1-Methanesulfonyl-1-methyl-ethyl)-quinolin-8-yl]-biphenyl-4-yl}-acrylic acid 4-nitro-phenyl ester Prepared according to the procedure described in EXAMPLE 11, Step 3 but using 3-(3'-[6-(1-methanesulfonyl-1-methyl-ethyl)-quinolin-8-yl]-biphenyl-4-yl)-acrylic acid and 4-nitro-phenol as starting materials. Stirring in Et$_2$O afforded the title compound after filtration.

Step 4: EXAMPLE 21

To a solution of 3,5-dichloro-pyridin-4-ylamine (1.5 eq.) in DMF (0.1M) was added t-BuONa (1.5 eq.). The mixture was stirred for 15 min then 3-{3'-[6-(1-methanesulfonyl-1-methyl-ethyl)-quinolin-8-yl]-biphenyl yl}-acrylic acid 4-nitro-phenyl ester (1.0 eq.) was added. The final mixture was stirred for 12 h, poured in saturated aqueous NH$_4$Cl and extracted with EtOAc (2×). The combined organic extracts were washed with brine, dried over Na$_2$SO$_4$, filtered and concentrated. Flash chromatography (Hex:EtOAc; 9:1 to 1:9 in 20 min) afforded the title compound as a yellow solid. $^1$H NMR (400 MHz, acetone-$d_6$): δ 9.44 (br s, 1H), 8.97 (dd, 1H), 8.64 (s, 2H), 8.50 (dd, 1H), 8.33 (d, 1H), 8.26 (d, 1H), 8.11 (t, 1H), 7.87–7.77 (m, 7H), 7.65–7.60 (m, 2H), 7.09 (d, 1H), 2.81 (s, 3H), 2.04 (s, 6H).

EXAMPLE 22

3-Hydroxy-1-{3'-[6-(1-methanesulfonyl-1-methyl-ethyl)-quinolin-8-yl]-biphenyl-3-yl}-3-methyl-butan-2-one

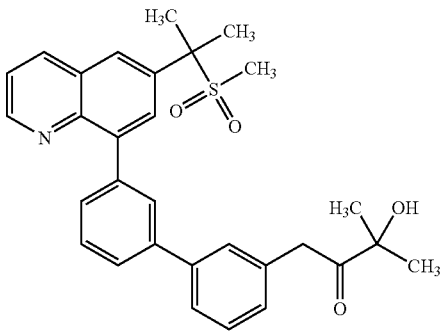

Step 1: 1-(3-Bromo-phenyl)-3-hydroxy-3-methyl-butan-2-one

A mixture of 1,3-dibromobenzene (1.0 eq.), 3-hydroxy-3-methyl-butan-2-one (1.0 eq.), Pd$_2$(dba)$_3$ (0.02 eq.), xantphos (0.04 eq.) and t-BuONa (1.1 eq.) in THF (0.15M) was stirred at 60° C. for 2 h, poured in saturated aqueous NH$_4$Cl and extracted with EtOAc (2×). The combined organic extracts were washed with brine, dried over Na$_2$SO$_4$, filtered and concentrated. Flash chromatography (Hex:EtOAc; 7:3) afforded the title compound as an oil.

Step 2: EXAMPLE 22

Prepared according to the procedure described in EXAMPLE 6, Step 2, but using 1-(3-bromo-phenyl)-3-hydroxy-3-methyl-butan-2-one from Step 1 as starting material. Upon completion of the reaction (1 h) the title compound was isolated by flash chromatography (EtOAc:MeOH; 1:1 to 3:7) as a light yellow solid. $^1$H NMR (500 MHz, acetone-$d_6$): δ 8.95 (d, 1H), 8.49 (d, 1H), 8.32 (d, 1H), 8.23 (d, 1H), 8.03 (s, H), 7.72 (t, 2H), 7.62–7.58 (m, 4H), 7.43 (t, 1H), 7.25 (d, 1H), 4.45 (s, 1H), 4.15 (s, 2H), 2.75 (s, 3H), 2.03 (s, 6H), 1.38 (s, 6H).

EXAMPLE 23

N-Cyclopropyl-5-{3-[(6(1-methanesulfonyl-1-methyl-ethyl)-quinolin-8-yl]-phenyl}-1-oxy-nicotinamide

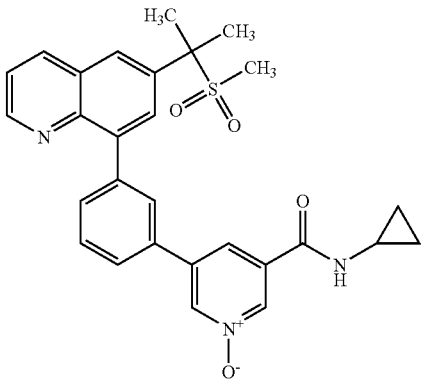

Step 1: 5-Bromo-N-cyclopropyl-nicotinamide

Prepared according to the procedure described in EXAMPLE 11 (Step 3) but using 5-bromo-nicotinic acid as starting material. Flash chromatography (EtOAc) afforded the title compound as a white solid.

Step 2: 5-Bromo-N-cyclopropyl-1-oxy-nicotinamide

Prepared according to the procedure described in EXAMPLE 9 (Step 4) but using 5-bromo-N-cyclopropyl-nicotinamide from Step 1 as starting material. Flash chromatography (EtOAc:MeOH; 9:1) afforded the title compound as a white solid.

Step 3: EXAMPLE 23

Prepared according to the procedure described in EXAMPLE 6 (Step 2) but using 5-bromo-N-cyclopropyl-1-oxy-nicotinamide from Step 2 as starting material. Upon completion of the reaction (1 h), flash chromatography (EtOAc:MeOH; 4:1) afforded the title compound as a white solid. $^1$H NMR (500 MHz, acetone-$d_6$): δ 8.94 (dd, 1H), 8.58 (s, 1H), 8.53 (s, 1H), 8.47 (d, 1H), 8.33 (d, 1H), 8.23 (d, 1H), 8.19 (s, NH), 8.09 (s, 1H), 8.00 (s, 1H), 7.78 (dd, 2H), 7.63 (t, 1H), 7.58 (dd, 1H), 2.94 (m, 1H), 2.76 (s, 3H), 2.02 (s, 6H), 0.75 (m, 2H), 0.65 (m, 2H).

EXAMPLE 24

8-{3-[5-(4-Fluoro-phenylmethanesulfonyl)-1-oxy-pyridin-3-yl]-phenyl}-6-(1-methanesulfonyl-1-methyl-ethyl)-quinoline

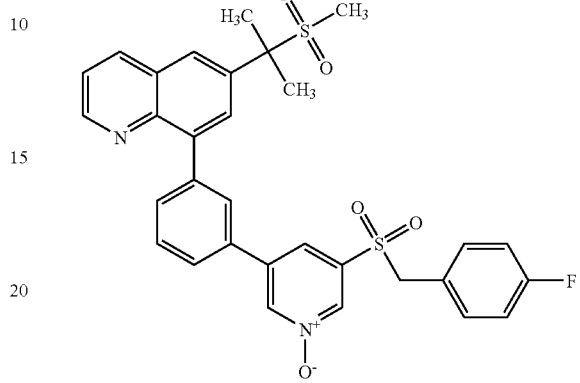

Step 1: [5-(2-Trimethylsilanyl-ethylsulfanyl)-pyridin-3-yl]-boronic acid

To a suspension of 3,5-dibromopyridine (1.0 eq.) in Et$_2$O (0.18M) at −65° C. was added dropwise n-BuLi (1.15 eq.). The mixture was stirred for 30 min then 1-trimethylsilanyl-2-(2-trimethylsilanyl-ethyldisulfanyl)-ethane (1.15 eq.) was added. The resulting light orange solution was stirred at −65° C. for 20 min. Subsequently, a second portion of n-BuLi (1.15 eq.) was added. After stirring for 45 min, tri-iso-propylboronate (1.15 eq.) was added. The final mixture was warmed slowly and stirred for 12 h at rt, quenched with aqueous HCl (1M) to pH=5, stirred for 30 min, extracted with Et$_2$O (2×). The combined organic extracts were poured in aqueous NaOH (1N). The aqueous phase was washed with Et$_2$O (2×), neutralized to pH=5 using HCl (1N) and extracted with Et$_2$O (2×). The combined organic extracts were washed with brine, dried over MgSO$_4$, filtered and concentrated to afford the title compound as a white solid.

Step 2: 6-(1-Methanesulfonyl-1-methyl-ethyl)-8-{3-[5-(2-trimethylsilanyl-ethylsulfanyl)-pyridin-3-yl]-phenyl}-quinoline A mixture of Quinoline 3 (1.0 eq.), [5-(2-trimethylsilanyl-ethylsulfanyl)-pyridin-3-yl]-boronic acid (1.2 eq.), Na$_2$CO$_3$ (2.5 eq.; 2M in H$_2$O) and PdCl$_2$(dppf)$_2$ (0.06 eq.) in DME (0.2 M) was stirred at 80° C. for 2.5h. The mixture was cooled to room temperature, poured in water and extracted with EtOAc (2×). The combined organic extracts were washed with brine, dried over Na$_2$SO$_4$, filtered and concentrated. Flash chromatography (Hex:EtOAc; 3:7) and stirring in Hex:Et$_2$O (1:1) afforded the title compound as a white solid after filtration.

Step 3: 6-(1-Methanesulfonyl-1-methyl-ethyl)-8-{3-[5-(2-trimethylsilanyl-ethanesulfonyl)-pyridin-3-yl]-phenyl}-quinoline Prepared according to the procedure described in EXAMPLE 7 (Step 3) but using 6-(1-methanesulfonyl-1-methyl-ethyl)-8-{3-[5-(2-trimethylsilanyl-ethylsulfanyl)- pyridin-3-yl]-phenyl}-quinoline from Step 2 as starting material. Upon completion of the reaction (4h) and work-up, the title compound (white solid) was isolated and used without any purification.

Step 4: 6-(1-Methanesulfonyl-1-methyl-ethyl)-8-{3-[1-oxy-5-(2-trimethylsilanyl-ethanesulfonyl)-pyridin-3-yl]-phenyl}-quinoline Prepared according to the procedure described in EXAMPLE 9 (Step 4) but using 6-(1-methanesulfonyl-1-methyl-ethyl)-8-{3-[5-(2-trimethylsilanyl-ethanesulfonyl)-pyridin-3-yl]-phenyl}-quinoline from step 3 as starting material. Flash chromatography (EtOAc:EtOH; 95:5) and stirring in Et$_2$O afforded the title compound as a white solid after filtration.

Step 5: EXAMPLE 24

To a solution of 6-(1-methanesulfonyl-1-methyl-ethyl)-8-{3-[1-oxy-5-(2-trimethylsilanyl-ethanesulfonyl)-pyridin-3-yl]-phenyl}-quinoline from Step 4 (1.0 eq.) in DMF (0.2M) was added tetramethyl-ammonium fluoride (2.4 eq.). The mixture was stirred for 1 h then 4-fluorobenzyl bromide (1.3 eq.) was added. The final mixture was stirred for 1 h, poured in water and extracted with EtOAc (2×). The combined organic extracts were washed with brine, dried over Na$_2$SO$_4$, filtered and concentrated. Flash chromatography (EtOAc:EtOH; 95:5) afforded the title compound as a white solid. $^1$H NMR (500 MHz, acetone-d$_6$): δ 8.97 (d, 1H), 8.73 (s, 1H), 8.51 (d, 2H), 8.35 (d, 1H), 8.30 (s, 1H), 8.25 (d, 1H), 8.07 (s, 1H), 7.88 (d, 1H), 7.76 (m, 1H), 7.69 (t, 1H), 7.63 (dd, 1H), 7.45 (dd, 2H), 7.12 (t, 2H), 4.84 (s, 2H), 2.76 (s, 3H), 2.03 (s, 6H).

EXAMPLE 25

5-{3-[6-(1-Methanesulfonyl-1-methyl-ethyl)-quinolin-8-yl]-phenyl}-1-oxy-pyridine-2-carboxylic acid cyclopropylamide

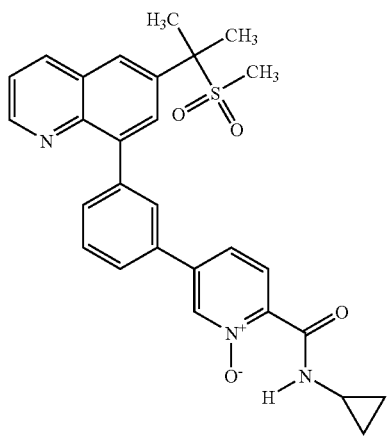

Step 1: 5-Bromo-pyridine-2-carboxylic acid cyclopropylamide

To a solution of 5-bromo-pyridine-2-carboxylic acid methyl ester (1.0 eq.) (see *Synth. Commun.*, 1997, 27, 515) in THF:MeOH (2:1; 0.2M) was added aqueous LiOH (1M; 3.0 eq.). The mixture was stirred for 12 h, concentrated and dried under vacuum. The residue was diluted in CH$_2$Cl$_2$ (0.2M), oxalyl chloride (8.0 eq.) was added and the mixture was stirred for 3h, concentrated, dried under vacuum and diluted in CH$_2$Cl$_2$ (0.2M). Cyclopropylamine (10 eq.) was added and the mixture was stirred for 2 h, poured in saturated aqueous NaHCO$_3$ and extracted with EtOAc (2×). The combined organic extracts were washed with brine, dried over Na$_2$SO$_4$, filtered and concentrated. Flash chromatography (CH$_2$Cl$_2$:EtOAc; 9:1) afforded the title compound as a yellow solid.

Step 2: 5-Bromo-1-oxy-pyridine-2-carboxylic acid cyclopropylamide

Prepared according to the procedure described in EXAMPLE 9 (Step 4) but using 5-bromo-pyridine-2-carboxylic acid cyclopropylamide from Step 1 as starting material. Flash chromatography (CH$_2$Cl$_2$:EtOAc; 9:1) afforded the title compound as a white solid.

Step 3: EXAMPLE 25

Prepared according to the procedure described in EXAMPLE 6 (Step 2) but using 5-bromo-1-oxy-pyridine-2-carboxylic acid cyclopropylamide from Step 2 as starting material. Flash chromatography (EtOAc) afforded the title compound as a white solid. $^1$H NMR (500 MHz, CDCl$_3$): δ 11.18 (d, NH), 8.94 (dd, 1H), 8.49 (d, 1H), 8.41 (d, 1H), 8.24 (d, 1H), 8.06 (s, 1H), 8.05 (s, 1H), 7.90 (s, 1H), 7.74 (d, 1H), 7.68 (dd, 1H), 7.60 (m, 2H), 7.45 (m, 1H), 2.96 (m, 1H), 2.61 (s, 3H), 1.97 (s, 6H), 0.83 (m, 2H), 0.64 (m, 2H).

EXAMPLE 26

6(1-Methanesulfonyl-1-methyl-ethyl)-8-[3-(6-methoxymethyl-1-oxy-pyridin-3-yl)-phenyl]-quinoline

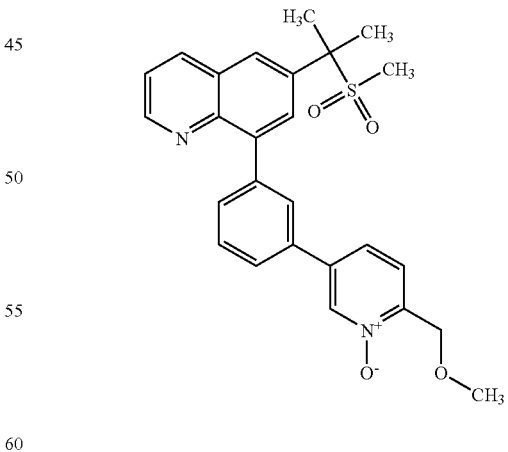

Step 1: 5-Bromo-pyridine-2-carbaldehyde

To a solution of 2,5-dibromopyridine (1.0 eq.) in Tol (0.1M) at −78° C. was added n-BuLi (1.0Seq.). The mixture was stirred for 2 h at −78° C. then DMF (3.0 eq.) was added. The final mixture was stirred for 12 h at −78° C., quenched using saturated aqueous NH₄Cl and extracted with Et₂O (2×). The combined organic extracts were washed with brine, dried over MgSO₄, filtered and concentrated. Flash chromatography (Hex:EtOAc; 9:1) afforded the title compound as an oil.

Step 2: (5-Bromo-pyridin-2-yl)-methanol

To a solution of 5-bromo-pyridine-2-carbaldehyde (1.0 eq.) in THF:EtOH (1:1; 0.2M) at −78° C. was added NaBH₄ (4.0 eq.). The mixture was stirred for 2 h at −78° C., quenched with excess AcOH, poured in aqueous HCl (1M), stirred for 15 min, neutralized to pH=7 with NaOH (1M) and extracted with EtOAc (2×). The combined organic extracts were washed with brine, dried over Na₂SO₄, filtered and concentrated to afford the title compound as an oil.

Step 3: (5-Bromo-1-oxy-pyridin-2-yl)-methanol

To a solution of (5-bromo-pyridin-2-yl)-methanol (1.0 eq.) in CH₂Cl₂ (0.2M) was added peracetic acid (3.0 eq.). The mixture was stirred for 12 h, diluted with CH₂Cl₂ and neutralized with aqueous NaOH (1M) to pH=7. The organic phase was decanted, dried over Na₂SO₄ and upon concentration the title compound crystallized as a white solid and was isolated by filtration.

Step 4: 5-Bromo-2-methoxymethyl-pyridine 1-oxide

To a solution of (5-bromo-1-oxy-pyridin-2-yl)methanol (1.0 eq.) in THF:DMF (1:1; 0.2M) was added t-BuOK (1.0M in THF; 1.1 eq.). The mixture was stirred for 1 h, cooled to −78° C. then MeI (1.1 eq.) was added. The final mixture was warmed to rt, poured in saturated aqueous NH₄Cl and extracted with EtOAc (2×). The combined organic extracts were washed with brine, dried over Na₂SO₄, filtered and concentrated to afforded a mixture of the title compound and the starting material (20%) which was used as such.

Step 5: EXAMPLE 26

A mixture of Quinoline 4 (1.2 eq.), 5-bromo-2-methoxymethyl-pyridine 1-oxide (1.0 eq.), PdCl₂(dppf)₂ (0.0 5eq.) and aqueous Na₂CO₃ (2M; 2.5 eq.) in n-propanol (0.2M) was stirred at 80° C. for 4 h. The mixture was cooled, poured in brine and extracted with EtOAc (2×). The combined organic extracts were dried over Na₂SO₄, filtered and concentrated. Flash chromatography (EtOAc:MeOH; 9:1) afforded the title compound as a light yellow solid. ¹H NMR (500 MHz, DMSO-d₆): δ 8.95 (dd, 1H), 8.72 (s, 1H), 8.54 (dd, 1H), 8.30 (d, 1H), 8.08 (d, 1H), 7.98 (s, 1H), 7.79 (t, 1H), 7.77 (d, 1H), 7.75 (s, 1H), 7.66–7.62 (m, 2H), 7.56 (d, 1H), 4.62 (s, 2H), 3.48 (s, 3H), 2.51 (s, 3H), 1.95 (s, 6H).

EXAMPLE 27

2-(5-{3-[6-(1-Methanesulfonyl-1-methyl-ethyl)-quinolin-8-yl]-phenyl}-3-methyl-1-oxy-pyridin-2-yl)-propan-2-ol

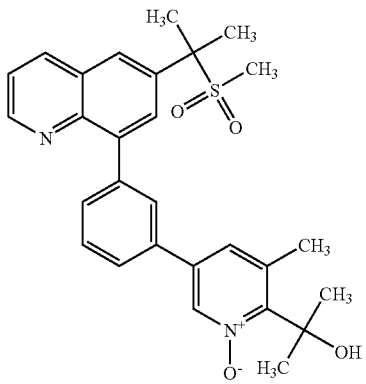

Step 1: 2,5-Dibromo-3-methyl-pyridine

5-Bromo-3-methyl-pyridin-2-ylamine (1.0 eq.) was added portionwise to aqueous HBr (48%; 1.0M). The mixture was stirred 1 h at rt then cooled to −20° C. Bromine (2.8 eq.) was added dropwise followed by a aqueous solution of NaNO₂ (1.0M; 2.7 eq.). The final mixture was warmed to rt and stirred for 2 h. The mixture was cooled back to −20° C. then aqueous NaOH (1.0M; 3.0 eq.) was added dropwise over 1 h. The final mixture was warmed to rt and extracted with Et₂O (2×). The combined organic extracts were washed with brine, dried over MgSO₄, filtered and concentrated to afford the title compound as a yellow solid.

Step 2: 2-(5-Bromo-3-methyl-pyridin-2-yl)-propan-2-ol

Prepared according to the procedure described in EXAMPLE 16 (Step 1) but using 2,5-dibromo-3-methyl-pyridine from Step 1 as starting material. Flash chromatography (Hex:EtOAc; 9:1) afforded the title compound as a white solid.

Step 3: 2-(5-Bromo-3-methyl-1-oxy-pyridin-2-yl)-propan-2-ol

Prepared according to the procedure described in EXAMPEL 9 (Step 4) but using 2-(5-bromo-3-methyl-pyridin-2-yl)-propan-2-ol from Step 2 as starting material. Flash chromatography (Hex:EtOAc; 1:1) afforded the title compound as a white solid.

Step 4: EXAMPLE 27

Prepared according to the procedure described in EXAMPLE 6 (Step 2) but using (5-bromo-3-methyl-1-oxy-pyridin-2-yl)-propan-2-ol from Step 3 as starting material. Flash chromatography (EtOAc) afforded the title compound as a white solid. ¹H NMR (500 MHz, CDCl₃): δ 9.53 (s, OH), 9.00 (dd, 1H), 8.49 (d, H), 8.29 (dd, 1H), 8.10 (d, 2H), 7.90 (s, 1H), 7.78 (d, 1H), 7.64 (m, 2H), 7.52 (dd, 1H), 7.46 (d, 1H), 2.67 (s, 3H), 2.60 (s, 3H), 2.04 (s, 6H), 1.80 (s, 6H).

EXAMPLE 28

1,1-Difluoro-1-(5-{3-[6-(1-methanesulfonyl-1-methyl-ethyl)-quinolin-8-yl]-phenyl}-pyridin-3-ylsulfanyl)-propan-2-ol

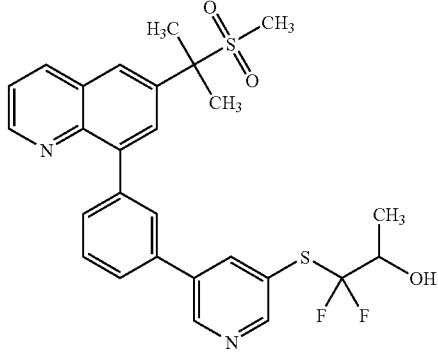

Step 1: Difluoro-(5-{3-[6-(1-methanesulfonyl-1-methyl-ethyl)-quinolin-8-yl]-phenyl}-pyridin-3-yl-sulfanyl)-acetic acid ethyl ester Prepared according to the procedure described in EXAMPLE 24 (Step 5) but using 6-(1-methanesulfonyl-1-methyl-ethyl)-8-{3-[5-(2-trimethylsilanyl-ethylsulfanyl)-pyridin-3-yl]-phenyl}-quinoline from EXAMPLE 24 (Step 2) and bromo-difluoro-acetic acid ethyl ester as starting materials. Flash chromatography (Hex:EtOAc; 1:4) and stirring in Hex:Et₂O afforded the title compound as a white solid after filtration.

Step 2: EXAMPLE 28

To a solution of difluoro-(5-{3-[6-(1-methanesulfonyl-1-methyl-ethyl)-quinolin-8-yl]-phenyl}-pyridin-3-ylsulfanyl)-acetic acid ethyl ester from Step 1 (1.0 eq.) in CH₂Cl₂ (0.2M) at −78° C. was added MeMgBr (3.0 eq.; 3.0M in Et₂O). The mixture was warmed to rt, stirred for 12 h, poured in saturated aqueous NH₄Cl and extracted with EtOAc (2×). The combined organic extracts were washed with brine, dried over Na₂SO₄, filtered and concentrated. The residue was dissolved in EtOH (0.2M) then NaBH₄ (3.0 eq.) was added. The mixture was stirred for 2 h, poured in saturated aqueous NH₄Cl and extracted with EtOAc (2×). The combined organic extracts were washed with brine, dried over Na₂SO₄, filtered and concentrated. Flash chromatography (Hex:EtOAc; 1:9) afforded the title compound as a white solid. ¹H NMR (400 MHz, acetone-d₆): δ 9.04 (d, 1H), 8.97 (dd, 1H), 8.75 (d, 1H), 8.50 (d, 1H), 8.35–8.34 (m, 2H), 8.26 (d, 1H), 8.13 (s, 1H), 7.85 (dt, 1H), 7.82 (dt, 1H), 7.68 (t, 1H), 7.61 (dd, 1H), 5.15 (d, 1H), 4.20 (m, 1H), 2.76 (s, 3H), 2.03 (s, 6H), 1.37 (d, 3H).

EXAMPLE 29

6-(1-Methanesulfonyl-1-methyl-ethyl)-8-[3-(1-oxy-quinolin-3-yl)-phenyl]-quinoline

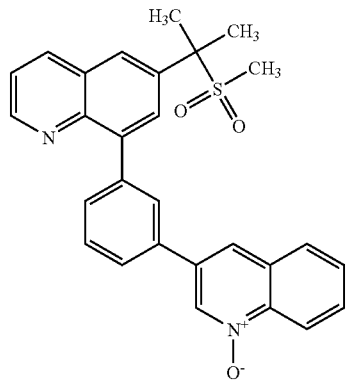

Step 1: 3-Bromo-quinoline 1-oxide

To a solution of 3-bromo-quinoline (1.0 eq.) in CH₂Cl₂ (0.2M) was added peracetic acid (2.0 eq.). The mixture was stirred for 12 h, poured in saturated aqueous NaHCO₃ and extracted with EtOAc (2×). The combined organic extracts were washed with brine, dried over Na₂SO₄, filtered and concentrated. Crystallization from CH₂Cl₂:Hex afforded the title compound as a white solid.

Step 2: EXAMPLE 29

Prepared according to the procedure described in EXAMPLE 6 (Step 2) but using 3-bromo-quinoline 1-oxide as starting material. Flash chromatography (EtOAc:MeOH; 95:5) afforded the title compound as a white solid. ¹H NMR (500 MHz, CDCl₃): δ 8.99 (d, 1H), 8.93 (s, 1H), 8.75 (d, 1H), 8.29 (dd, 1H), 8.12 (s, 2H), 8.03 (s, 1H), 7.99 (s, 1H), 7.92 (d, 1H), 7.75 (m, 3H), 7.67 (m, 2H), 7.51 (dd, 1H), 2.66 (s, 3H), 2.03 (s, 6H).

EXAMPLE 30

1-Isopropyl-3-(5-{3-[6-(1-methanesulfonyl-1-methyl-ethyl)-quinolin-8-yl]-phenyl}-1-oxy-pyridin-2-yl)-urea

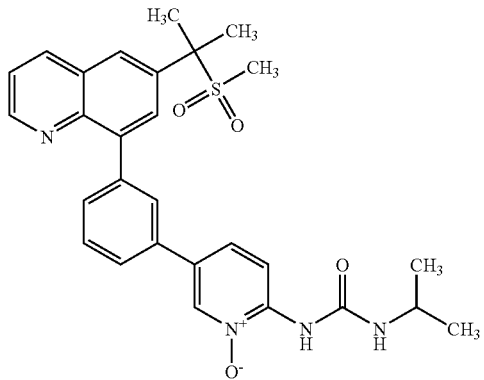

Step 1: 1-(5-Bromo-pyridin-2-yl)-3-isopropyl-urea

To a solution of 2-amino-5-bromo-pyridine (1.05 eq.) in TBF (0.2M) was added DBU (1.0 eq.) followed by isopropyl-isocyanate (1.0 eq.). The mixture was stirred for 12 h, diluted with CH$_2$Cl$_2$, washed with brine, dried over MgSO$_4$, filtered and concentrated. Crystallization from acetone afforded the title compound as a white solid.

Step 2: 1-(5-Bromo-1-oxy-pyridin-2-yl)-3-isopropyl-urea

Prepared according to the procedure described in EXAMPLE 29 (Step 1) but using 1-(5-bromo-pyridin-2-yl)-3-isopropyl-urea from Step 1 as starting material. Crystallization from acetone afforded the title compound as a white solid.

Step 3: EXAMPLE 30

Prepared according to the procedure described in EXAMPLE 6 (Step 2) but using 1-(5-bromo-1-oxy-pyridin-2-yl)-3-isopropyl-urea from Step 2 as starting material. Flash chromatography (EtOAc:MeOH; 9:1) and stirring in acetone afforded the title compound as a white solid after filtration. $^1$H NMR (500 MHz, CDCl$_3$): δ 10.05 (s, NH), 8.98 (d, 1H), 8.59 (d, 1H), 8.41 (s, 1H), 8.29 (d, 1H), 8.09 (d, 2H), 7.88 (s, 1H), 7.70 (m, 3H), 7.55 (m, 3H), 3.96 (m, 1H), 2.65 (s, 3H), 2.01 (s, 6H), 1.20 (s, 6H).

EXAMPLE 31

6-(1-Methanesulfonyl-1-methyl-ethyl)-8-[3-(3-methyl-[1,2,4]oxadiazol-5-yl)-phenyl]-quinoline

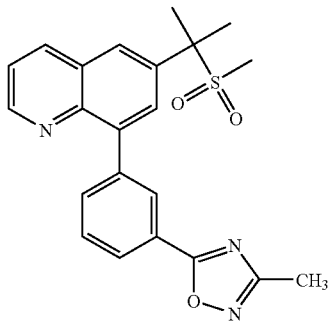

Step 1: 3-[6-(1-Methanesulfonyl-1-methyl-ethyl)-quinolin-8-yl]-benzoic acid methyl ester To a solution of 3-[6-(1-methanesulfonyl-1-methyl-ethyl)-quinolin-8-yl]-benzaldehyde (1.0 eq.) (see WO-0146151) in CH$_2$Cl$_2$:MeOH (1:1; 0.1M) was added NaCN (1.8 eq.), MnO$_2$ (8.0 eq.) and AcOH (0.05 eq.). The mixture was stirred for 12 h, filtered on celite, and concentrated. Flash chromatography (Hex:EtOAc; 1:1) afforded the title compound as a white solid.

Step 2: 3-[6-(1-Methanesulfonyl-1-methyl-ethyl)-quinolin-8-yl]-benzoic acid

To a solution of 3-[6-(1-methanesulfonyl-1-methyl-ethyl)-quinolin-8-yl]-benzoic acid methyl ester from Step 1 (1.0 eq.) in THF (0.2M) was added aqueous LiOH (1.0M; 3.0 eq.). The mixture was stirred for 5 h at 60° C., neutralized to pH=5 using aqueous HCl (1M) and extracted with CH$_2$Cl$_2$ (4×). The combined organic extracts were dried over MgSO$_4$, filtered and concentrated. Stirring in Hex:Et$_2$O (1:1) afforded the title compound after filtration.

Step 3: EXAMPLE 31

To a solution of-[6-(1-methanesulfonyl-1-methyl-ethyl)-quinolin-8-yl]-benzoic acid from Step 2 (1.0 eq.) in DMF (0.1M) was added CDI (2.0 eq.) and N-hydroxy-acetamidine (2.0 eq.). The mixture was stirred for 1 h at rt then 12 h at 120° C. The mixture was cooled, poured in water and extracted with EtOAc. The organic extract was washed with water (2×), brine, dried over Na$_2$SO$_4$, filtered and concentrated. Flash chromatography (Hex:EtOAc; 9:1 to 1:9 in 20 min) afforded the title compound as a white solid. $^1$H NMR (500 MHz, acetone-d$_6$): δ 8.91 (dd, 1H), 8.52 (m, 3H), 8.38 (d, 1H), 8.25 (d, 1H), 8.04 (d, 1H), 7.78 (t, 1H), 7.64 (dd, 1H), 2.77 (s, 3H), 2.43 (s, 3H), 2.05 (s, 6H).

EXAMPLE 32

8-(3-{5-[Difluoro-(3-methyl-[1,2,4]oxadiazol-5-yl)-methylsulfanyl]-pyridin-3-yl}-phenyl)-6-(1-methanesulfonyl-1-methyl-ethyl)-quinoline

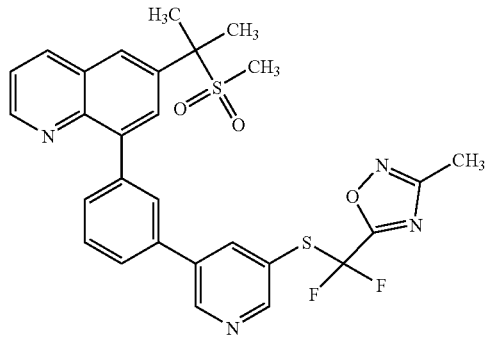

Step 1: Difluoro-(5-{3-[6-(1-methanesulfonyl-1-methyl-ethyl)-quinolin-8-yl]-phenyl}-pyridin-3-yl-sulfanyl)-acetic acid Prepared according to the procedure described in EXAMPLE 31 (Step 2) but using difluoro-(5-{3-[6-(1-methanesulfonyl-1-methyl-ethyl)-quinolin-8-yl]-phenyl}-pyridin-3-ylsulfanyl)-acetic acid ethyl ester from EXAMPLE 28 (Step 1) as starting material.

Step 2: EXAMPLE 32

Prepared according to the procedure described in EXAMPLE 31 (Step 3) but using difluoro-(5-{3-[6-(1-methanesulfonyl-1-methyl-ethyl)-quinolin-8-yl]-phenyl}-pyridin-3-ylsulfanyl)-acetic acid from Step 1 as starting material. Flash chromatography (Hex:AcOEt; 1:4) afforded the title compound as a white solid. $^1$H NMR (500 MHz, acetone-d$_6$): δ 9.07 (d, 1H), 8.97 (dd, 1H), 8.76 (d, 1H), 8.51 (dd, 1H), 8.37 (t, 1H), 8.35 (d, 1H), 8.26 (d, 1H), 8.17 (s, 1H), 7.85 (t, 2H), 7.70 (t, 1H), 7.62 (dd, 1H), 2.78 (s, 3H), 2.28 (s, 3H), 2.05 (s, 6H).

EXAMPLE 33

N-Cyclopropyl-3-(5-{3-[6-(1-methanesulfonyl-1-methyl-ethyl)-quinolin-8-yl]-phenyl}-pyridin-3-yl)-acrylamide

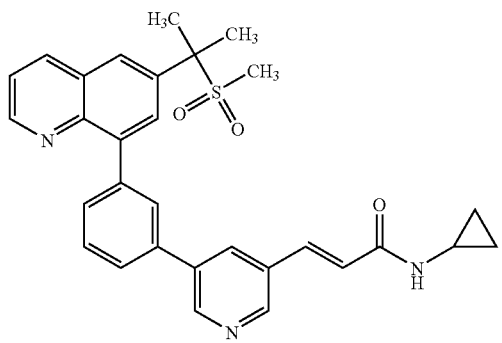

Step 1: 5-Bromo-pyridine-3-carbaldehyde

To a solution of 3,5-dibromopyridine (1.0 eq.) in Et$_2$O (0.1M) at −78° C. was added n-BuLi (1.05 eq.). The mixture was stirred for 30 min at −78° C. then DMF (3.0 eq.) was added. The final mixture was warmed to rt, stirred for 3 h, quenched using saturated aqueous NH$_4$Cl and extracted with EtOAc (2×). The combined organic extracts were washed with brine, dried over MgSO$_4$, filtered and concentrated. Flash chromatography (Hex:EtOAc; 4:1) afforded the title compound as an oil.

Step 2: 3-(5-Bromo-pyridin-3-yl)-acrylic acid

Prepared according to the procedure described in Example 11 (Step 2) but using 5-bromo-pyridine-3-carbaldehyde from Step 1 as starting material.

Step 3: 3-(5-Bromo-pyridin-3-yl)-N-cyclopropyl-acrylamide

Prepared according to the procedure described in Example 11 (Step 3) but using 3-(5-bromo-pyridin-3-yl)-acrylic acid from Step 2 as starting material. Crystallization in CH$_2$Cl$_2$ afforded the title compound.

Step 4: EXAMPLE 33

Prepared according to the procedure described in EXAMPLE 6 (Step 2) but using 3-(5-bromo-pyridin-3-yl)-N-cyclopropyl-acrylamide from Step 3 as starting material. Flash chromatography (EtOAc:EtOH; 9:1) afforded the title compound as a white solid. $^1$H NMR (500 MHz, acetone-d$_6$): δ 8.98 (dd, 1H), 8.80 (d, 1H), 8.60 (d, 1H), 8.33 (dd, 1H), 8.07 (d, 2H), 8.01 (s, 1H), 7.89 (s, 1H), 7.73 (d, 1H), 7.60 (m, 3H), 7.45 (dd, 1H), 6.58 (d, 1H), 6.55 (s, NH), 2.80 (m, 1H), 2.65 (s, 3H), 1.98 (s, 6H), 0.75 (m, 2H), 0.55 (m, 2H).

EXAMPLE 34

N-Cyclopropyl-2-(5-{3-[6-(1-methanesulfonyl-1-methylethyl)-quinolin-8-yl]-phenyl}-pyridin-3-yl)-acetamide

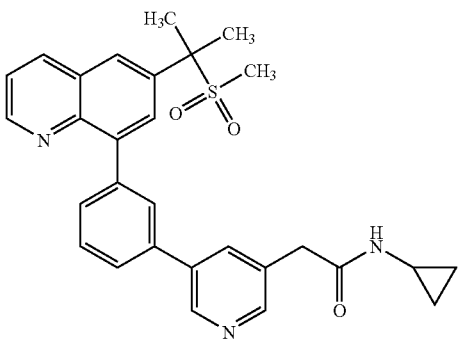

Step 1: 2-(5-Bromo-pyridin-3-yl)-N-cyclopropyl-acetamide

Prepared according to the procedure described in EXAMPLE 11 (Step 3) but using (5-bromo-pyridin-3-yl)-acetic acid as starting material. Crystallization in CH$_2$Cl$_2$ afforded the title compound.

Step 2: EXAMPLE 34

Prepared according to the procedure described in EXAMPLE 6 (Step 2) but using 2-(5-bromo-pyridin-3-yl)-N-cyclopropyl-acetamide from Step 1 as starting material. Flash chromatography (EtOAc:EtOH; 9:1) afforded the title compound as a white solid. $^1$H NMR (500 MHz, acetone-d$_6$): δ 8.92 (dd, 1H), 8.79 (d, 1H), 8.47 (s, 1H), 8.45 (d, 1H), 8.30 (d, 1H), 8.21 (d, 1H), 8.04 (s, 1H), 8.00 (s, 1H), 7.75 (d, 1H), 7.72 (d, 1H), 7.62 (t, 1H), 7.57 (dd, 1H), 7.41 (br s, NH), 3.54 (s, 2H), 2.72 (s, 3H), 2.68 (m, 1H), 2.00 (s, 6H), 0.61 (m, 2H), 0.40 (m, 2H).

EXAMPLE 35

(5-{3-[6-(1-Methanesulfonyl-1-methylethyl)quinolin-8-yl]-phenyl}pyridin-2-yl)-(4-methoxy-phenyl)-methanone

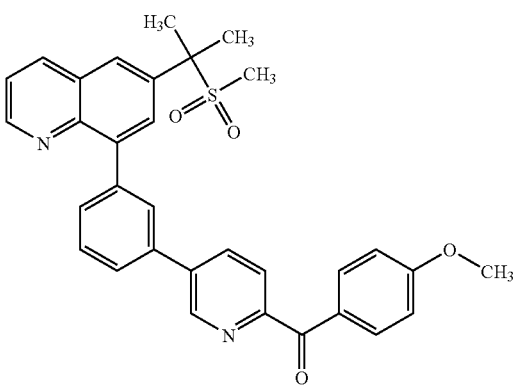

Step 1: (5-Bromo-pyridin-2-yl)-(4-methoxy-phenyl)-methanol

To a solution of 2,5-dibromopyridine (1.0 eq.) in Tol (0.1M) at −78° C. was added n-BuUi (1.05 eq.). The mixture was stirred for 2 h at −78° C. then 4-methoxy-benzaldehyde (1.1 eq.) was added. The final mixture was warmed 0° C., poured in saturated aqueous $NH_4Cl$ and extracted with $Et_2O$ (2×). The combined organic extracts were washed with brine, dried over $MgSO_4$, filtered and concentrated. Flash chromatography (Hex:EtOAc; 9:1 to 3:2) and stirring in Hex:$Et_2O$ afforded the title compound as a white solid after filtration.

Step 2: (5-Bromo-pyridin-2-yl)-(4-methoxy-phenyl)-methanone

To a solution of (5-bromo-pyridin-2-yl)-(4-methoxy-phenyl)-methanol (1.0 eq.) in EtOAc (0.2M) was added $MnO_2$ (3.0 eq.). The mixture was stirred for 1 h, filtered on celite and concentrated to afford the title compound as a white solid.

Step 3: EXAMPLE 35

Prepared according to the procedure described in EXAMPLE 6 (Step 2) but using (5-bromo-pyridin-2-yl)-(4-methoxy-phenyl)-methanone from Step 2 as starting material. Flash chromatography (Hex:EtOAc; 9:1 to 1:4) afforded the title compound as a foam. $^1$H NMR (500 MHz, acetone-$d_6$): δ 9.08 (d, 1H), 8.96 (dd, 1H), 8.48 (dd, 1H), 8.36 (dd, 1H), 8.32 (d, 1H), 8.26–8.19 (m, 4H), 8.09 (s, 1H), 7.86 (t, 2H), 7.68 (t, 1H), 7.60 (dd, 1H), 7.06 (d, 2H), 3.9 (s, 3H), 2.74 (s, 3H), 2.01 (s, 6H).

EXAMPLE 36

8-[3-(4—Chloro-1-oxy-pyridin-3-yl)-phenyl]-6-(1-methanesulfonyl-1-methyl-ethyl)-quinoline

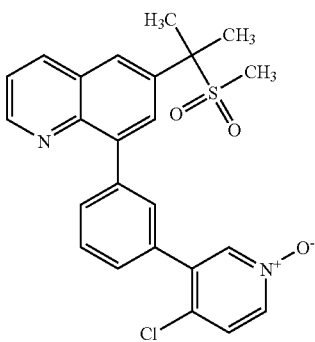

Step 1: 4—Chloro-3-tributylstannanyl-pyridine

To a solution of LDA (1.2 eq.) in THF (0.2M) at −78° C. was added 4-chloro-pyridine (1.0 eq.). The mixture was stirred for 1.5 h at −78° C. then $Bu_3SnCl$ (1.5 eq.) was added. The final mixture was slowly warmed to rt, poured in saturated aqueous $NH_4Cl$ and extracted with EtOAc (2×). The combined organic extracts were washed with brine, dried over $Na_2SO_4$, filtered and concentrated. Flash chromatography (Hex:EtOAc; 95:5) afforded the title compound as an oil.

Step 2: 8-[3-(4—Chloro-pyridin-3-yl)-phenyl]-6-(1-methanesulfonyl-1-methyl-ethyl)-quinoline A mixture of Quinoline 3 (1.0 eq.), 4-chloro-3-tributylstannanyl-pyridine (2.0 eq.), $PdCl_2(dppf)_2$ (0.05 eq.), CuI (0.05 eq.) in dioxane (0.1M) was refluxed for 12 h, cooled to rt and concentrated. Flash chromatography ($CH_2Cl_2$:MeOH; 99:1) afforded the title compound as a beige foam.

Step 3: EXAMPLE 36

Prepared according to the procedure described in EXAMPLE 9 (Step 4) but using 8-[3-(4-chloro-pyridin-3-yl)-phenyl]-6-(1-methanesulfonyl-1-methyl-ethyl)-quinoline from Step 2 as starting material. Flash chromatography ($CH_2Cl_2$:MeOH; 95:5) afforded the title compound as a white solid. $^1$H NMR (500 MHz, acetone-$d_6$): δ 8.96 (dd, 1H), 8.49 (d, 1H), 8.33 (dd, 2H), 8.26 (d, 1H), 8.19 (dd, 1H), 7.96 (s, 1H), 7.93 (d, 1H), 7.67 (t, 1H), 7.62 (m, 1H), 2.76 (s, 3H), 2.05 (s, 6H).

EXAMPLE 37

8-[3-(3H-Imidazo[4,5-b]pyridin-6-yl)-phenyl]-6-(1-methanesulfonyl-1-methyl-ethyl)-quinoline

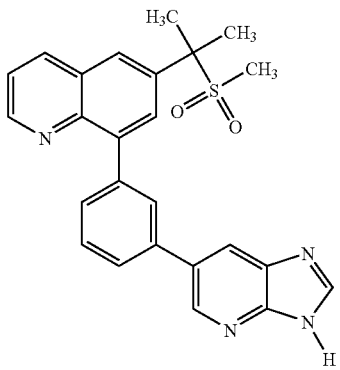

Step 1: 6-Bromo-3-(2-trimethylsilanyl-ethoxymethyl)-3H-imidazo[4,5-b]pyridine To a solution of 6-bromo-3H-imidazo[4,5-b]pyridine (1.0 eq.) (see *J. Am. Chem. Soc.* 1957, 6421.) in DMF (0.2M) was added NaH (1.4 eq.). The mixture was stirred for 30 min then SEM-Cl (2.0 eq.) was added. The final mixture was stirred for 2 h, poured in saturated aqueous $NH_4Cl$ and extracted with EtOAc (2×). The combined organic extracts were washed with water (3×), brine, dried over $Na2SO_4$, filtered and concentrated. Flash chromatography (Hex:EtOAc; 7:3) afforded the title compound as a foam.

Step 2: 6-(1-Methanesulfonyl-1-methyl-ethyl)-8-{3-[3-(2-trimethylsilanyl-ethoxymethyl)-3H-imidazo[4,5-b]pyridin-6-yl]-phenyl}quinoline Prepared according to the procedure described in EXAMPLE 6 (Step 2) but using 6-bromo-3-(2-trimethylsilanyl-ethoxymethyl)-3H-imidazo[4,5-b]pyridine from Step 1 as starting material. Flash chromatography (Hex:EtOAc; 2:1 to 1:1) afforded the title compound as a foam.

Step 3: EXAMPLE 37

A mixture of 6-(1-methanesulfonyl-1-methyl-ethyl)-8-{3-[3-(2-trimethylsilanyl-ethoxymethyl)-3H-imidazo[4,5-b] pyridin-6-yl]-phenyl}-quinoline from Step 2 (1.0 eq.), TBAF (2.0 eq.) and ethylene diamine (1.5 eq.) in DMF (0.2M) was stirred at 80° C. for 3 h. The mixture was cooled, diluted with water, filtered. The resulting solid was stirred in acetone to afford the title compound after filtration. $^1$H NMR (500 MHz, DMSO-$d_6$): δ 8.94 (dd, 1H), 8.72 (s, 1H), 8.52 (dd, 1H), 8.47 (s, 1H), 8.30–8.25 (m, 2H), 8.08 (d, 1H), 7.98 (s, 1H), 7.79 (d, 1H), 7.68 (d, 1H), 7.63–7.60 (m, 2H), 2.81 (s, 3H), 1.93 (s, 6H).

EXAMPLE 38

N-Cyclopropyl-3-(3-{5-[6-(1-methanesulfonyl-1-methyl-ethyl)-quinolin-8-yl]-1-oxy-pyridin-3-yl}-phenyl)-acrylamide

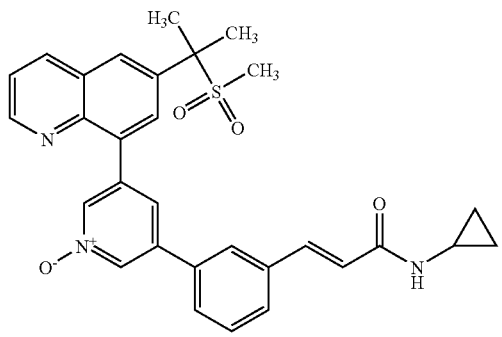

Step 1: 8-(5-Bromo-pyridin-3-yl)-6-(1-methanesulfonyl-1-methyl-ethyl)-quinoline

To a solution of 3,5-dibromo-pyridine (1.2 eq.) in Et$_2$O (0.1M) at −78° C. was added dropwise sec-BuLi (1.05 eq.). The mixture was stirred for 30 min then tri-isopropyl boronate (1.5 eq.) was added. The final mixture was warm to rt, diluted with iso-propanol and concentrated. To the residue in n-propanol (0.1M) was added Quinoline 3 (1.0 eq.), Na$_2$CO$_3$ (2M in H$_2$O; 3.5 eq.), Pd(OAc)$_2$ (0.05 eq.) and PPh$_3$ (0.15 eq). The mixture was stirred at 80° C. for 2 h, cooled to rt, poured in saturated aqueous NH$_4$Cl and extracted with EtOAc (2×). The combined organic extracts were washed with brine, dried over Na$_2$SO$_4$, filtered and concentrated. Flash chromatography (CH$_2$Cl$_2$:EtOAc; 1:1 to 0:1) afforded the title compound as a white solid.

Step 2: 8-(5-Bromo-1-oxy-pyridin-3-yl)-6-(1-methanesulfonyl-1-methyl-ethyl)-quinoline Prepared according to the procedure described in EXAMPLE 9 (Step 4) but using 8-(5-bromo-pyridin-3-yl)-6-(1-methanesulfonyl-1-methyl-ethyl)-quinoline from Step 1 as starting material. Flash chromatography (EtOAc:EtOH; 4:1) afforded the title compound as a white solid.

Step 3: 3-(3-{5-[6-(1-Methanesulfonyl-1-methyl-ethyl)-quinolin-8-yl]-1-oxy-pyridin-3-yl}-phenyl)-acrylic acid Prepared according to the procedure described in EXAMPLE 6 (Step 2) but using 3-(2-carboxy-vinyl)phenyl boronic acid and 8-(5-Bromo-1-oxy-pyridin-3-yl)-6-(1-methanesulfonyl-1-methyl-ethyl)-quinoline from Step 2 as starting materials. Flash chromatography (EtOAc:EtOH; 9:1) and stirring in CH$_2$Cl$_2$:Hex afforded the title compound as a white solid after filtration.

Step 4: EXAMPLE 38

Prepared according to the procedure described in EXAMPLE 11 (Step 3) but using -(3-{5-[6-(1-methanesulfonyl-1-methyl-ethyl)-quinolin-8-yl]-1-oxy-pyridin-3-yl}-phenyl)-acrylic acid from Step 3 as starting material. Flash chromatography (EtOAc:EtOH; 4:1) afforded the title compound as a white solid. $^1$H NMR (500 MHz, CDCl$_3$): δ 8.95 (dd, 1H), 8.65 (s, 1H), 8.48 (s, 1H), 8.27 (d, 1H), 8.12 (m, 2H), 7.80 (s, 1H), 7.72 (s, 1H), 7.61 (d, 1H), 7.50 (m, 4H), 6.48 (d, 1H), 6.20 (br s, NH), 2.86 (m, 1H), 2.70 (s, 3H), 2.03 (s, 6H), 0.82 (m, 2H), 0.57 (m, 2H).

EXAMPLE 39

8-[3-(3—Chloro-pyrazin-2-yl)-phenyl]-6-(1-methanesulfonyl-1-methyl-ethyl)-quinoline

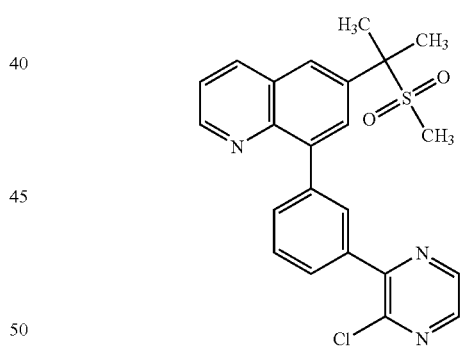

A mixture of Quinoline 4 (1.0 eq.), 2,3-dichloro-pyrazine (3.0 eq.), Pd(IMes)$_2$ (0.05 eq.) and Na$_2$CO$_3$ (2M, 3.5 eq.) in 1,4-dioxane (0.2M) was stirred at 100° C. for 2 h. The mixture was cooled to rt, poured in saturated aqueous NH$_4$Cl and extracted with EtOAc (2×). The combined organic extracts were washed with brine, dried over Na$_2$SO$_4$, filtered and concentrated. Flash chromatography (Hex:EtOAc; 7:3) afforded the title compound as a white solid. $^1$H NMR (500 MHz, acetone-$d_6$): δ 8.94 (dd, 1H), 8.72 (d, 1H), 8.47 (m, 1H), 8.46 (dd, 1H), 8.32 (d, 1H), 8.25 (m, 2H), 7.92 (d, 1H), 7.89 (d, 1H), 7.66 (t, 1H), 7.57 (dd, 1H), 2.74 (s, 3H), 2.02 (s, 6H).

EXAMPLE 40

8-(3-Benzo[1,2,5]oxadiazol-5-yl-phenyl)-6-(1-methanesulfonyl-1-methyl-ethyl)-quinoline

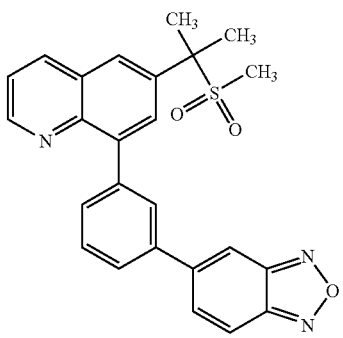

Prepared according to the procedure described in EXAMPLE 3, but using 5-Bromo-benzo[1,2,5]oxadiazole (*Biorg. Med. Chem. Lett.* 2002, 233) as starting material. The reaction mixture was stirred 12 h at 80° C. Flash chromatography (Hex:EtOAc 5 to 50% in 20 min) and crystallization in Hex:EtOAc afforded the title compound as a white solid. $^1$H NMR (500 MHz, acetone-$d_6$): δ 8.98 (dd, 1H), 8.52 (dd, 1H), 8.35 (d, 1H), 8.28 (d, 1H), 8;26 (t, 1H), 8.23 (t, 1H), 8.11 (dd, 1H), 8.08 (dd, 1H), 7.93 (dd, 1H), 7.89 (dd, 1H), 7.71 (t, 1H), 7.63 (dd, 1H), 2.76 (s, 3H), 2.04 (s, 6H).

EXAMPLE 41

N-(5-{3-[6-(1-Methanesulfonyl-1-methyl-ethyl)-quinolin-8-yl]-phenyl}-1-oxy-pyridin-2-yl)-acetamide

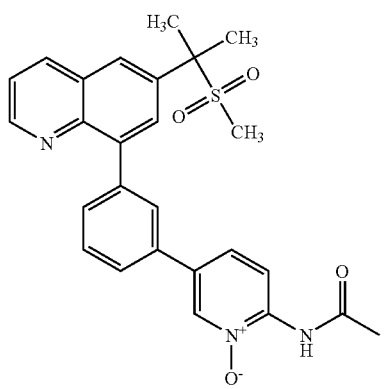

Step 1: N-(5-Bromo-pyridin-2-yl)-acetamide

To a solution of 5-bromo-pyridin-2-ylamine (1.0 eq.), Net$_3$ (1.2 eq.) in CH$_2$Cl$_2$ (0.1M) was added AcCl (1.2 eq.). The mixture was stirred 1 h at rt, poured in saturated aqueous NH$_4$Cl and extracted with EtOAc (2×). The combined organic extracts were washed with brine, dried over Na$_2$SO$_4$, filtered and concentrated. Flash chromatography (CH$_2$Cl$_2$:EtOAc; 85:15) afforded the title compound as a white solid.

Step 2: N-(5-Bromo-1-oxy-pyridin-2-yl)-acetamide

Prepared according to the procedure described in EXAMPLE 9, Step 4, but using N-(5-bromo-pyridin-2-yl)-acetamide from Step 1 as starting material. Flash chromatography (EtOAc) afforded the title compound as a white solid.

Step 3: EXAMPLE 41

Prepared according to the procedure described in EXAMPLE 6, Step 2, but using N-(5-bromo-1-oxy-pyridin-2-yl)-acetamide from Step 2 as starting material. The reaction mixture was stirred 1.5 h at 90° C. Flash chromatography (EtOAc:EtOH; 85:15) afforded the title compound as a white solid. $^1$H NMR (500 MHz, acetone-$d_6$): δ 10.15 (s, NH), 8.94 (dd, 1H), 8.60 (d, 1H), 8.49-8.43 (m, 2H), 8.32 (d, 1H), 8.21 (d, 1H), 8.06 (s, 1H), 7.80–7.73 (m, 3H), 7.65–7.57 (m, 2H), 2.72 (s, 3H), 2.36 (s, 3H), 2.01 (s, 6H).

EXAMPLE 42

2-{3'-[6-(1-Methanesulfonyl-1-methyl-ethyl)-quinolin-8-yl]-biphenyl-4-yl}-cyclopropanecarboxylic acid

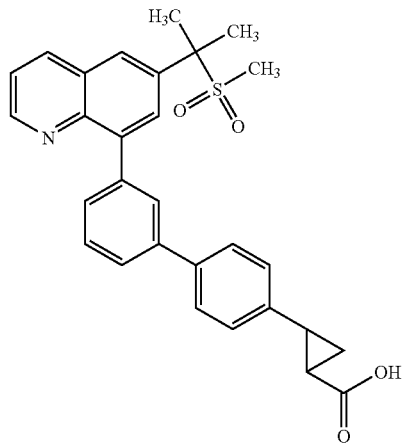

Step 1: Trans-2-(4-Bromo-phenyl)-cyclopropanecarboxylic acid ethyl ester

To a solution of E-3-(4-bromo-phenyl)-acrylic acid ethyl ester and Pd(OAc)$_2$ (0.05 eq.) in THF (0.2M) was added portionwise CH$_2$N$_2$ until the reaction was completed. NMR of aliquots monitored the reaction. The resulting mixture was concentrated and filtered on celite to afford the title compound as an oil.

Step 2: Trans-2-{3'-[6-(1-Methanesulfonyl-1-methyl-ethyl)-quinolin-8-yl]-biphenyl-4-yl)}-cyclopropanecarboxylic acid ethyl ester Prepared according to the procedure described in EXAMPLE 6, Step 2, but using 2-(4-bromo-phenyl)-cyclopropanecarboxylic acid ethyl ester from Step 2 as starting material. The reaction mixture was stirred 2 h at 100° C. Flash chromatography (Hex:EtOAc 3:2) afforded the title compound as a foam.

Step 3: EXAMPLE 42

To a solution of 2-{3'[6-(1-methanesulfonyl-1-methyl-ethyl)-quinolin-8-yl]-biphenyl 4-yl}-cyclopropanecarboxylic acid ethyl ester (1.0 eq.) from Step 1, in THF:MEOH (2:1; 0.2M) was added aqueous LiOH (2M; 0.2.0 eq.). The mixture was stirred for 12 h at rt, quenched with HCl 10% and extracted with EtOAc (2×). The combined organic extracts were washed with brine, dried over $Na_2SO_4$, filtered and concentrated. Crystallization in Hex:EtOAc afforded the title compound as a white solid. $^1H$ NMR (400 MD, acetone-$d_6$): δ 8.96 (dd, 1H), 8.50 (dd, 1H), 8.32 (d, 1H), 8.24 (d, 1H), 8.03 (t, 1H), 7.73–7.68 (m, 4H), 7.63–7.59 (m, 2H), 7.32 (d, 2H), 2.75 (s, 3H), 2.53 (m, 1H), 2.03 (s, 6H), 1.97 (m, 1H), 1.56 (m, 1H), 1.46 (m, 1H).

The enantiomers of EXAMPLE 42 were isolated separately by the following procedure.

Step 4: E-3-(4-Bromo-phenyl)-1-imidazol-1-yl-propenone

To a solution of E-3-(4-Bromo-phenyl)-acrylic acid (1.0 eq.) in toluene (0.2M) was added CDI (1.5 eq.). The mixture was stirred for 3 h at rt. The resulting precipitate was isolated by filtration to afford the title compound as a white solid.

Step 5: E-3-[3-(4-Bromo-phenyl)-acryloyl]-4-methyl-5-phenyl-oxazolidin-2-one

A mixture of 3-(4-Bromo-phenyl)-1-imidazol-1-yl-propenone (1.05 eq.) from Step 4, (4R,5S)-(+)-4-methyl-5-phenyl-2-oxazolidinone (1.0 eq.) and Et3N (1.2 eq) in $CH_3CN$ (0.2M) was reflux overnight. The resulting mixture was cooled to rt, filtered on a pad of silica gel and concentrated. Crystallization in Hex:$Et_2O$ afforded the title compound as a white solid.

Step 6: Trans-3-[2-(4-Bromo-phenyl)-cyclopropanecarbonyl]-4-methyl-5-phenyl-oxazolidin-2-one To a solution of E-3-[3-(4-Bromo-phenyl)-acryloyl]4-methyl-5-phenyl-oxazolidin-2-one from Step 5 and Pd(OAc)$_2$ (0.05 eq.) in THF (0.2M) was added portionwise $CH_2N_2$ until the reaction was completed. NMR of aliquots monitored the reaction. The resulting mixture was concentrated and flash chromatography (Hex:EtOAc; 3:2) to afford the two separate diastereoisomers. Each diastereoisomers were submitted to the procedures described in Step 2 and Step 3 to afford the (+) and (−) enantiomers of EXAMPLE 42

EXAMPLE 43

2-{3'-[6-(1-Methanesulfonyl-1-methyl-ethyl)quinolin-8-yl]-biphenyl-4-yl}-2-methyl-propionic acid

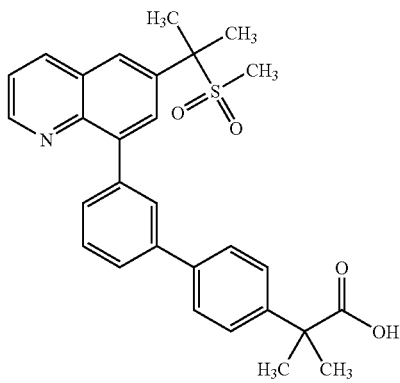

Step 1: 2-(4-Bromophenyl)-2-methyl-propionic acid methyl ester

To a solution of (4-Bromo-phenyl)-acetic acid methyl ester (1.0 eq) in DMF (0.2M) was added MeI (20 eq) followed by NaH (2.2 eq.) portion wise. The mixture was stirred for 2 h. An extra amount of NaH (1.1 eq) was added. The final mixture was stirred for 12 h, poured in saturated aqueous $NH_4Cl$ and extracted with $Et_2O$ (2×). The combined organic extracts were washed with water (3×), brine, dried over $MgSO_4$, filtered and concentrated. Flash chromatography (Hex:EtOAc; 95:5) afforded the title compound as a foam.

Step 2: 3-{3'-[6-(1-Methanesulfonyl-1-methylethyl)-quinolin-8-yl]-biphenyl-4-yl}-3-methyl-butyric acid methyl ester Prepared according to the procedure described in EXAMPLE 6, Step 2, but using 2-(4-bromo-phenyl)-2-methyl-propionic acid methyl ester from Step 1 as starting material. The reaction mixture was stirred 2 h at 70° C. Flash chromatography (Hex:EtOAc; 3:2) afforded the title compound as a foam.

Step 3: EXAMPLE 43

To a solution of 3-{3'-[6-(1-methanesulfonyl-1-methyl-ethyl)-quinolin-8-yl]-biphenyl-4-yl}-3-methyl-butyric acid methyl ester (1.0 eq.) from Step 1, in THF:MeOH (2:1; 0.2M) was added aqueous LiOH (2M; 5.0 eq.). The mixture was stirred for 4 h at 60° C., quenched with AcOH (20 eq.), poured in brine and extracted with EtOAc (2×). The combined organic extracts were dried over $Na_2SO_4$, filtered and concentrated. Crystallization in Hex:$Et_2O$:EtOAc afforded the title compound as a white solid. $^1H$ NMR (500 MHz, acetone-$d_6$): δ 8.93 (dd, 1H), 8.46 (dd, 1H), 8.29 (d, 1H), 8.21 (d, 1H), 8.02 (t, 1H), 7.72–7.68 (m, 4H), 7.59–7.51 (m, 4H), 2.72 (s, 3H), 2.00 (s, 6H), 1.59 (s, 6H).

EXAMPLE 44

1-{3'-[6-(1-Methanesulfonyl-1-methyl-ethyl)-quinolin-8-yl]-biphenyl-4-yl}-cyclopropanecarboxylic acid

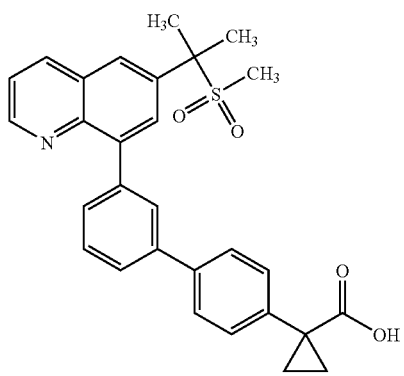

Step 1: 1-(4-Bromo-phenyl)-cyclopropanecarbonitrile
(See *Org Prep. and Proc.*, 1995, 27, 355.)

A mixture of (4-bromo-phenyl)-acetonitrile (1.0 eq.), 1-bromo-2-chloro-ethane (1.6 eq.), triethylbenzyl ammonium chloride (0.03 eq.) and aqueous NaOH 50% (6 eq.) was stirred for 12 h at 60° C. The resulting mixture was poured in water and extracted with Et$_2$O (2×). The combined organic extracts were washed with HCl 5%, brine, dried over MgSO$_4$, filtered and concentrated. Flash chromatography (Hex:EtOAc; 95:5) afforded the title compound as a foam.

Step 2: 1-(4-Bromo-phenyl)-cyclopropanecarboxylic acid methyl ester

To a solution of -(4-bromo-phenyl)-cyclopropanecarbonitrile from Step 1 in EtOH (0.2M) was added NaOH 25% (10 eq.). The mixture was stirred for 6 h at 100° C., quenched with AcOH (20 eq.), poured in brine, extracted with EtOAc (2×). The combined organic extracts were dried over MgSO$_4$, filtered and concentrated. The residue was dissolved in CH$_2$Cl$_2$ and diazomethane was added portionwise until the esterification was completed by TLC. Flash chromatography (Hex:EtOAc; 9:1) afforded the title compound as a colorless oil.

Step 3:1 {3'-[6-(1-Methanesulfonyl-1-methyl-ethyl)-quinolin-8-yl]-biphenyl-4-yl}-cyclopropanecarboxylic acid methyl ester Prepared according to the procedure described in EXAMPLE 6, Step 2, but 1-(4-bromo-phenyl)-cyclopropanecarboxylic acid methyl ester from Step 2 as starting material. The reaction mixture was stirred 2 h at 70° C. Flash chromatography (Hex:EtOAc; 2:1) afforded the title compound as a foam.

Step 4: EXAMPLE 44

Prepared according to the procedure described in EXAMPLE 43, Step 3, but using 1-{3'-[6-(1-methanesulfonyl-1-methyl-ethyl)-quinolin-8-yl]-biphenyl-4-yl}-cyclopropanecarboxylic acid methyl ester from Step 3 as starting material. Crystallization in Hex:Et$_2$O afforded the title compound as a white solid. $^1$H NMR (500 MHz, acetone-d$_6$): δ 8.96 (dd, 1H), 8.50 (dd, 1H), 8.32 (d, 1H), 8.24 (d, 1H), 8.04 (t, 1H), 7.75–7.72 (m, 2H), 7.69 (d, 2H), 7.62–7.58 (m, 2H), 7.51 (d, 2H), 2.75 (s, 3H), 2.03 (s, 6H), 1.59 (dd, 2H), 1.26 (dd, 2H).

EXAMPLE 45

3-13'-[6-(1-Methanesulfonyl-1-methyl-ethyl)-quinolin-8-yl]-biphenyl-4yl)-2,2-dimethyl-propionic acid

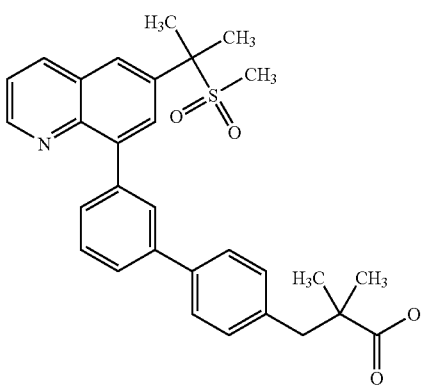

Step 1: 3-(4-Bromo-phenyl)-propionic acid tert-butyl ester

To a solution of cyclohexyl-isopropyl-amine (1.0 eq.) in THF (2.0M) at −78° C. was added dropwise n-BuLi (0.95eq.). The mixture was stirred at −78° C. for 20 min then a solution of acetic acid tert-butyl ester (1.0 eq.) in THF (5.0M) was added dropwise. The resulting mixture was stirred at −78° C. for 1 h. A solution of 4-bromobenzyl bromide (0.9eq.) in THF (5.0M) was then added dropwise and the final mixture was warm slowly to rt and stirred for 12 h. The reaction was quenched with cold aqueous HCl (1M), diluted water and extracted with Et$_2$O (2×). The combined organic extracts were washed with HCl (1M), brine, dried over Na$_2$SO$_4$, filtered and concentrated. The residue was distilled under vacuum (95° C., 0.4 mmHg) to afford the title compound as a colorless oil.

Step 2: 3-(4-Bromo-phenyl)-2,2-dimethyl-propionic acid tert-butyl ester

To a solution of cyclohexyl-isopropyl-amine (1.2eq.) in THF (1.0M) at −78° C. was added dropwise n-BuLi (1.2eq.). The mixture was stirred at −78° C. for 20 min then a solution of 3-(4-bromo-phenyl)-propionic acid tert-butyl ester from Step 1 (1.0 eq.) in THF (5.0M) was added dropwise. The resulting mixture was stirred at −78° C. for 30 min then MeI (5.0 eq.) was added. The final mixture was warm slowly to rt and stirred for 1 h. The reaction was poured in cold aqueous HCl (0.5M) and extracted with Et$_2$O (2×). The combined organic extracts were washed with brine, dried over MgSO$_4$, filtered and concentrated. The residue was resubmitted thrice to the above procedure until no monomethyl compound was observed by NMR. Flash chromatography (Hex:EtOAc; 95:5) afforded the title compound as a colorless oil.

Step 3: 3-{3'-[6-(1-Methanesulfonyl-1-methyl-ethyl)-quinolin-8-yl]-biphenyl-4-yl}-2,2-dimethyl-propionic acid tert-butyl ester Prepared according to the procedure described in EXAMPLE 6, step 2, but 3-(4-Bromo-phenyl)-2,2-dimethyl-propionic acid tert-butyl ester from Step 2 as starting material. The reaction mixture was stirred 2 h at 70° C. Flash chromatography (Hex:EtOAc 30 to 90% in 20 min) afforded the title compound as a foam.

Step 4: EXAMPLE 45

A solution of 3-{3'-[6-(1-methanesulfonyl-1-methyl-ethyl)-quinolin-8-yl]-biphenyl-4yl}-2,2-dimethyl-propionic acid tert-butyl ester from Step 3 in $CH_2Cl_2$:TFA (2:1) was stirred at rt for 12 h. The resulting mixture was concentrated and diluted with water. The pH was adjusted to 5 using first NaOH (1M) then excess AcOH. The aqueous phase was extracted with EtOAc (2×). The combined organic extracts were washed with brine, dried over $Na_2SO_4$, filtered and concentrated. Crystallization in Hex:$CH_2Cl_2$ afforded the title compound as a white solid. $^1$H NMR (500 MHz, acetone-$d_6$): δ 8.93 (dd, 1H), 8.46 (dd, 1H), 8.29 (d, 1H), 8.21 (d, 1H), 8.00 (t, 1H), 7.71–7.68 (m, 2H), 7.63 (d, 2H), 7.59–7.54 (m, 2H), 7.32 (d, 2H), 2.93 (s, 2H), 2.72 (s, 3), 2.00 (s, 6H), 1.19 (s, 6H).

EXAMPLE 46

2-{3'-[6-(1-Methanesulfonyl-1-methyl-ethyl)-quinolin-8-yl]-biphenyl-4-yl}-cyclopropanecarboxylic acid

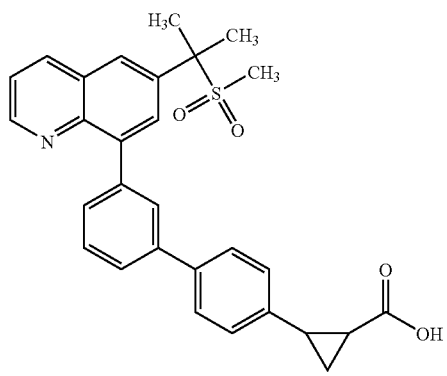

Step 1: Z-3-(4-Bromo-phenyl)-acrylic acid methyl ester (*Tett Lett.* 1983, 4405)

To a solution of [Bis-(2,2,2-trifluoro-ethoxy)-phosphoryl]-acetic acid methyl ester (1.0 eq.) and 18—C-6 (5.0 eq.) in THF (0.05M) at −78° C. was added dropwise KN(TMS)$_2$ (1.0 eq.). The mixture was stirred at −78° C. for 15 min then 4-bromobenzaldehyde (1.0 eq.) was added. The final mixture stirred for 1 h at −78° C., poured in saturated aqueous NH$_4$Cl and extracted with Et$_2$O (3×). The combined organic extracts were washed with, brine, dried over Na$_2$SO$_4$, filtered and concentrated. Flash chromatography (Hex:EtOAc 10 to 25%) afforded a mixture of desired material and the starting aldehyde. Upon treatment in CH$_2$Cl$_2$ of the mixture with Amino-Merrifield resin for 10 min, the aldehyde was removed. Filtration and concentration afforded the title compound as an oil.

Step 2: Cis-2-(4-Bromo-phenyl)-cyclopropanecarboxylic acid ethyl ester

Prepared according to the procedure described in Example 42, Step 1, but using Z-3-(4-Bromo-phenyl)-acrylic acid methyl ester from Step 1 as starting material Flash chromatography (Hex:EtOAc 85:15) afforded the title compound as a oil.

Step 3: C is 2-{3'-[6-(1-Methanesulfonyl-1-methyl-ethyl)-quinolin-8-yl]-biphenyl-4-yl}-cyclopropanecarboxylic acid methyl ester Prepared according to the procedure described in EXAMPLE 6, Step 2, but using 2-(4-bromo-phenyl)-cyclopropanecarboxylic acid ethyl ester from Step 2 and PdCl$_2$(dppf)$_2$ as starting materials. The reaction mixture was stirred 2 h at 60° C. Flash chromatography (Hex:EtOAc 35 to 50%) afforded the title compound as a foam.

Step 4: EXAMPLE 46

Prepared according to the procedure described in EXAMPLE 42, Step 3, but using C is 2-{3'-[6-(1-Methanesulfonyl-1-methyl-ethyl)-quinolin-8-yl]-biphenyl-4-yl}-cyclopropanecarboxylic acid methyl ester from Step 3 as starting materials. Crystallization in Et$_2$O afforded the title compound as a white solid. $^1$H NMR (500 MHz, acetone-$d_6$): δ 8.95 (dd, 1H), 8.49 (dd, 1H), 8.32 (d, 1H), 8.23 (d, 1H), 8.02 (t, 1H), 7.73–7.69 (m, 2H), 7.64–7.57 (m, 4H), 7.41 (d, 2H), 2.75 (s, 3H), 2.71–2.67 (m, 1H), 2.20–2.11 (m, 1H), 2.03 (s, 6H), 1.69–1.65 (m, 1H), 1.43–1.39 (m, 1H).

EXAMPLE 47

3-{3'-[6-(1-Methanesulfonyl-1-methyl-ethyl)-quinolin-8-yl]-biphenyl-4-yl}-3-methyl-butyric acid

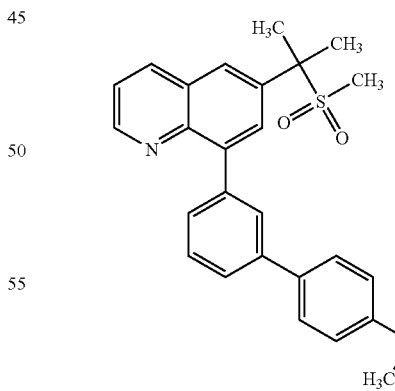

Step 1: 3-(4-Iodo-phenyl)-3-methyl-butyric acid methyl ester

The corresponding acid was prepared according to the procedure described in *J. Am. Chem. Soc.* 1948, 70, 370 and was converted to the title sing diazomethane in CH$_2$Cl$_2$.

Step 2: 3-{3'-[6-(1-Methanesulfonyl-1-methyl-ethyl)-quinolin-8-yl]-biphenyl-4-yl}-3-methyl-butyric acid methyl ester Prepared according to the procedure described in EXAMPLE 6, Step 2, but using 3-(4-Iodo-phenyl)-3-methyl-butyric acid methyl ester from Step 1 as starting material. The reaction mixture was stirred 2.5 h at 70° C. Flash chromatography (Hex:EtOAc 1:1) afforded the title compound as a foam.

Step 3: EXAMPLE 47

Prepared according to the procedure described in EXAMPLE 43, Step 3, but using 3-{3'[6-(1-methanesulfonyl-1-methyl-ethyl)-quinolin-8-yl]-biphenyl-4-yl}-3-methyl-butyric acid methyl ester from Step 2 as starting material. Crystallization in Hex:EtOAc afforded the title compound as a white solid. $^1$H NMR (500 MHz, acetone-$d_6$): δ 8.93 (dd, 1H), 8.46 (dd, 1H), 8.29 (d, 1H), 8.22 (d, 1H), 802 (t, 1H), 7.74–7.65 (m, 4H), 7.61–7.53 (m, 4H), 2.73 (s, 3H), 2.70 (s, 2H), 2.01 (s, 6H), 1.49 (s, 6H).

The following compounds were prepared according to the procedure described previously. Indicated is their respective $(M+1)^+$ value obtained from a low resolution mass spectrometer under electron-spray ionization conditions.

| EX. | Chemical name | ESI-LRMS $(M + 1)^+$ |
|---|---|---|
| 48 | 6-Isopropyl-8-(4'-methanesulfonyl-biphenyl-3-yl)-quinoline | 402.4 |
| 49 | 1-{3'-[6-(1-Methanesulfonyl-1-methyl-ethyl)-quinolin-8-yl]-biphenyl-3-yl}-ethanone | 444.3 |
| 50 | 1-{3-Hydroxy-3'-[6-(1-methanesulfonyl-1-methyl-ethyl)-quinolin-8-yl]-biphenyl-4-yl}-ethanone | 460.3 |
| 51 | 1-{4-Hydroxy-3'-[6-(1-methanesulfonyl-1-methyl-ethyl)-quinolin-8-yl]-biphenyl-3-yl}-ethanone | 460.3 |
| 52 | 8-(3'-Methanesulfonyl-biphenyl-3-yl)-6-(1-methanesulfonyl-1-methyl-ethyl)-quinoline | 480.2 |
| 53 | 8-(4'-Methanesulfonyl-biphenyl-3-yl)-6-(1-methanesulfonyl-1-methyl-ethyl)-quinoline | 480.2 |
| 54 | 6-(1-Methanesulfonyl-1-methyl-ethyl)-8-[3-(5-trifluoromethyl-pyridin-2-yl)-phenyl]-quinoline | 471.3 |
| 55 | 6-(1-Methanesulfonyl-1-methyl-ethyl)-8-[3-(3-methyl-pyridin-2-yl)-phenyl]-quinoline | 417.3 |
| 56 | 6-(1-Methanesulfonyl-1-methyl-ethyl)-8-(3-thiophen-2-yl-phenyl)-quinoline | 408.3 |
| 57 | 1-(5-{3-[6-(1-Methanesulfonyl-1-methyl-ethyl)-quinolin-8-yl]-phenyl}-thiophen-2-yl)-ethanone | 450.4 |
| 58 | 6-(1-Methanesulfonyl-1-methyl-ethyl)-8-[3-(3-methyl-thiophen-2-yl)-phenyl]-quinoline | 422.3 |
| 59 | 5-{3-[6-(1-Methanesulfonyl-1-methyl-ethyl)-quinolin-8-yl]-phenyl}-thiophene-2-sulfonic acid amide | 487.3 |
| 60 | 3'-[6-(1-Methanesulfonyl-1-methyl-ethyl)-quinolin-8-yl]-biphenyl-4-carbonitrile | 427.3 |
| 61 | 6-(1-Methanesulfonyl-1-methyl-ethyl)-8-(3-quinolin-3-yl-phenyl)-quinoline | 453.3 |
| 62 | 6-(1-Methanesulfonyl-1-methyl-ethyl)-8-(3-pyridin-3-yl-phenyl)-quinoline | 403.3 |
| 63 | 6-(1-Methanesulfonyl-1-methyl-ethyl)-8-(3-pyridin-4-yl-phenyl)-quinoline | 403.3 |
| 64 | 6-(1-Methanesulfonyl-1-methyl-ethyl)-8-(3'-nitro-biphenyl-3-yl)-quinoline | 447.2 |
| 65 | 8-(3-Benzo[1,3]dioxol-5-yl-phenyl)-6-(1-methanesulfonyl-1-methyl-ethyl)-quinoline | 446.3 |
| 66 | {4-Chloro-3'-[6-(1-methanesulfonyl-1-methyl-ethyl)-quinolin-8-yl]-biphenyl-3-yl}-methanol | 466.4 |
| 67 | 6-(1-Methanesulfonyl-1-methyl-ethyl)-8-[3-(5-methanesulfonyl-pyridin-3-yl)-phenyl]-quinoline | 481.3 |
| 68 | 6-(1-Methanesulfonyl-1-methyl-ethyl)-8-[3-(6-methylsulfanyl-pyridin-2-yl)-phenyl]-quinoline | 449.3 |
| 69 | 6-(1-Methanesulfonyl-1-methyl-ethyl)-8-[3-(6-methylsulfanyl-pyridin-3-yl)-phenyl]-quinoline | 449.3 |
| 70 | 3-{3'-[6-(1-Methanesulfonyl-1-methyl-ethyl)-quinolin-8-yl]-biphenyl-3-yl}-acrylic acid methyl ester | 486.3 |
| 71 | 3'-[6-(1-Methanesulfonyl-1-methyl-ethyl)-quinolin-8-yl]-biphenyl-3-carbaldehyde | — |
| 72 | 2,2,2-Trifluoro-1-{3'-[6-(1-methanesulfonyl-1-methyl-ethyl)-quinolin-8-yl]-biphenyl-3-yl}-ethanol | 500.3 |
| 73 | {3'-[6-(1-Methanesulfonyl-1-methyl-ethyl)-quinolin-8-yl]-biphenyl-2-yl}-methanol | 432.2 |
| 74 | 3-{3'-[6-(1-Methanesulfonyl-1-methyl-ethyl)-quinolin-8-yl]-biphenyl-2-yl}-acrylic acid methyl ester | 486.4 |
| 75 | 8-(2'-Methanesulfonylmethyl-biphenyl-3-yl)-6-(1-methanesulfonyl-1-methyl-ethyl)-quinoline | 494.3 |
| 76 | 6-(1-Methanesulfonyl-1-methyl-ethyl)-8-[2'-([1,3,4]thiadiazol-2-ylsulfanylmethyl)-biphenyl-3-yl]-quinoline | 532.3 |
| 77 | {3'-[6-(1-Methanesulfonyl-1-methyl-ethyl)-quinolin-8-yl]-biphenyl-4-yl}-methanol | 432.2 |
| 78 | 3-{3'-[6-(1-Methanesulfonyl-1-methyl-ethyl)-quinolin-8-yl]-biphenyl-4-yl}-acrylic acid methyl ester | — |
| 79 | 6-(1-Methanesulfonyl-1-methyl-ethyl)-8-[2'-(1-methyl-1H-imidazol-2-ylsulfanylmethyl)-biphenyl-3-yl]-quinoline | 528.3 |
| 80 | 3-{3'-[6-(1-Methanesulfonyl-1-methyl-ethyl)-quinolin-8-yl]-biphenyl-2-yl}-propionic acid methyl ester | 488.4 |
| 81 | 3-{3'-[6-(1-Methanesulfonyl-1-methyl-ethyl)-quinolin-8-yl]-biphenyl-2-yl}-prop-2-en-1-ol | 458.4 |
| 82 | 3-{3'-[6-(1-Methanesulfonyl-1-methyl-ethyl)-quinolin-8-yl]-biphenyl-2-yl}-propan-1-ol | 460.3 |
| 83 | {3'-[6-(1-Methanesulfonyl-1-methyl-ethyl)-quinolin-8-yl]-biphenyl-3-yl}-methanol | 432.2 |
| 84 | 2-(6-{3-[6-(1-Methanesulfonyl-1-methyl-ethyl)-quinolin-8-yl]-phenyl}-pyridin-3-yl)-propan-2-ol | 461.5 |
| 85 | 3-{3'-[6-(1-Methanesulfonyl-1-methyl-ethyl)-quinolin-8-yl]-biphenyl-2-yl}-propionic acid | 474.4 |
| 86 | 6-(1-Methanesulfonyl-1-methyl-ethyl)-8-[3-(6-methyl-pyridin-3-yl)-phenyl]-quinoline | 337.1 |
| 87 | 3-{3'-[6-(1-Methanesulfonyl-1-methyl-ethyl)-quinolin-8-yl]-biphenyl-3-yl}-acrylic acid | 472.4 |
| 88 | 5-{3-[6-(1-Methanesulfonyl-1-methyl-ethyl)-quinolin-8-yl]-phenyl}-nicotinic acid ethyl ester | 475.3 |
| 89 | 6-(1-Methanesulfonyl-1-methyl-ethyl)-8-{3-[6-(propane-2-sulfonyl)-pyridin-3-yl]-phenyl}-quinoline | 509.4 |
| 90 | 8-[3-(6-Benzyloxy-pyridin-3-yl)-phenyl]-6-(1-methanesulfonyl-1-methyl-ethyl)-quinoline | 509.3 |
| 91 | 2-(5-{3-[6-(1-Methanesulfonyl-1-methyl-ethyl)-quinolin-8-yl]-phenyl}-pyridin-3-yl)-propan-2-ol | 461.3 |
| 92 | 3-{3'-[6-(1-Methanesulfonyl-1-methyl-ethyl)-quinolin-8-yl]-biphenyl-3-yl}-propionic acid | 474.4 |
| 93 | 6-(1-Methanesulfonyl-1-methyl-ethyl)-8-{3-[5-(2-trimethylsilanyl-ethylsulfanyl)-pyridin-3-yl]-phenyl}-quinoline | 535.4 |
| 94 | 8-{3-[5-(4-Fluoro-benzylsulfanyl)-pyridin-3-yl]-phenyl}-6-(1-methanesulfonyl-1-methyl-ethyl)-quinoline | 543.2 |
| 95 | 3-{3'-[6-(1-Methanesulfonyl-1-methyl-ethyl)-quinolin-8-yl]-biphenyl-4-yl}-acrylic acid | 472.4 |
| 96 | N-Cyclopropyl-5-{3-[6-(1-methanesulfonyl-1-methyl-ethyl)-quinolin-8-yl]-phenyl}-nicotinamide | 486.2 |
| 97 | 3-{3-[6-(1-Methanesulfonyl-1-methyl-ethyl)-quinolin-8-yl]-phenyl}-5-trifluoromethyl-pyridin-2-ylamine | 486.3 |
| 98 | Dicyclopropyl-(5-{3-[6-(1-methanesulfonyl-1-methyl-ethyl)-quinolin-8-yl]-phenyl}-1-oxy-pyridin-2-yl)-methanol | 529.5 |
| 99 | 8-[3-(6-Ethanesulfonyl-pyridin-3-yl)-phenyl]-6-(1-methanesulfonyl-1-methyl-ethyl)-quinoline | 495.3 |
| 100 | 2-(5-{3-[6-(1-Methanesulfonyl-1-methyl-ethyl)-quinolin-8-yl]-phenyl}-pyridin-2-yl)-propan-2-ol | 461.5 |
| 101 | 6-(1-Methanesulfonyl-1-methyl-ethyl)-8-{3-[1-oxy-5-(2-trimethylsilanyl-ethanesulfonyl)-pyridin-3-yl]-phenyl}-quinoline | 583.4 |

| EX. | Chemical name | ESI-LRMS (M + 1)+ |
|---|---|---|
| 102 | 8-(3-{5-[1,2-Bis-(4-fluoro-phenyl)-ethanesulfonyl]-1-oxy-pyridin-3-yl}-phenyl)-6-(1-methanesulfonyl-1-methyl-ethyl)-quinoline | 699.3 |
| 103 | 8-[3-(5-Ethanesulfinyl-1-oxy-pyridin-3-yl)-phenyl]-6-(1-methanesulfonyl-1-methyl-ethyl)-quinoline | 495.1 |
| 104 | 6-(1-Methanesulfonyl-1-methyl-ethyl)-8-[3-(1-oxy-5-trifluoromethyl-pyridin-3-yl)-phenyl]-quinoline | 487.3 |
| 105 | 6-(1-Methanesulfonyl-1-methyl-ethyl)-8-[3-(6-methanesulfonyl-5-methyl-pyridin-3-yl)-phenyl]-quinoline | 495.9 |
| 106 | 3-(5-{3-[6-(1-Methanesulfonyl-1-methyl-ethyl)-quinolin-8-yl]-phenyl}-1-oxy-pyridin-2-yl)-pentan-3-ol | 506.5 |
| 107 | (5-{3-[6-(1-Methanesulfonyl-1-methyl-ethyl)-quinolin-8-yl]-phenyl}-1-oxy-pyridin-3-yl)-methanol | 449.3 |
| 108 | Difluoro-(5-{3-[6-(1-methanesulfonyl-1-methyl-ethyl)-quinolin-8-yl]-phenyl}-pyridin-3-ylsulfanyl)-acetic acid ethyl ester | 557.2 |
| 109 | Difluoro-(5-{3-[6-(1-methanesulfonyl-1-methyl-ethyl)-quinolin-8-yl]-phenyl}-pyridin-3-ylsulfanyl)-acetic acid | 529.4 |
| 110 | (5-{3-[6-(1-Methanesulfonyl-1-methyl-ethyl)-quinolin-8-yl]-phenyl}-1-oxy-pyridin-2-yl)-methanol | 449.3 |
| 111 | 6-(1-Methanesulfonyl-1-methyl-ethyl)-8-(5-phenyl-pyridin-3-yl)-quinoline | 404.3 |
| 112 | 6-(1-Methanesulfonyl-1-methyl-ethyl)-8-(1-oxy-5-phenyl-pyridin-3-yl)-quinoline | 420.0 |
| 113 | 1-Isopropyl-3-(5-{3-[6-(1-methanesulfonyl-1-methyl-ethyl)-quinolin-8-yl]-phenyl}-pyridin-2-yl)-urea | 502.6 |
| 114 | 6-(1-Methanesulfonyl-1-methyl-ethyl)-8-{3-[5-(2-trimethylsilanyl-ethanesulfonyl)-pyridin-3-yl]-phenyl}-quinoline | 567.4 |
| 115 | 8-[3-(4-Chloro-pyridin-3-yl)-phenyl]-6-(1-methanesulfonyl-1-methyl-ethyl)-quinoline | 437.3 |
| 116 | (5-{3-[6-(1-Methanesulfonyl-1-methyl-ethyl)-quinolin-8-yl]-phenyl}-pyridin-2-yl)-(4-methylsulfanyl-phenyl)-methanone | 553.5 |
| 117 | 5-{3-[6-(1-Methanesulfonyl-1-methyl-ethyl)-quinolin-8-yl]-phenyl}-1-oxy-pyridine-2-carboxylic acid isopropylamide | 504.4 |
| 118 | 3'-[6-(1-Methanesulfonyl-1-methyl-ethyl)-quinolin-8-yl]-biphenyl-2-carbonitrile | 427.3 |
| 119 | 6-(1-Methanesulfonyl-1-methyl-ethyl)-8-(2'-methylsulfanyl-biphenyl-3-yl)-quinoline | 448.2 |
| 120 | 8-(2'-Methanesulfonyl-biphenyl-3-yl)-6-(1-methanesulfonyl-1-methyl-ethyl)-quinoline | 480.2 |
| 121 | 1,1,1,3,3,3-Hexafluoro-2-(5-{3-[6-(1-methanesulfonyl-1-methyl-ethyl)-quinolin-8-yl]-phenyl}-pyridin-3-yl)-propan-2-ol | 569.7 |
| 122 | 6-(1-Methanesulfonyl-1-methyl-ethyl)-8-{3-[6-(4-methoxy-benzyloxy)-pyridin-2-yl]-phenyl}-quinoline | 539.4 |
| 123 | 6-{3-[6-(1-Methanesulfonyl-1-methyl-ethyl)-quinolin-8-yl]-phenyl}-1H-pyridin-2-one | 419.3 |
| 124 | 1,1,1,3,3,3-Hexafluoro-2-(5-{3-[6-(1-methanesulfonyl-1-methyl-ethyl)-quinolin-8-yl]-phenyl}-1-oxy-pyridin-3-yl)-propan-2-ol | 585.5 |
| 125 | 5-{3-[6-(1-Methanesulfonyl-1-methyl-ethyl)-quinolin-8-yl]-phenyl}-nicotinic acid | 447.2 |
| 126 | 1,1,1,3,3,3-Hexafluoro-2-(5-{3-[6-(1-methanesulfonyl-1-methyl-ethyl)-quinolin-8-yl]-phenyl}-1-oxy-pyridin-2-yl)-propan-2-ol | 585.5 |
| 127 | 5-{3-[6-(1-Methanesulfonyl-1-methyl-ethyl)-quinolin-8-yl]-phenyl}-1-oxy-pyridine-2-carboxylic acid methyl ester | 477.2 |
| 128 | 5-{3-[6-(1-Methanesulfonyl-1-methyl-ethyl)-quinolin-8-yl]-phenyl}-1-oxy-pyridine-2-carboxylic acid | 463.2 |
| 129 | {3'-[6-(1-Methanesulfonyl-1-methyl-ethyl)-quinolin-8-yl]-biphenyl-3-yl}-acetic acid | 460.3 |
| 130 | 3'-[6-(1-Methanesulfonyl-1-methyl-ethyl)-quinolin-8-yl]-biphenyl-3-carboxylic acid | 446.3 |
| 131 | 5-{3-[6-(1-Methanesulfonyl-1-methyl-ethyl)-quinolin-8-yl]-phenyl}-1-oxy-nicotinic acid | 463.2 |
| 132 | 3-{3'-[6-(1-Methanesulfonyl-1-methyl-ethyl)-quinolin-8-yl]-biphenyl-4-yl}-propionic acid methyl ester | 488.4 |
| 133 | 3-{3'-[6-(1-Methanesulfonyl-1-methyl-ethyl)-quinolin-8-yl]-biphenyl-4-yl}-propionic acid | 474.4 |
| 134 | 2-{3'-[6-(1-Methanesulfonyl-1-methyl-ethyl)-quinolin-8-yl]-biphenyl-4-yl}-cyclopropanecarboxylic acid methyl ester | 514.4 |
| 135 | 5-{3-[6-(1-Methanesulfonyl-1-methyl-ethyl)-quinolin-8-yl]-phenyl}-1-oxy-nicotinonitrile | 444.3 |
| 136 | 3'-[6-(1-Methanesulfonyl-1-methyl-ethyl)-quinolin-8-yl]-biphenyl-3-carboxylic acid amide | 445.2 |
| 137 | 2-{3'-[6-(1-Methanesulfonyl-1-methyl-ethyl)-quinolin-8-yl]-biphenyl-3-yl}-cyclopropanecarboxylic acid | 486.4 |
| 138 | 5-{3-[6-(1-Methanesulfonyl-1-methyl-ethyl)-quinolin-8-yl]-phenyl}-1-oxy-nicotinic acid 2,2-dimethyl-propionyloxymethyl ester | 577.4 |
| 139 | 3-{3'-[6-(1-Methanesulfonyl-1-methyl-ethyl)-quinolin-8-yl]-biphenyl-4-yl}-2-methyl-propionic acid tert-butyl ester | 544.4 |
| 140 | 3-{3'-[6-(1-Methanesulfonyl-1-methyl-ethyl)-quinolin-8-yl]-biphenyl-4-yl}-2-methyl-propionic acid | 488.4 |
| 141 | 2-{3'-[6-(1-Methanesulfonyl-1-methyl-ethyl)-quinolin-8-yl]-biphenyl-4-yl}-2-methyl-propionic acid methyl ester | 502.2 |
| 142 | {3'-[6-(1-Methanesulfonyl-1-methyl-ethyl)-quinolin-8-yl]-biphenyl-4-yl}-acetic acid | 460.3 |
| 143 | 1-{3'-[6-(1-Methanesulfonyl-1-methyl-ethyl)-quinolin-8-yl]-biphenyl-4-yl}-cyclopropanecarboxylic acid amide | 485.3 |
| 144 | 2-{3'-[6-(1-Methanesulfonyl-1-methyl-ethyl)-quinolin-8-yl]-biphenyl-3-yl}-2-methyl-propionic acid | 488.4 |
| 145 | 8-[3-(5-Chloro-1-oxy-pyridin-3-yl)-phenyl]-6-(1-methanesulfonyl-1-methyl-ethyl)-quinoline | 453.3 |
| 146 | (1-{3'-[6-(1-Methanesulfonyl-1-methyl-ethyl)-quinolin-8-yl]-biphenyl-4-ylmethylsulfanylmethyl}-cyclopropyl)-acetic acid | 560.3 |
| 147 | (1-{3'-[6-(1-Methanesulfonyl-1-methyl-ethyl)-quinolin-8-yl]-biphenyl-4-ylmethanesulfonyl-methyl}-cyclopropyl)-acetic acid | 592.3 |
| 148 | 3-{3'-[6-(1-Methanesulfonyl-1-methyl-ethyl)-quinolin-8-yl]-biphenyl-4-yl}-acrylic acid methyl ester | 486.4 |
| 149 | 1-{3'-[6-(1-Methanesulfonyl-1-methyl-ethyl)-quinolin-8-yl]-biphenyl-4-ylmethyl}-cyclobutanecarboxylic acid | 514.4 |
| 150 | [1-(5-{3-[6-(1-Methanesulfonyl-1-methyl-ethyl)-quinolin-8-yl]-phenyl}-pyridin-2-ylsulfanylmethyl)-cyclopropyl]-acetic acid | 547.4 |
| 151 | [1-(5-{3-[6-(1-Methanesulfonyl-1-methyl-ethyl)-quinolin-8-yl]-phenyl}-pyridine-2-sulfonylmethyl)-cyclopropyl]-acetic acid | 579.4 |
| 152 | 6-(1-Methanesulfonyl-1-methyl-ethyl)-8-{4'-[2-(1H-tetrazol-5-yl)-cyclopropyl]-biphenyl-3-yl}-quinoline | 510.3 |
| 153 | (1-{3'-[6-(1-Methanesulfonyl-1-methyl-ethyl)-quinolin-8-yl]-biphenyl-4-ylsulfanylmethyl}-cyclopropyl)-acetic acid | 546.2 |
| 154 | (1-{3'-[6-(1-Methanesulfonyl-1-methyl-ethyl)-quinolin-8-yl]-biphenyl-4-sulfonylmethyl}-cyclopropyl)-acetic acid | 578.4 |
| 155 | 3-{3'-[6-(1-Methanesulfonyl-1-methyl-ethyl)-quinolin-8-yl]-biphenyl-4-yl}-acrylic acid | 472.4 |

Other variations or modifications, which will be obvious to those skilled in the art, are within the scope and teachings of this invention. This invention is not to be limited except as set forth in the following claims.

What is claimed is:

1. A compound represented by Formula (I):

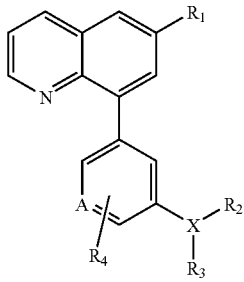

or a pharmaceutically acceptable salt thereof, wherein
A is C or N;
X is phenyl, pyridyl, pyrazinyl, thiaphenyl, quinolinyl, benzofuranyl, oxadiazolyl, diazolylpyridinyl, imidazolylpyridinyl, oxadiazolylphenyl, or benzodioxolyl;
$R_1$ is hydrogen, halogen; or —$C_{1-6}$alkyl, -cyclo$C_{3-6}$alkyl, or —$C_{1-6}$alkenyl group, wherein any of the groups is optionally substituted with 1–6 substituents; wherein each substituent is independently halogen, —OH, —CN, or —$SO_2$—$C_{1-6}$alkyl;
$R_2$, and $R_3$ are each independently hydrogen, halogen, hydroxyl, —CN, —$NO_2$; or —$C_{1-6}$alkyl, —$C_{2-6}$alkenyl, —$C_{1-6}$alkyl($C_{2-6}$alkenyl)$_2$, —$C_{0-4}$alkyl($C_{3-6}$cycloalkyl)$_2$, —$C_{0-6}$alkyl-N($C_{0-6}$alkyl)$_2$, —$C_{0-4}$alkyl-O—$C_{1-6}$alkyl, —$C_{1-6}$alkyl-phenyl, —$C_{0-6}$alkyl-$SO_2$—$C_{1-6}$alkyl, —$C_{0-6}$alkyl-C(O)—$C_{0-4}$alkyl, —$C_{0-6}$alkyl-C(O)—$C_{0-6}$alkyl-phenyl, —$C_{0-6}$alkyl-C(O)—$C_{0-4}$alkyl-O—$C_{0-6}$alkyl, —$C_{0-6}$alkyl-C(O)—$C_{0-6}$alkyl-O—$C_{0-6}$alkyl-O—$C_{0-6}$alkyl-C(O)—$C_{0-6}$alkyl, —$C_{2-6}$alkenyl-C(O)—$C_{0-4}$alkyl-O—$C_{0-6}$alkyl, $C_{0-4}$alkyl-$C_{3-6}$cycloalkyl-$C_{0-6}$alkyl-C(O)—$C_{0-6}$alkyl, —$C_{0-4}$alkyl-$C_{3-6}$cycloalkyl-$C_{0-6}$alkyl-C(O)—$C_{0-6}$alkyl-N($C_{0-6}$alkyl)$_2$, —$C_{0-4}$alkyl-$C_{3-6}$cycloalkyl-$C_{0-6}$alkyl-C(O)—$C_{0-4}$alkyl-O—$C_{0-6}$alkyl, —$C_{2-6}$alkenyl-C(O)—$C_{0-4}$alkyl-N($C_{0-6}$alkyl)-pyridyl, —$C_{0-6}$alkyl-C(O)—$C_{0-4}$alkyl-N($C_{0-4}$alkyl)$_2$, —$C_{0-6}$alkyl-C(O)—$C_{0-4}$alkyl-N($C_{0-4}$alkyl)-$C_{3-6}$cycloalkyl, —$C_{2-6}$alkenyl-C(O)—$C_{0-4}$alkyl-N($C_{0-4}$alkyl)-$C_{3-6}$cycloalkyl, —$SO_2$—$C_{0-6}$alkyl-phenyl, —$SO_2$—$C_{0-6}$alkyl-(—$C_{0-6}$alkyl-phenyl)(—$C_{0-6}$alkyl-phenyl), —$C_{0-4}$alkyl-$SO_2$—$C_{0-4}$alkyl-$C_{3-6}$cycloalkyl-$C_{0-4}$alkyl-C(O)—$C_{0-4}$alkyl-O—$C_{0-4}$alkyl, —S(O)—$C_{0-6}$alkyl, —P(O)(O)—$C_{0-4}$alkyl)(O)—$C_{0-4}$alkyl), —$C_{2-6}$alkenyl-C(O)—$C_{0-4}$alkyl-N($C_{0-4}$alkyl)pyridyl, —S—$C_{1-6}$alkyl, —$C_{0-6}$alkyl-N($C_{0-6}$alkyl)-C(O)—$C_{0-6}$alkyl, —$C_{0-6}$alkyl-N($C_{0-6}$alkyl)-C(O)—N($C_{0-6}$alkyl)$_2$, —$C_{0-4}$alkyl-S—$C_{1-4}$alkyl-oxadiazolyl($C_{0-4}$alkyl), —$C_{0-4}$alkyl-C(O)—$C_{0-4}$alkyl-phenyl, —$C_{0-4}$alkyl-O—$C_{0-4}$alkyl-phenyl, —$C_{0-4}$alkyl-$C_{3-6}$cycloalkyl-$C_{0-4}$alkyl-tetrazolyl, —$SO_2$—N($C_{0-4}$alkyl)$_2$, —$C_{0-4}$alkyl-S—$C_{0-4}$alkyl-thiadiazolyl($C_{0-4}$alkyl), —$C_{0-4}$alkyl-S—$C_{0-4}$alkyl-diazolyl($C_{0-4}$alkyl), —$C_{0-4}$alkyl-S—$C_{1-4}$alkyl-Si($C_{0-4}$alkyl)$_3$, —$C_{0-4}$alkyl-S—$C_{0-4}$alkyl-phenyl($C_{0-4}$alkyl), —$C_{0-4}$alkyl-S—$C_{0-4}$alkyl-C(O)—$C_{0-4}$alkyl-O—$C_{0-4}$alkyl, or —$C_{0-4}$alkyl-S—$C_{0-4}$alkyl-$C_{3-6}$cycloalkyl-$C_{0-4}$alkyl-C(O)—$C_{0-4}$alkyl-O—$C_{0-4}$alkyl, wherein any alkyl, cycloalkyl, alkenyl, phenyl, or pyridyl are each optionally substituted with 1–9 independently halogen, hydroxyl, —$C_{0-4}$alkyl-O—$C_{1-4}$alkyl, or —$C_{0-4}$alkyl-S—$C_{1-6}$alkyl;

optionally, $R_2$ forms =O with an adjoining bond;
$R_4$ is hydrogen, or halogen; and
any ring nitrogen optionally forms N-oxide or N-chloride.

2. The compound according to claim 1, wherein A is C.
3. The compound according to claim 2, wherein X is phenyl.
4. The compound according to claim 2, wherein X is thiaphenyl.
5. The compound according to claim 2, wherein X is benzofuranyl.
6. The compound according to claim 2, wherein X is pyridyl.
7. The compound according to claim 2, wherein X is pyridyl.
8. The compound according to claim 2, wherein X is quinolinyl.
9. The compound according to claim 2, wherein X is oxadiazolyl.
10. The compound according to claim 2, wherein X is diazolylpyridinyl or imidazolylpyridinyl.
11. The compound according to claim 2, wherein X is pyrazinyl.
12. The compound according to claim 2, wherein X is oxadiazolylphenyl.
13. The compound according to claim 2, wherein X is benzodioxolyl.
14. The compound according to claim 1, wherein A is N.
15. The compound according to claim 14, wherein X is phenyl.
16. The compound according to claim 1, represented by

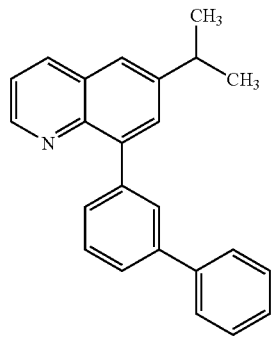

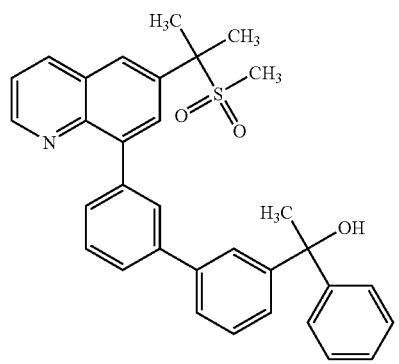

-continued
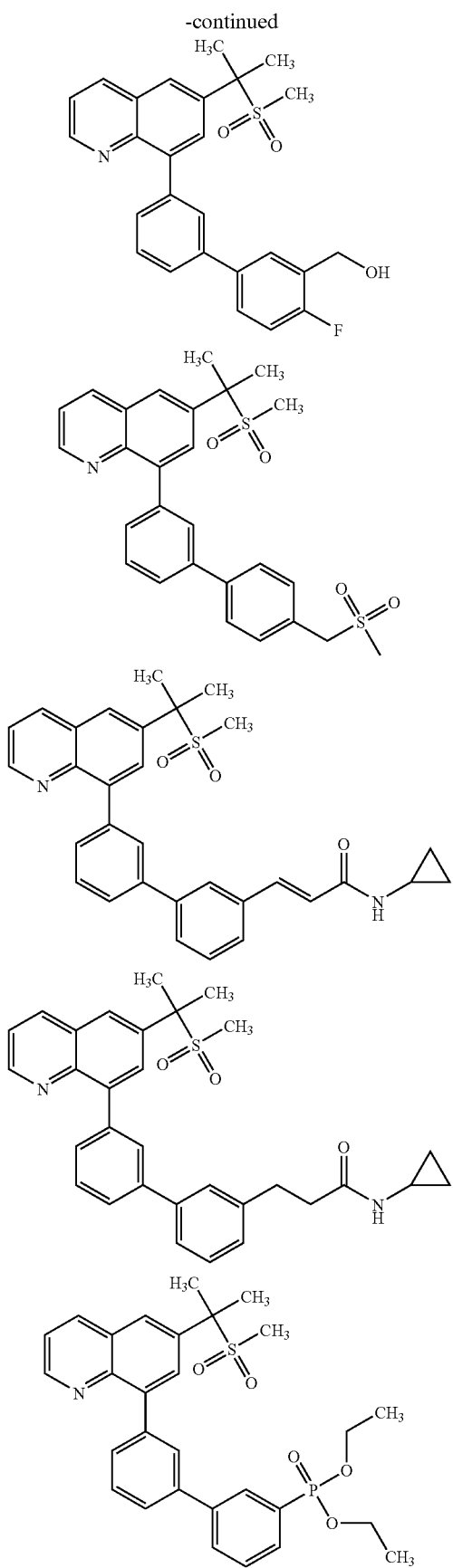
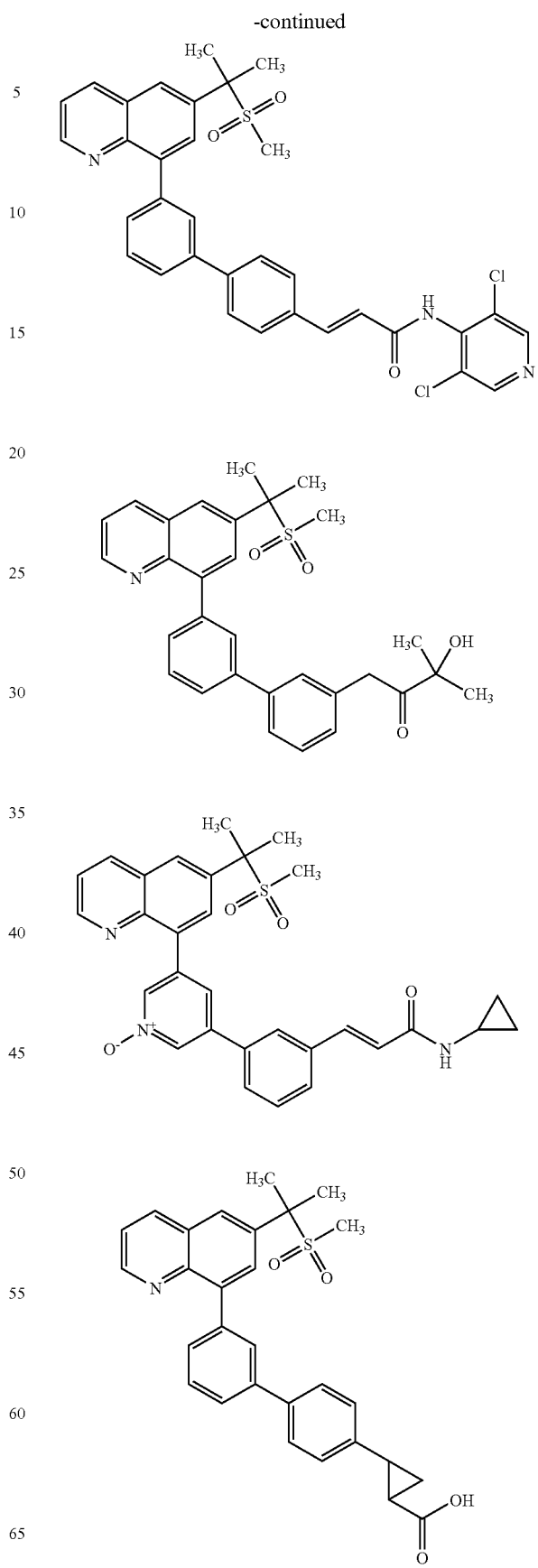

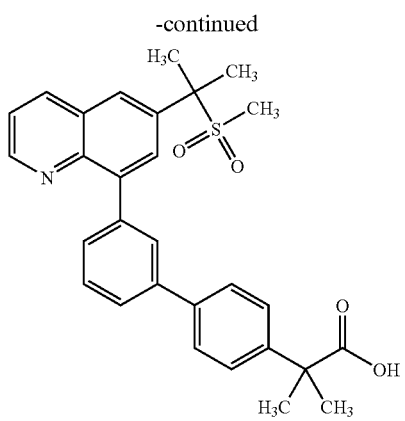
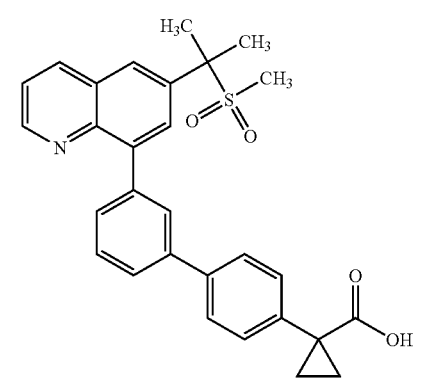
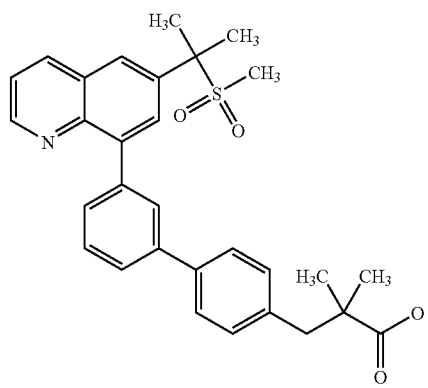
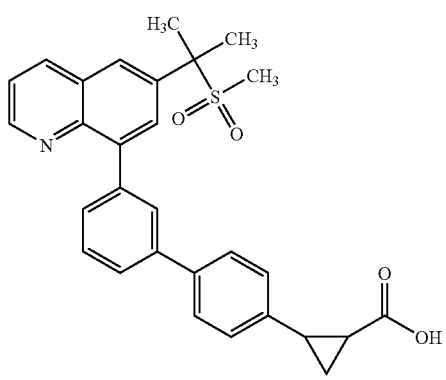
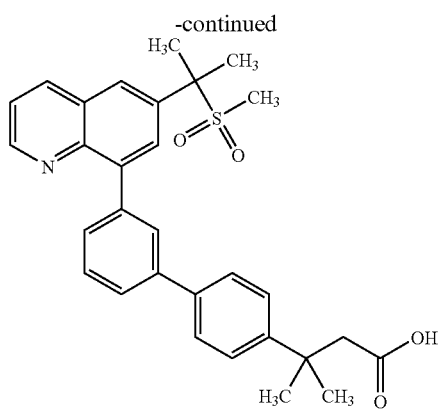
or a pharmaceutically acceptable salt thereof.
17. The compound according to claim 1, represented by
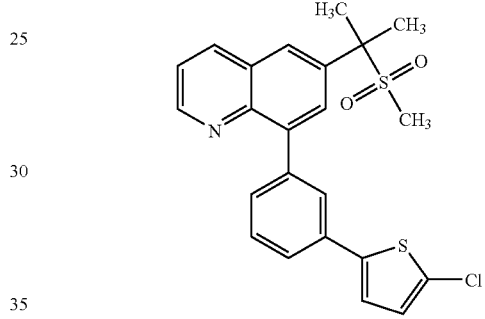
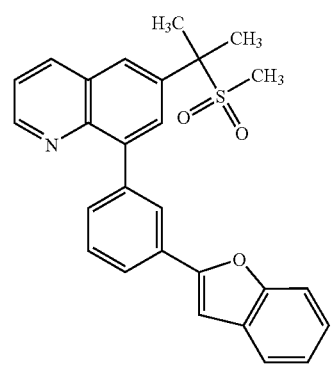
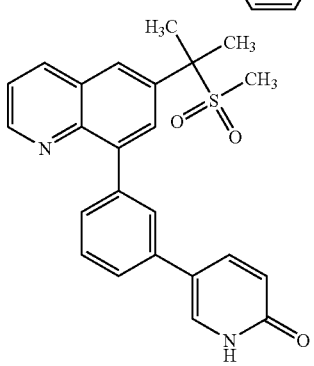

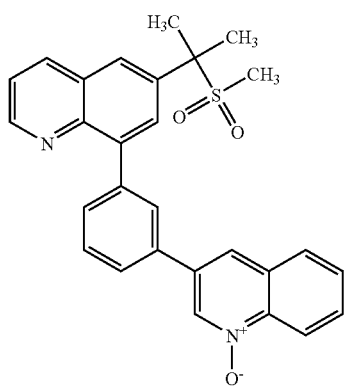
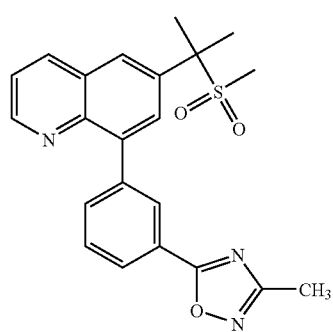
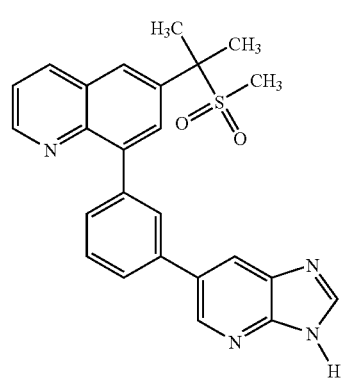
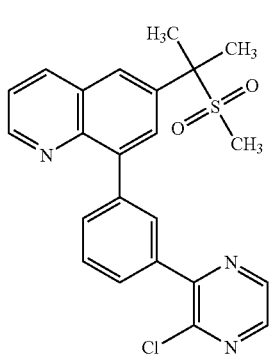
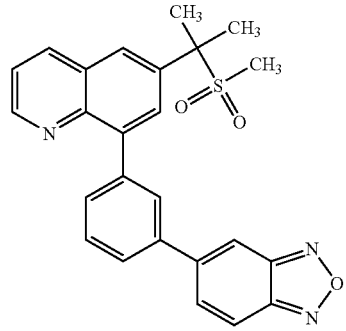
or a pharmaceutically acceptable salt thereof.
18. The compound according to claim 1, represented by
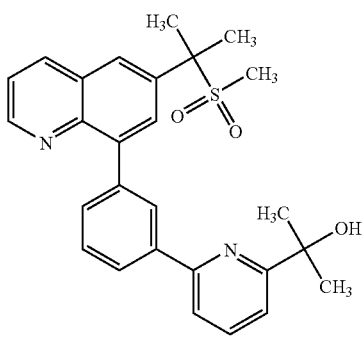
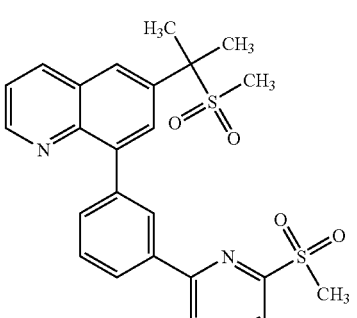
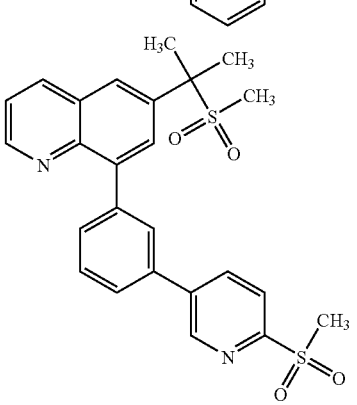

89
-continued
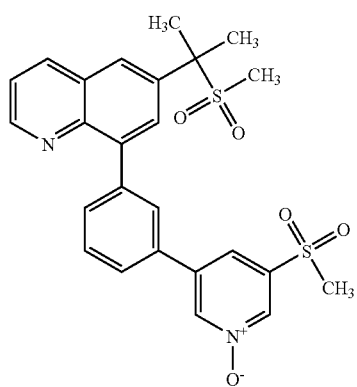
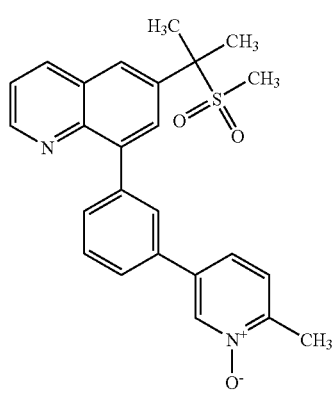
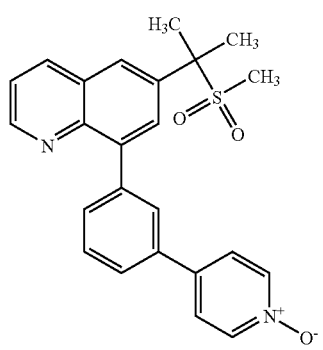
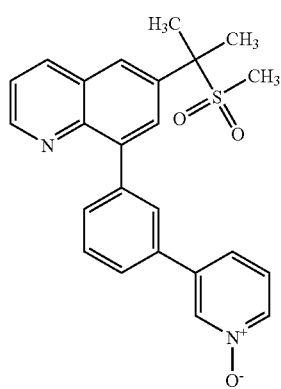
90
-continued
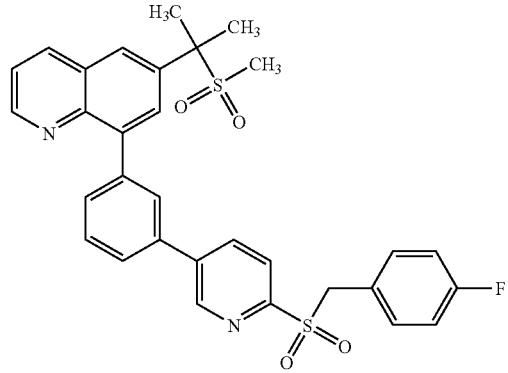
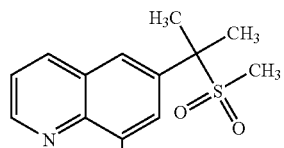
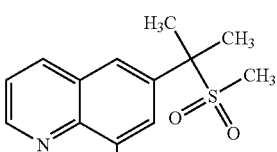
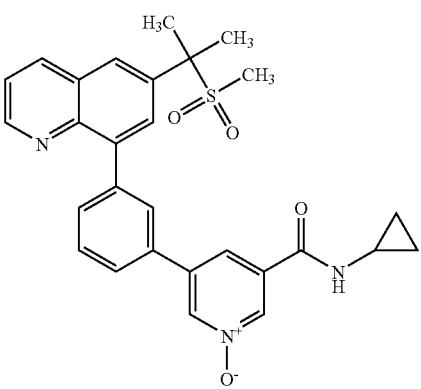

91
-continued
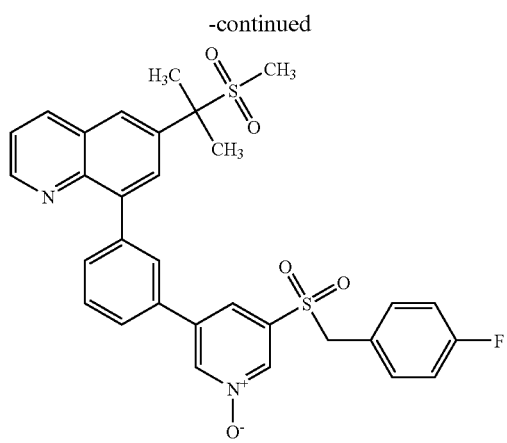
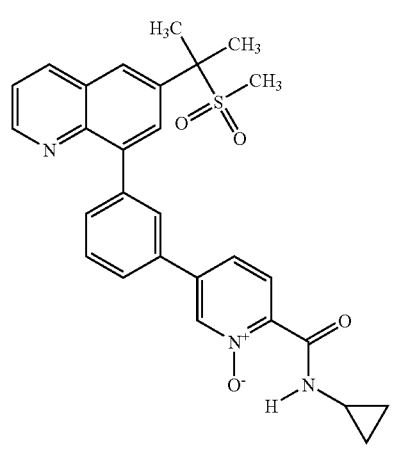
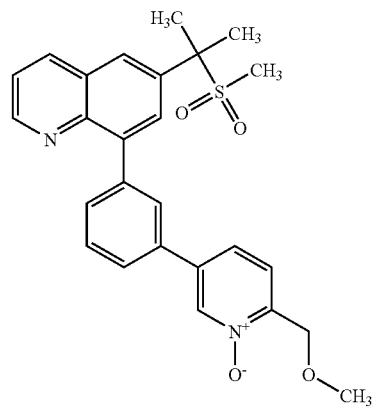
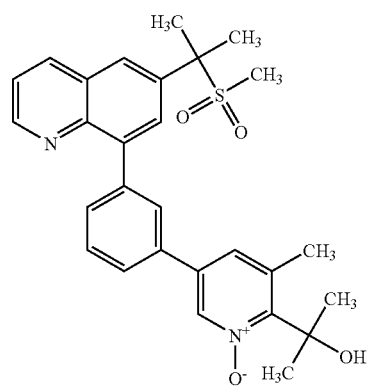
92
-continued
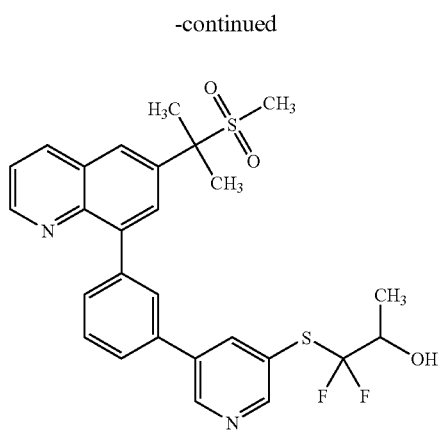
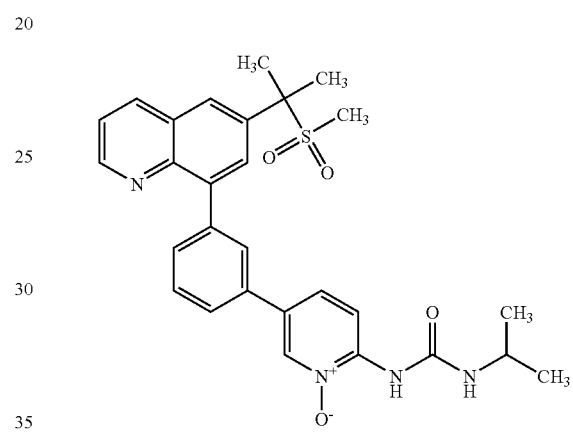
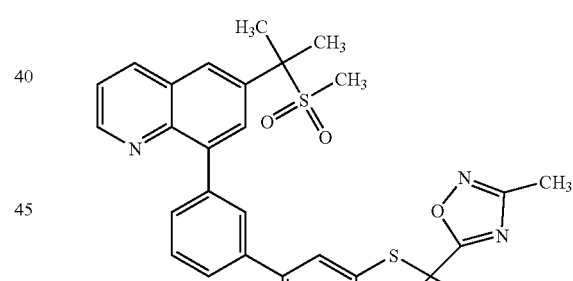
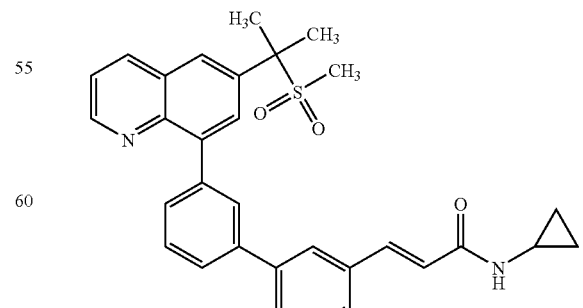

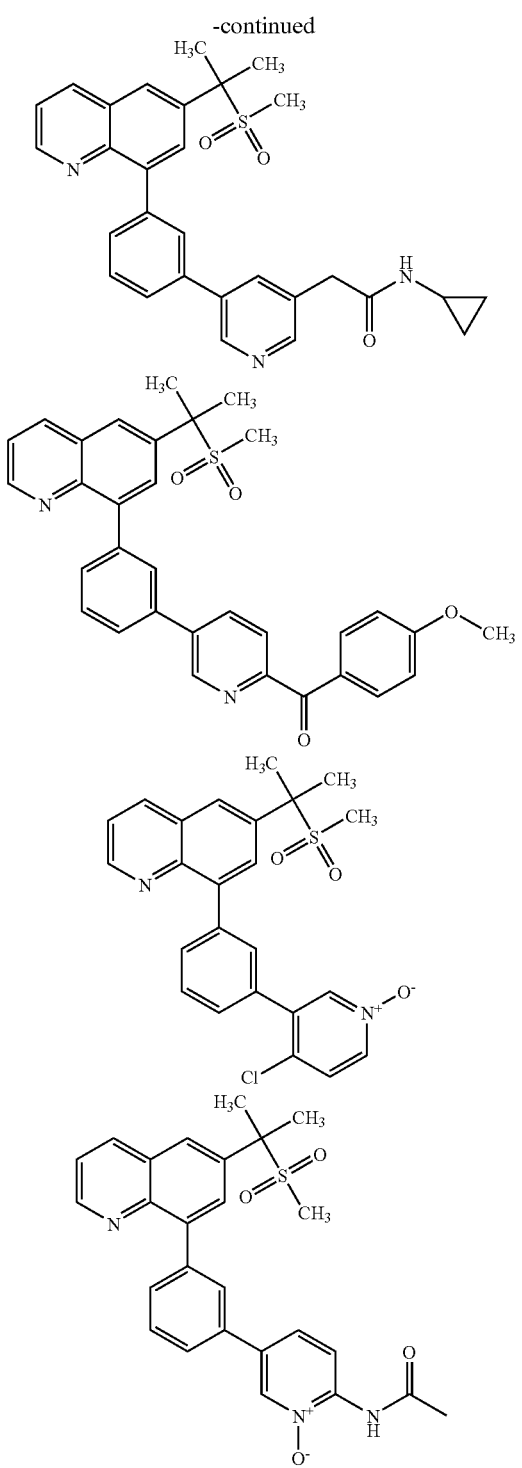

or a pharmaceutically acceptable salt thereof.

19. The compound according to claim 1, consisting of
6-isopropyl-8-(4'-methanesulfonyl-biphenyl-3-yl)-quinoline;
1-{3'-[6-(1-methanesulfonyl-1-methyl-ethyl)-quinolin-8-yl]-biphenyl-3-yl}-ethanone;
1-{3-hydroxy-3'-[6-(1-methanesulfonyl-1-methyl-ethyl)-quinolin-8-yl]-biphenyl-4-yl}-ethanone;
1-{4-hydroxy-3'-[6-(1-methanesulfonyl-1-methyl-ethyl)-quinolin-8-yl]-biphenyl-3-yl}-ethanone;
8-(3'-methanesulfonyl-biphenyl-3-yl)-6-(1-methanesulfonyl-1-methyl-ethyl)-quinoline;
8-(4'-methanesulfonyl-biphenyl-3-yl)-6-(1-methanesulfonyl-1-methyl-ethyl)-quinoline;
3'-[6-(1-methanesulfonyl-1-methyl-ethyl)-quinolin-8-yl]-biphenyl-4-carbonitrile;
6-(1-methanesulfonyl-1-methyl-ethyl)-8-(3'-nitro-biphenyl-3-yl)-quinoline;
{4-chloro-3'-[6-(1-methanesulfonyl-1-methyl-ethyl)-quinolin-8-yl]-biphenyl-3-yl}-methanol;
3-{3'-[6-(1-methanesulfonyl-1-methyl-ethyl)-quinolin-8-yl]-biphenyl-3-yl}-acrylic acid methyl ester;
3'-[6-(1-methanesulfonyl-1-methyl-ethyl)-quinolin-8-yl]-biphenyl-3-carbaldehyde;
2,2,2-trifluoro-1-{3'-[6-(1-methanesulfonyl-1-methyl-ethyl)-quinolin-8-yl]-biphenyl-3-yl}-ethanol;
{3'-[6-(1-methanesulfonyl-1-methyl-ethyl)-quinolin-8-yl]-biphenyl-2-yl}-methanol;
3-{3'-[6-(1-methanesulfonyl-1-methyl-ethyl)-quinolin-8-yl]-biphenyl-2-yl}-acrylic acid methyl ester;
8-(2'-methanesulfonylmethyl-biphenyl-3-yl)-6-(1-methanesulfonyl-1-methyl-ethyl)-quinoline;
6-(1-methanesulfonyl-1-methyl-ethyl)-8-[2'-([1,3,4]thiadiazol-2-ylsulfanylmethyl)-biphenyl-3-yl]-quinoline;
{3'-[6-(1-methanesulfonyl-1-methyl-ethyl)-quinolin-8-yl]-biphenyl-4-yl}-methanol;
3-{3'-[6-(1-methanesulfonyl-1-methyl-ethyl)-quinolin-8-yl]-biphenyl-4-yl}-acrylic acid methyl ester;
6-(1-methanesulfonyl-1-methyl-ethyl)-8-[2'-(1-methyl-1H-imidazol-2-ylsulfanylmethyl)-biphenyl-3-yl]-quinoline;
3-{3'-[6-(1-methanesulfonyl-1-methyl-ethyl)-quinolin-8-yl]-biphenyl-2-yl}-propionic acid methyl;
3-{3'-[6-(1-methanesulfonyl-1-methyl-ethyl)-quinolin-8-yl]-biphenyl-2-yl}-prop-2-en-1-ol;
3-{3'-[6-(1-methanesulfonyl-1-methyl-ethyl)-quinolin-8-yl]-biphenyl-2-yl}-propan-1-ol;
{3'-[6-(1-methanesulfonyl-1-methyl-ethyl)-quinolin-8-yl]-biphenyl-3-yl}-methanol;
3-{3'-[6-(1-methanesulfonyl-1-methyl-ethyl)-quinolin-8-yl]-biphenyl-2-yl}-propionic acid;
3-{3'-[6-(1-methanesulfonyl-1-methyl-ethyl)-quinolin-8-yl]-biphenyl-3-yl}-acrylic acid;
3-{3'-[6-(1-methanesulfonyl-1-methyl-ethyl)-quinolin-8-yl]-biphenyl-3-yl}-propionic acid;
3-{3'-[6-(1-methanesulfonyl-1-methyl-ethyl)-quinolin-8-yl]-biphenyl-4-yl}-acrylic acid;
3'-[6-(1-methanesulfonyl-1-methyl-ethyl)-quinolin-8-yl]-biphenyl-2-carbonitrile;
6-(1-methanesulfonyl-1-methyl-ethyl)-8-(2'-methylsulfanyl-biphenyl-3-yl)-quinoline;
8-(2'-methanesulfonyl-biphenyl-3-yl)-6-(1-methanesulfonyl-1-methyl-ethyl)-quinoline;
{3'-[6-(1-methanesulfonyl-1-methyl-ethyl)-quinolin-8-yl]-biphenyl-3-yl}-acetic acid;
3'-[6-(1-methanesulfonyl-1-methyl-ethyl)-quinolin-8-yl]-biphenyl-3-carboxylic acid;
3-{3'-[6-(1-methanesulfonyl-1-methyl-ethyl)-quinolin-8-yl]-biphenyl-4-yl}-propionic acid methyl ester;
3-{3'-[6-(1-methanesulfonyl-1-methyl-ethyl)-quinolin-8-yl]-biphenyl-4-yl}-propionic acid;
2-{3'-[6-(1-methanesulfonyl-1-methyl-ethyl)-quinolin-8-yl]-biphenyl-4-yl}-cyclopropanecarboxylic acid methyl ester;

3'-[6-(1-methanesulfonyl-1-methyl-ethyl)-quinolin-8-yl]-biphenyl-3-carboxylic acid amide;
2-{3'-[6-(1-methanesulfonyl-1-methyl-ethyl)-quinolin-8-yl]-biphenyl-3-yl}-cyclopropanecarboxylic acid;
3-{3'-[6-(1-methanesulfonyl-1-methyl-ethyl)-quinolin-8-yl]-biphenyl-4-yl}-2-methyl-propionic acid tert-butyl ester;
3-{3'-[6-(1-methanesulfonyl-1-methyl-ethyl)-quinolin-8-yl]-biphenyl-4-yl}-2-methyl-propionic acid;
2-{3'-[6-(1-methanesulfonyl-1-methyl-ethyl)-quinolin-8-yl]-biphenyl-4-yl}-2-methyl-propionic acid methyl ester;
{3'-[6-(1-methanesulfonyl-1-methyl-ethyl)-quinolin-8-yl]-biphenyl-4-yl}-acetic acid;
1-{3'-[6-(1-methanesulfonyl-1-methyl-ethyl)-quinolin-8-yl]-biphenyl-4-yl}-cyclopropanecarboxylic acid amide;
2-{3'-[6-(1-methanesulfonyl-1-methyl-ethyl)-quinolin-8-yl]-biphenyl-3-yl}-2-methyl-propionic acid;
(1-{3'-[6-(1-methanesulfonyl-1-methyl-ethyl)-quinolin-8-yl]-biphenyl-4-ylmethylsulfanylmethyl}-cyclopropyl)-acetic acid;
(1-{3'-[6-(1-methanesulfonyl-1-methyl-ethyl)-quinolin-8-yl]-biphenyl-4-ylmethanesulfonyl-methyl}-cyclopropyl)-acetic acid;
3-{3'-[6-(1-methanesulfonyl-1-methyl-ethyl)-quinolin-8-yl]-biphenyl-4-yl}-acrylic acid methyl ester;
1-{3'-[6-(1-methanesulfonyl-1-methyl-ethyl)-quinolin-8-yl]-biphenyl-4-ylmethyl}-cyclobutanecarboxylic acid;
6-(1-methanesulfonyl-1-methyl-ethyl)-8-{4'-[2-(1H-tetrazol-5-yl)-cyclopropyl]-biphenyl-3-yl}-quinoline;
(1-{3'-[6-(1-methanesulfonyl-1-methyl-ethyl)-quinolin-8-yl]-biphenyl-4-ylsulfanylmethyl}-cyclopropyl)-acetic acid;
(1-{3'-[6-(1-methanesulfonyl-1-methyl-ethyl)-quinolin-8-yl]-biphenyl-4-sulfonylmethyl}-cyclopropyl)-acetic acid;
3-{3'-[6-(1-methanesulfonyl-1-methyl-ethyl)-quinolin-8-yl]-biphenyl-4-yl}-acrylic acid;
or a pharmaceutically acceptable salt thereof.

20. The compound according to claim 1, consisting of
6-(1-methanesulfonyl-1-methyl-ethyl)-8-[3-(5-trifluoromethyl-pyridin-2-yl)-phenyl]-quinoline;
6-(1-methanesulfonyl-1-methyl-ethyl)-8-[3-(3-methyl-pyridin-2-yl)-phenyl]-quinoline;
6-(1-methanesulfonyl-1-methyl-ethyl)-8-(3-pyridin-3-yl-phenyl)-quinoline;
6-(1-methanesulfonyl-1-methyl-ethyl)-8-(3-pyridin-4-yl-phenyl)-quinoline;
6-(1-methanesulfonyl-1-methyl-ethyl)-8-[3-(5-methanesulfonyl-pyridin-3-yl)-phenyl]-quinoline;
6-(1-methanesulfonyl-1-methyl-ethyl)-8-[3-(6-methylsulfanyl-pyridin-2-yl)-phenyl]-quinoline;
6-(1-methanesulfonyl-1-methyl-ethyl)-8-[3-(6-methylsulfanyl-pyridin-3-yl)-phenyl]-quinoline;
2-(6-{3-[6-(1-methanesulfonyl-1-methyl-ethyl)-quinolin-8-yl]-phenyl}-pyridin-3-yl)-propan-2-ol;
6-(1-methanesulfonyl-1-methyl-ethyl)-8-[3-(6-methyl-pyridin-3-yl)-phenyl]-quinoline;
5-{3-[6-(1-methanesulfonyl-1-methyl-ethyl)-quinolin-8-yl]-phenyl}-nicotinic acid ethyl ester;
6-(1-methanesulfonyl-1-methyl-ethyl)-8-{3-[6-(propane-2-sulfonyl)-pyridin-3-yl]-phenyl}-quinoline;
8-[3-(6-benzyloxy-pyridin-3-yl)-phenyl]-6-(1-methanesulfonyl-1-methyl-ethyl)-quinoline;
2-(5-{3-[6-(1-methanesulfonyl--methyl-ethyl)-quinolin-8-yl]-phenyl}-pyridin-3-yl)-propan-2-ol;
6-(1-methanesulfonyl-1-methyl-ethyl)-8-{3-[5-(2-trimethylsilanyl-ethylsulfanyl)-pyridin-3-yl]-phenyl}-quinoline;
8-{3-[5-(4-fluoro-benzylsulfanyl)-pyridin-3-yl]-phenyl}-6-(1-methanesulfonyl-1-methyl-ethyl)-quinoline;
N-cyclopropyl-5-{3-[6-(1-methanesulfonyl-1-methyl-ethyl)-quinolin-8-yl]-phenyl}-nicotinamide;
3-{3-[6-(1-methanesulfonyl-1-methyl-ethyl)-quinolin-8-yl]-phenyl}-5-trifluoromethyl-pyridin-2-ylamine;
dicyclopropyl-(5-{3-[6-(1-methanesulfonyl-1-methyl-ethyl)-quinolin-8-yl]-phenyl}-1-oxy-pyridin-2-yl)-methanol;
8-[3-(6-ethanesulfonyl-pyridin-3-yl)-phenyl]-6-(1-methanesulfonyl-1-methyl-ethyl)-quinoline;
2-(5-{3-[6-(1-methanesulfonyl-1-methyl-ethyl)-quinolin-8-yl]-phenyl}-pyridin-2-yl)-propan-2-ol;
6-(1-methanesulfonyl-1-methyl-ethyl)-8-{3-[1-oxy-5-(2-trimethylsilanyl-ethanesulfonyl)-pyridin-3-yl]-phenyl}-quinoline;
8-(3-{5-[1,2-bis-(4-fluoro-phenyl)-ethanesulfonyl]-1-oxy-pyridin-3-yl}-phenyl)-6-(1-methanesulfonyl-1-methyl-ethyl)-quinoline;
8-[3-(5-ethanesulfinyl-1-oxy-pyridin-3-yl)-phenyl]-6-(1-methanesulfonyl-1-methyl-ethyl)-quinoline;
6-(1-methanesulfonyl-1-methyl-ethyl)-8-[3-(1-oxy-5-trifluoromethyl-pyridin-3-yl)-phenyl]-quinoline;
6-(1-methanesulfonyl-1-methyl-ethyl)-8-[3-(6-methanesulfonyl-5-methyl-pyridin-3-yl)-phenyl]-quinoline;
3-(5-{3-[6-(1-methanesulfonyl-1-methyl-ethyl)-quinolin-8-yl]-phenyl}-1-oxy-pyridin-2-yl)-pentan-3-ol;
(5-{3-[6-(1-methanesulfonyl-1-methyl-ethyl)-quinolin-8-yl]-phenyl}-1-oxy-pyridin-3-yl)-methanol;
difluoro-(5-{3-[6-(1-methanesulfonyl-1-methyl-ethyl)-quinolin-8-yl]-phenyl}-pyridin-3-ylsulfanyl)-acetic acid ethyl ester;
difluoro-(5-{3-[6-(1-methanesulfonyl-1-methyl-ethyl)-quinolin-8-yl]-phenyl}-pyridin-3-ylsulfanyl)-acetic acid;
(5-{3-[6-(1-methanesulfonyl-1-methyl-ethyl)-quinolin-8-yl]-phenyl}-1-oxy-pyridin-2-yl)-methanol;
1-isopropyl-3-(5-{3-[6-(1-methanesulfonyl-1-methyl-ethyl)-quinolin-8-yl]-phenyl}-pyridin-2-yl)-urea;
6-(1-methanesulfonyl-1-methyl-ethyl)-8-{3-[5-(2-trimethylsilanyl-ethanesulfonyl)-pyridin-3-yl]-phenyl}-quinoline;
8-[3-(4-chloro-pyridin-3-yl)-phenyl]-6-(1-methanesulfonyl-1-methyl-ethyl)-quinoline;
(5-{3-[6-(1-methanesulfonyl-1-methyl-ethyl)-quinolin-8-yl]-phenyl}-pyridin-2-yl)-(4-methylsulfanyl-phenyl)-methanone;
5-{3-[6-(1-methanesulfonyl-1-methyl-ethyl)-quinolin-8-yl]-phenyl}-1-oxy-pyridine-2-carboxylic acid isopropylamide;
1,1,1,3,3,3-hexafluoro-2-(5-{3-[6-(1-methanesulfonyl-1-methyl-ethyl)-quinolin-8-yl]-phenyl}-pyridin-3-yl)-propan-2-ol;
6-(1-methanesulfonyl-1-methyl-ethyl)-8-{3-[6-(4-methoxy-benzyloxy)-pyridin-2-yl]-phenyl}-quinoline;
1,1,1,3,3,3-hexafluoro-2-(5-{3-[6-(1-methanesulfonyl-1-methyl-ethyl)-quinolin-8-yl]-phenyl}-1-oxy-pyridin-3-yl)-propan-2-ol;
5-{3-[6-(1-methanesulfonyl-1-methyl-ethyl)-quinolin-8-yl]-phenyl}-nicotinic acid;
1,1,1,3,3,3-hexafluoro-2-(5-{3-[6-(1-methanesulfonyl-1-methyl-ethyl)-quinolin-8-yl]-phenyl}-1-oxy-pyridin-2-yl)-propan-2-ol;

5-{3-[6-(1-methanesulfonyl-1-methyl-ethyl)-quinolin-8-yl]-phenyl}-1-oxy-pyridine-2-carboxylic acid methyl ester;
5-{3-[6-(1-methanesulfonyl-1-methyl-ethyl)-quinolin-8-yl]-phenyl}-1-oxy-pyridine-2-carboxylic acid;
5-{3-[6-(1-methanesulfonyl-1-methyl-ethyl)-quinolin-8-yl]-phenyl}-1-oxy-nicotinic acid;
5-{3-[6-(1-methanesulfonyl-1-methyl-ethyl)-quinolin-8-yl]-phenyl}-1-oxy-nicotinonitrile;
5-{3-[6-(1-methanesulfonyl-1-methyl-ethyl)-quinolin-8-yl]-phenyl}-1-oxy-nicotinic acid 2,2-dimethyl-propionyloxymethyl ester;
8-[3-(5-chloro-1-oxy-pyridin-3-yl)-phenyl]-6-(1-methanesulfonyl-1-methyl-ethyl)-quinoline;
[1-(5-{3-[6-(1-methanesulfonyl-1-methyl-ethyl)-quinolin-8-yl]-phenyl}-pyridin-2-ylsulfanylmethyl)-cyclopropyl]-acetic acid;
[1-(5-{3-[6-(1-methanesulfonyl-1-methyl-ethyl)-quinolin-8-yl]-phenyl}-pyridine-2-sulfonylmethyl)-cyclopropyl]-acetic acid;
6-{3-[6-(1-methanesulfonyl-1-methyl-ethyl)-quinolin-8-yl]-phenyl}-1H-pyridin-2-one
or a pharmaceutically acceptable salt thereof.

21. The compound according to claim 1, consisting of
6-(1-methanesulfonyl-1-methyl-ethyl)-8-(3-thiophen-2-yl-phenyl)-quinoline;
1-(5-{3-[6-(1-methanesulfonyl-1-methyl-ethyl)-quinolin-8-yl]-phenyl}-thiophen-2-yl)-ethanone;
6-(1-methanesulfonyl-1-methyl-ethyl)-8-[3-(3-methyl-thiophen-2-yl)-phenyl]-quinoline;
5-{3-[6-(1-methanesulfonyl-1-methyl-ethyl)-quinolin-8-yl]-phenyl}-thiophene-2-sulfonic acid amide;
6-(1-methanesulfonyl-1-methyl-ethyl)-8-(3-quinolin-3-yl-phenyl)-quinoline;
8-(3-benzo[1,3]dioxol-5-yl-phenyl)-6-(1-methanesulfonyl-1-methyl-ethyl)-quinoline;
or a pharmaceutically acceptable salt thereof.

22. The compound according to claim 1, consisting of
6-(1-methanesulfonyl-1-methyl-ethyl)-8-(5-phenyl-pyridin-3-yl)-quinoline;
6-(1-methanesulfonyl-1-methyl-ethyl)-8-(1-oxy-5-phenyl-pyridin-3-yl)-quinoline;
or a pharmaceutically acceptable salt thereof.

23. A pharmaceutical composition comprising:
a therapeutically effective amount of the compound according to claim 1 or a pharmaceutically acceptable salt thereof; and a pharmaceutically acceptable carrier.

* * * * *